(12) United States Patent
Koshiba et al.

(10) Patent No.: US 9,227,949 B2
(45) Date of Patent: Jan. 5, 2016

(54) HETEROARYLCARBOXYLIC ACID ESTER DERIVATIVE

(71) Applicant: AJINOMOTO CO., INC., Tokyo (JP)

(72) Inventors: Takahiro Koshiba, Kawasaki (JP); Munetaka Tokumasu, Kawasaki (JP); Taisuke Ichimaru, Kawasaki (JP); Koji Ohsumi, Kawasaki (JP); Tadakiyo Nakagawa, Kawasaki (JP); Tatsuhiro Yamada, Kawasaki (JP); Kayo Matsumoto, Kawasaki (JP); Tamotsu Suzuki, Kawasaki (JP)

(73) Assignee: AJINOMOTO CO., INC., Tokyo (JP)

( * ) Notice: Subject to any disclaimer, the term of this patent is extended or adjusted under 35 U.S.C. 154(b) by 0 days.

(21) Appl. No.: 14/567,506

(22) Filed: Dec. 11, 2014

(65) Prior Publication Data
US 2015/0099733 A1   Apr. 9, 2015

Related U.S. Application Data

(63) Continuation of application No. PCT/JP2013/067015, filed on Jun. 14, 2013, and a continuation of application No. 13/517,805, filed on Jun. 14, 2012, now Pat. No. 9,024,044.

(51) Int. Cl.
| | |
|---|---|
| *A61K 31/38* | (2006.01) |
| *C07D 319/12* | (2006.01) |
| *C07D 333/38* | (2006.01) |
| *C07D 409/06* | (2006.01) |
| *C07D 409/12* | (2006.01) |
| *C07D 333/40* | (2006.01) |

(52) U.S. Cl.
CPC ............ *C07D 319/12* (2013.01); *C07D 333/38* (2013.01); *C07D 333/40* (2013.01); *C07D 409/06* (2013.01); *C07D 409/12* (2013.01)

(58) Field of Classification Search
USPC ........................................................ 514/430
See application file for complete search history.

(56) References Cited

U.S. PATENT DOCUMENTS

| | | | |
|---|---|---|---|
| 4,563,527 A | 1/1986 | Fujii et al. | |
| 5,532,267 A | 7/1996 | Nakayama et al. | |
| 6,262,114 B1 | 7/2001 | Nakai et al. | |
| 6,358,960 B1 | 3/2002 | Senokuchi et al. | |
| 8,609,715 B2 | 12/2013 | Konishi et al. | |
| 8,877,805 B2 | 11/2014 | Konishi et al. | |
| 2002/0128315 A1 | 9/2002 | Nakai et al. | |
| 2007/0298025 A1 | 12/2007 | Harosh et al. | |
| 2008/0009537 A1 | 1/2008 | Sakai | |
| 2010/0311690 A1 | 12/2010 | Harosh et al. | |
| 2012/0283222 A1 | 11/2012 | Konishi et al. | |
| 2013/0338132 A1 | 12/2013 | Koshiba et al. | |
| 2014/0080790 A1 | 3/2014 | Konishi et al. | |
| 2014/0094489 A1 | 4/2014 | Suzuki et al. | |
| 2015/0011511 A1 | 1/2015 | Konishi et al. | |

FOREIGN PATENT DOCUMENTS

| | | |
|---|---|---|
| JP | 61-022075 | 1/1986 |
| JP | 5-213927 | 8/1993 |
| JP | 8-143529 | 4/1996 |
| JP | 2008-266174 | 11/2008 |
| WO | WO 99/41231 A1 | 8/1999 |
| WO | WO 2006/050999 A2 | 5/2006 |
| WO | WO 2006/057152 A1 | 6/2006 |
| WO | WO 2009/071601 A1 | 6/2009 |
| WO | WO 2011/071048 | 6/2011 |
| WO | WO 2013/039187 A1 | 3/2013 |

OTHER PUBLICATIONS

Masashi Matsushima, et al. "Inhibition of Enteropeptidase by Antitrypsin drugs", Biomedical Research 22 (5), 2001, pp. 257-260.
T. Yokoyama, et al., "Studies on new Synthetic Inhibitors of Kallikreins and Chymotrypsin", Advances in Experimental Medicine and Biology, 1989, 247(B), pp. 271-276.
International Search Report issued in PCT/JP2013/067015 on Sep. 10, 2013.
Written Opinion issued in PCT/JP2013/067015 on Sep. 10, 2013.
Konishi, et al., DN 155:67824, 2011, 3 pages.

*Primary Examiner* — Rei-Tsang Shiao
(74) *Attorney, Agent, or Firm* — Oblon, McClelland, Maier & Neustadt, L.L.P.

(57) ABSTRACT

Compounds represented by the following formula (I);

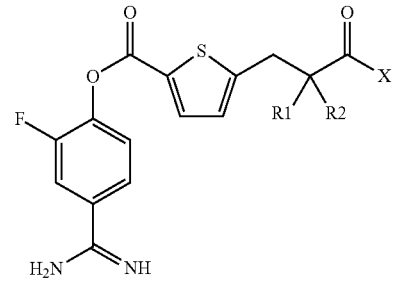

wherein each symbol is as defined in the specification, are useful as hyperglycemic inhibitors having a serine protease inhibitory action and as prophylactic or therapeutic drugs for diabetes.

13 Claims, 2 Drawing Sheets

HETEROARYLCARBOXYLIC ACID ESTER DERIVATIVE

CROSS REFERENCES TO RELATED APPLICATIONS

This application is a continuation of International Patent Application No. PCT/JP2013/067015, filed on Jun. 14, 2013, and a continuation of U.S. patent application Ser. No. 13/517, 805, filed on Jun. 14, 2012. Both of the above applications are incorporated herein by reference in their entireties.

BACKGROUND OF THE INVENTION

1. Field of the Invention

The present invention relates to novel compounds, heteroarylcarboxylic acid ester derivatives, which exhibit a serine protease (particularly trypsin and enteropeptidase) inhibitory activity. The present invention also relates to pharmaceutical compositions which contain such a compound and drugs for the treatment or prophylaxis of diabetes. The present invention further relates to methods for the treatment and/or prophylaxis of diabetes by administering such a heteroarylcarboxylic acid ester derivative.

2. Discussion of the Background

At present, insulin secretagogues (sulfonylureas), glucose absorption inhibitors (α-glucosidase inhibitors), insulin sensitizers (biguanide, thiazolidine derivatives), and the like are clinically used as therapeutic drugs for diabetes. However, since all of them are accompanied by side effects such as hypoglycemia, diarrhea, lactic acidosis, edema, and the like; show an insufficient effect; and the like, a medicament satisfying clinical needs is still needed.

In recent years, a benzoic acid ester having a protease inhibitory activity, which is represented by the following compound, has been reported to show a blood glucose elevation suppressing action in a diabetes animal model (see WO2006/057152, which is incorporated herein by reference in its entirety). The following compound is considered to show an enzyme inhibitory activity on trypsin, thrombin, pancreatic, and plasma kallikreins, plasmin and the like and a leukotriene receptor antagonistic action. Moreover, an enteropeptidase inhibitory activity of the following compound has also been reported (see Biomedical Research (2001), 22 (5) 257-260, which is incorporated herein by reference in its entirety). However, many unclear points remain in the relationship between such actions and a blood glucose elevation suppressing action.

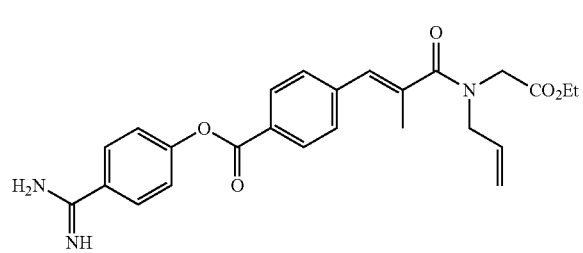 [SMILES: C=CCN(CC(=O)OCC)C(=O)/C(C)=C/c1ccc(C(=O)Oc2ccc(C(=N)N)cc2)cc1]

On the other hand, as for a heteroarylcarboxylic acid ester structures, JP-A-55-161385, which is incorporated herein by reference in its entirety, discloses a compound as a therapeutic drug for pancreatitis. In this document, only heteroarylcarboxylic acid ester compounds wherein the substituent of the heteroarylcarboxylic acid moiety is a methyl group or a methoxy group or unsubstituted compounds are disclosed, as represented by the following formula. While these compounds are disclosed as showing an inhibitory activity on trypsin, chymotrypsin and thrombin, no description is given as to the enteropeptidase inhibitory activity and blood glucose elevation suppressing action.

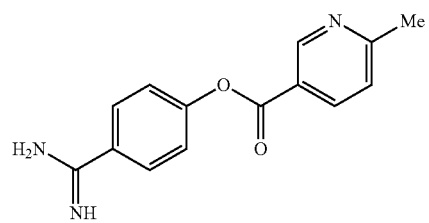 [SMILES: Cc1ccc(C(=O)Oc2ccc(C(=N)N)cc2)cn1]

In addition, Advances in Experimental Medicine and Biology (1989), 247B (Kinins 5, Pt. B), 271-6, which is incorporated herein by reference in its entirety, also describes a heteroarylcarboxylic acid ester having a protease inhibitory activity, which is represented by the following formula. However, only compounds wherein the heteroaryl moiety is unsubstituted are disclosed, and no description is given as to the enteropeptidase inhibitory activity and blood glucose elevation suppressing action of these compounds.

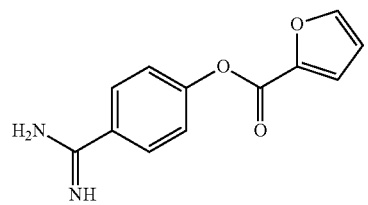 [SMILES: N=C(N)c1ccc(OC(=O)c2ccco2)cc1]

Furthermore, WO99/41231, which is incorporated herein by reference in its entirety, describes a compound represented by the following formula. However, it has a structure wherein an aryl group substituted by a carboxyl group is directly bonded to the heteroaryl moiety, which is completely different from the compound of the present invention. The document discloses an inhibitory activity against blood coagulation factor VIIa; however, no description is given as to the enteropeptidase inhibitory activity and blood glucose elevation suppressing action.

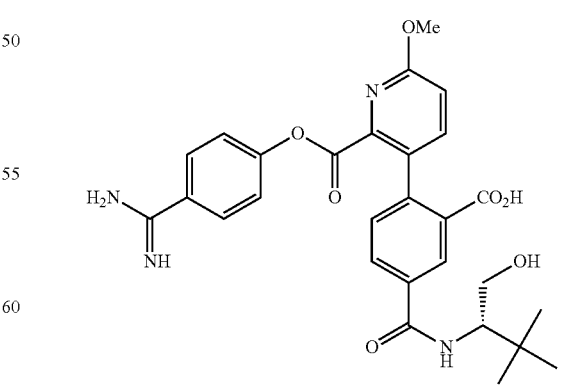

On the other hand, trypsin is one of the intestinal serine proteases and is produced by degradation of inactive trypsinogen by enteropeptidase. Trypsin is known to activate various digestive enzymes by acting on chymotrypsinogen, proelastase, procarboxylesterase, procolipase and pro-sucrase-isomaltase, and the like. Therefore, it is considered that an inhibitor of enteropeptidase and trypsin lowers the digestive capacity for protein, lipid, and carbohydrates, and is effective as a drug for the treatment or prophylaxis of obesity and hyperlipidemia.

WO2006/050999, which is incorporated herein by reference in its entirety, describes that a medicament that inhibits both enteropeptidase and trypsin is interesting as a body fat-reducing agent. In addition, WO2009/071601, which is incorporated herein by reference in its entirety reports a compound which has an inhibitory activity against enteropeptidase, trypsin, plasmin, kallikrein, and the like as an antiobesity drug. However, neither of these publications describes suppression of blood glucose elevation and hypoglycemic effect afforded by simultaneous inhibition of enteropeptidase and trypsin, and the protease inhibitor described therein has a structure completely different from that of the compound of the present invention.

Accordingly, there remains a need for compounds which are useful for the treatment or prophylaxis of diabetes. Therefore, to further satisfy the clinical needs from the aspects of effect, safety and the like, a hyperglycemic inhibitor having a serine protease inhibitory action, which is a new drug for the treatment or prophylaxis of diabetes, is desired.

SUMMARY OF THE INVENTION

Accordingly, it is one object of the present invention to provide novel compounds which are useful for the treatment or prophylaxis of diabetes.

It is another object of the present invention to provide novel compounds which exhibit a serine protease inhibitory action.

It is another object of the present invention to provide novel serine protease (particularly trypsin and enteropeptidase) inhibitors.

It is another object of the present invention to provide novel intestinal serine protease (particularly trypsin and enteropeptidase) inhibitors.

It is another object of the present invention to provide novel hyperglycemic inhibitors or hypoglycemic agents, and further, drugs for the treatment and/or prophylaxis of any of diabetes, obesity, hyperlipidemia, diabetic complication, and metabolic syndrome.

It is another object of the present invention to provide novel methods for the treatment and/or prophylaxis of any of diabetes, obesity, hyperlipidemia, diabetic complication, and metabolic syndrome.

It is another object of the present invention to provide novel methods for improving sensitivity to insulin.

These and other objects, which will become apparent during the following detailed description, have been achieved by the inventors' discovery that the heteroarylcarboxylic acid ester derivatives described below have serine protease inhibitory activity and are useful for the treatment and/or prophylaxis of any of diabetes, obesity, hyperlipidemia, diabetic complication, and metabolic syndrome.

Thus, in view of the above-mentioned current situation, the present inventors have conducted intensive studies and considered that simultaneous inhibition of trypsin and enteropeptidase is particularly effective for the suppression of blood glucose elevation. They have synthesized various heteroarylcarboxylic acid ester derivatives, which are novel compounds, evaluated trypsin and enteropeptidase inhibitory activity, and found that certain heteroarylcarboxylic acid ester derivatives are protease inhibitors that simultaneously inhibit them. Furthermore, they have also found that such representative compounds show a blood glucose elevation suppressing effect in a diabetes animal model.

Accordingly, the present invention provides a compound represented by the formula (I):

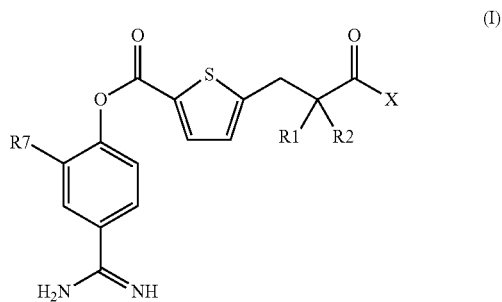

wherein:

$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;

X is —$OR^3$, —$NR^4R^5$ or a group represented by the formula (II):

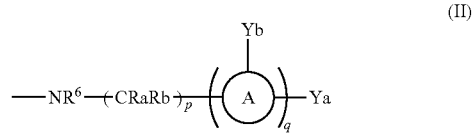

wherein:

$R^3$ is a hydrogen atom or a $C_{1-4}$ alkyl group;

$R^4$, $R^5$ and $R^6$ are the same or different and each is independently a hydrogen atom, a $C_{1-8}$ alkyl group, a carboxyl $C_{1-8}$ alkyl group or a $C_{3-8}$ alkenyl group, or $R^4$ and $R^5$ together with the nitrogen atom to which they are bonded form a $C_{2-9}$ heterocycle, wherein said $C_{1-8}$ alkyl group, said carboxyl $C_{1-8}$ alkyl group, said $C_{3-8}$ alkenyl group and said $C_{2-9}$ heterocycle may be substituted with one or more substituents;

Ra and Rb are the same or different and each is independently a hydrogen atom, a $C_{1-8}$ alkyl group, a carboxyl $C_{1-8}$ alkyl group, a carboxyl group, an aryl group, a $C_{3-6}$ heterocyclic group containing 1 to 4 heteroatoms selected from the group of O, N and S, or a $C_{3-8}$ cycloalkyl group, or Ra and Rb together with the atom(s) to which they are bonded form a $C_{3-8}$ cycloalkane ring, or a $C_{3-9}$ heterocycle containing 1-4 heteroatoms selected from the group of O, N and S, wherein said $C_{1-8}$ alkyl group, said carboxyl $C_{1-8}$ alkyl group, said aryl group, said $C_{3-6}$ heterocyclic group, said $C_{3-8}$ cycloalkyl group, said $C_{3-8}$ cycloalkane ring and said $C_{3-9}$ heterocycle may be substituted with one or more substituents;

Ring A is an arene, a $C_{3-6}$ heterocycle containing 1-4 heteroatoms selected from the group of O, N and S, a $C_{3-8}$ cycloalkane ring or a $C_{3-8}$ cycloalkene ring, wherein said $C_{3-6}$ heterocycle, said $C_{3-8}$ cycloalkane ring and said $C_{3-8}$ cycloalkene ring may be further substituted with an oxo group, in addition to Ya and Yb;

Ya is a hydrogen atom, a halogen atom, a carboxyl group, a hydroxyl group, a $C_{1-3}$ alkoxy-carbonyl group, a carboxyl $C_{1-3}$ alkyl group or a sulfo group;

Yb is a hydrogen atom, a halogen atom, a carboxyl group, a hydroxyl group, a $C_{1-3}$ alkoxy-carbonyl group, a carboxyl $C_{1-3}$ alkyl group, a nitro group, a cyano group or a $C_{1-3}$ alkoxyl group;

p is 0, 1, 2, 3 or 4;

q is 0 or 1; and $R^7$ is a hydrogen atom, a halogen atom or a nitro group;

with the proviso that when $R^1$ and $R^2$ are both methyl groups, then X is not a group represented by the formula:

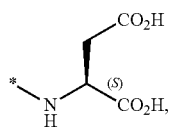

or a pharmaceutically acceptable salt thereof.

Further, the present invention provides a compound represented by the formula (I):

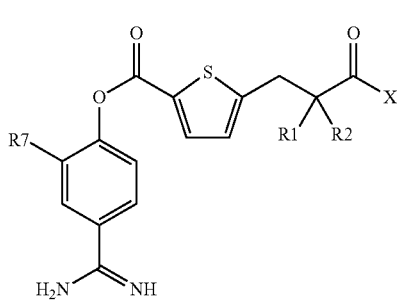

wherein:

$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;

X is —$OR^3$, —$NR^4R^5$ or a group represented by the formula (II):

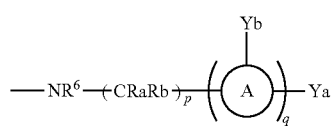

wherein:

$R^3$ is a hydrogen atom or a $C_{1-4}$ alkyl group;

$R^4$, $R^5$ and $R^6$ are the same or different and each is independently a hydrogen atom, a $C_{1-8}$ alkyl group, a carboxyl $C_{1-8}$ alkyl group or a $C_{3-8}$ alkenyl group, or $R^4$ and $R^5$ together with the nitrogen atom to which they are bonded form a $C_{3-9}$ heterocycle, wherein said $C_{1-8}$ alkyl group, said $C_{3-8}$ alkenyl group and said $C_{3-9}$ heterocycle may be substituted with one or more substituents;

Ra and Rb are the same or different and each is independently a hydrogen atom, a $C_{1-8}$ alkyl group, a carboxyl $C_{1-8}$ alkyl group, a carboxyl group, an aryl group, a $C_{3-6}$ heterocyclic group containing 1 to 4 heteroatoms selected from the group of O, N and S, or a $C_{3-8}$ cycloalkyl group, or Ra and Rb together with the atom(s) to which they are bonded form a $C_{3-8}$ cycloalkane ring or a $C_{3-9}$ heterocycle containing 1-4 heteroatoms selected from the group of O, N and S, wherein said $C_{1-8}$ alkyl group, said aryl group, said $C_{3-8}$ cycloalkyl group, said $C_{3-8}$ cycloalkane ring and said $C_{3-9}$ heterocycle may be substituted with one or more substituents;

Ring A is an arene, a $C_{3-6}$ heterocycle containing 1-4 heteroatoms selected from the group of O, N and S, or a $C_{3-8}$ cycloalkane ring;

Ya is a hydrogen atom, a halogen atom, a carboxyl group, a hydroxyl group, a carbonyl group, a carboxyl $C_{1-3}$ alkyl group or a sulfo group;

Yb is a hydrogen atom, a halogen atom, a carboxyl group, a hydroxyl group, a carbonyl group, a carboxyl $C_{1-3}$ alkyl group, a nitro group, a cyano group or a $C_{1-3}$ alkoxyl group;

p is 0, 1, 2, 3 or 4;

q is 0 or 1; and $R^7$ is a hydrogen atom, a halogen atom or a nitro group;

with the proviso that when $R^1$ and $R^2$ are both methyl groups, then neither of $R^4$ nor $R^5$ is an ethyl group substituted with two carboxyl groups, and when $R^1$ and $R^2$ are both methyl groups, then the group represented by the formula (II) is not a group represented by the formula:

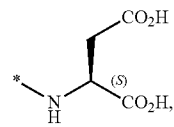

or a pharmaceutically acceptable salt thereof.

The present invention also provides a compound represented by the aforementioned formula (I), wherein X is —$NR^4R^5$ or the group represented by the formula (II), wherein $R^4$, $R^5$ and $R^6$ are each independently a hydrogen atom or a $C_{1-8}$ alkyl group, or a pharmaceutically acceptable salt thereof.

The present invention also provides a compound represented by the aforementioned formula (I), wherein X is —$NR^4R^5$, wherein $R^4$ and $R^5$ together with the nitrogen atom to which they are bonded form a $C_{2-9}$ heterocycle substituted by a halogen atom, a carboxyl group, a carboxyl $C_{1-3}$ alkyl group or a hydroxyl group, or a pharmaceutically acceptable salt thereof.

The present invention also provides a compound represented by the aforementioned formula (I), wherein X is a m group represented by the formula (II), wherein p=1 or 2, and q=0, or a pharmaceutically acceptable salt thereof.

The present invention also provides a compound represented by the aforementioned formula (I), wherein X is a group represented by the formula (II), wherein p=0 and q=1, is or a pharmaceutically acceptable salt thereof.

The present invention also provides a compound represented by the aforementioned formula (I), wherein X is a group represented by the formula (II), wherein p=1, q=1, and Ra and Rb are the same or different and each is independently a hydrogen atom or a $C_{1-8}$ alkyl group, or Ra and Rb together with the atom(s) to which they are bonded form a $C_{3-8}$ cycloalkane ring, wherein said $C_{1-8}$ alkyl group and said $C_{3-8}$ cycloalkane ring may substituted with a group selected from a carboxyl group, a carbamoyl group, a hydroxyl group, a phenyl group and a $C_{3-6}$ cycloalkyl group, or a pharmaceutically acceptable salt thereof.

The present invention also provides a compound represented by the aforementioned formula (I), wherein $R^1$ and $R^2$ are the same or different and each is independently a methyl group, an ethyl group or a propyl group, or $R^1$ and $R^2$ together with the carbon atom to which they are bonded form a cyclobutane ring or a cyclopentane ring, or a pharmaceutically acceptable salt thereof.

The present invention also provides a compound represented by the aforementioned formula (I), wherein $R^1$ and $R^2$ are the same or different and each is independently a methyl group, an ethyl group or a propyl group, or $R^1$ and $R^2$ together with the carbon atom to which they are bonded form a cyclobutane ring or a cyclopentane ring, and X is —OH, or a pharmaceutically acceptable salt thereof.

The present invention also provides a compound represented by the aforementioned formula (I), wherein X is the group represented by the formula (II), wherein q=1, and Ring A is a benzene ring, a pyridine ring, a 1,2-dihydropyridine ring, or a $C_{3-6}$ heterocycle containing 1-4 oxygen atoms, wherein said 1,2-dihydropyridine ring and said $C_{3-6}$ heterocycle containing 1-4 oxygen atoms may be further substituted with an oxo group, in addition to Ya and Yb, or a pharmaceutically acceptable salt thereof.

The present invention also provides a compound represented by the aforementioned formula (I), wherein X is a group represented by the formula (II), wherein q=1, Ya is a halogen atom, a carboxyl group, a carboxyl $C_{1-3}$ alkyl group, a hydroxyl group, a sulfo group or a $C_{1-3}$ alkoxy-carbonyl group, and Yb is a hydrogen atom, a halogen atom, a carboxyl group or a hydroxyl group, or a pharmaceutically acceptable salt thereof.

The present invention also provides a compound represented by the aforementioned formula (I), wherein X is —$NR^4R^5$, wherein when $R^4$ or $R^5$ has substituent(s), said substituent is selected from a halogen atom, a carboxyl group, a hydroxyl group, a carboxyl alkyl group, a $C_{3-8}$ alkenyl group, a carbamoyl group, a phenyl group, an amino group, a sulfo group, a cyano group, a $C_{3-8}$ cycloalkyl group, and a $C_{1-8}$ heterocyclic group containing 1 to 4 heteroatoms selected from the group consisting of O, N and S, or a pharmaceutically acceptable salt thereof.

The present invention also provides a compound represented by the aforementioned formula (I), wherein X is a group represented by the formula (II), wherein, when Ra or Rb has substituent(s), said substituent is selected from a carboxyl group, a hydroxyl group, a phenyl group, an amino group, a methylthio group, a sulfanyl group, a carbamoyl group, a guanidino group, a $C_{3-8}$ cycloalkyl group, and a $C_{1-8}$ heterocyclic group containing 1-4 heteroatoms selected from the group consisting of O, N and S, or a pharmaceutically acceptable salt thereof.

The present invention also provides a compound represented by the aforementioned formula (I), wherein $R^4$ is (1) a carboxyl $C_{1-8}$ alkyl group optionally substituted by 1 to 3 substituents selected from (a) a hydroxyl group, (b) an aryl group, (c) a $C_{3-8}$ cycloalkyl group, (d) a carbamoyl group, (e) an amino group, (f) an aryl group optionally substituted by a hydroxyl group, (g) a $C_{1-3}$ alkylcarbamoyl group optionally substituted by a carboxyl group, and (h) a heterocyclic group, or (2) a $C_{1-8}$ alkyl group optionally substituted by 1 to 3 substituents selected from (a) a sulfo group, (b) a cyano group, (c) a $C_{1-8}$ heterocyclic group, and (d) an aryl group optionally substituted by a carboxyl group, and $R^5$ is a hydrogen atom, a $C_{1-3}$ alkyl group optionally substituted by a $C_{3-8}$ cycloalkyl group, or a $C_{3-8}$ alkenyl group; or $R^4$ and $R^5$ together with the nitrogen atom to which they are bonded form a $C_{2-9}$ heterocycle substituted by 1 to 3 substituents selected from (1) a halogen atom, (2) a hydroxyl group, (3) a carboxyl group, and (4) a carboxyl $C_{1-3}$ alkyl group;

$R^6$ is a hydrogen atom, a $C_{1-3}$ alkyl group optionally substituted by a $C_{3-8}$ cycloalkyl group, or a $C_{3-8}$ alkenyl group; and Ra and Rb are the same or different and each is independently (1) a hydrogen atom, (2) a $C_{1-8}$ alkyl group optionally substituted by 1 to 3 substituents selected from (a) an aryl group, (b) a hydroxyl group, (c) a carbamoyl group, and (d) a $C_{1-8}$ heterocyclic group containing 1 to 4 heteroatoms selected from O, N and S, (3) a carboxyl $C_{1-8}$ alkyl group, (4) an aryl group optionally substituted by a hydroxyl group, (5) a $C_{3-6}$ heterocyclic group containing 1 to 4 heteroatoms selected from the group of O, N and S, or (6) a $C_{3-8}$ cycloalkyl group, or Ra and Rb together with the atom(s) to which they are bonded form a $C_{3-8}$ cycloalkane ring, or a $C_{3-8}$ heterocycle containing 1-4 heteroatoms selected from the group of O, N and S, each of which is optionally substituted by an oxo group, or a pharmaceutically acceptable salt thereof.

The present invention also provides a compound represented by the aforementioned formula (I), wherein X is —$OR^3$, or a pharmaceutically acceptable salt thereof.

The present invention also provides a compound represented by the aforementioned formula (I), wherein X is —OH, or a pharmaceutically acceptable salt thereof.

The present invention also provides a compound represented by the aforementioned formula (I), wherein X is —OH, —$NR^4R^5$ or a group represented by the formula (II), and each of —$NR^4R^5$ and the group represented by the formula (II) has one carboxyl group, or a pharmaceutically acceptable salt thereof.

Further, the present invention provides a compound represented by the formula (I), wherein:

$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;

X is —$OR^3$ or —$NR^8R^9$; wherein $R^3$ is a hydrogen atom or a $C_{1-4}$ alkyl group;

$R^8$ is an optionally substituted $C_{1-8}$ alkyl group, an optionally substituted aryl group, an optionally substituted $C_{3-6}$ heterocyclic group, an optionally substituted $C_{3-8}$ cycloalkyl group, or an optionally substituted $C_{3-8}$ cycloalkenyl group, and $R^9$ is a hydrogen atom, an optionally substituted $C_{1-8}$ alkyl group or an optionally substituted $C_{3-8}$ alkenyl group; or $R^8$ and $R^9$ together with the nitrogen atom to which they are bonded form an optionally substituted $C_{2-8}$ heterocycle; and $R^7$ is a hydrogen atom, a halogen atom or a nitro group;

with the proviso that when $R^1$ and $R^2$ are both methyl groups, then X is not a group represented by the formula:

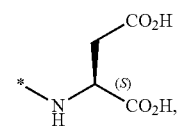

or a pharmaceutically acceptable salt thereof.

The present invention also provides a compound represented by the aforementioned formula (I), wherein R$^8$ is (1) a C$_{1-8}$ alkyl group optionally substituted by 1 to 3 substituents selected from (a) a carboxyl group, (b) a hydroxyl group, (c) an aryl group optionally substituted by a carboxyl group or a hydroxyl group, (d) a sulfo group, (e) a C$_{3-8}$ cycloalkyl group, (f) a carbamoyl group, (g) an amino group, (h) a cyano group, (i) a C$_{1-8}$ heterocyclic group, and (j) a C$_{1-3}$ alkylcarbamoyl group optionally substituted by a carboxyl group, (2) an aryl group optionally substituted by 1 to 3 substituents selected from (a) a carboxyl group, (b) a hydroxyl group, (c) a C$_{1-3}$ alkyl group optionally substituted by a carboxyl group, (d) a C$_{1-3}$ alkoxy-carbonyl group, and (e) a sulfo group, (3) a C$_{3-6}$ heterocyclic group optionally substituted by 1 to 3 substituents selected from (a) an oxo group, (b) a C$_{1-3}$ alkoxyl group, and (c) a halogen atom, (4) a C$_{3-8}$ cycloalkyl group optionally substituted by a carboxyl group, or (5) a C$_{3-8}$ cycloalkenyl group optionally substituted by a carboxyl group, and R$^9$ is a hydrogen atom, a C$_{1-8}$ alkyl group optionally substituted by a C$_{3-8}$ cycloalkyl group, or a C$_{3-6}$ alkenyl group; or R$^8$ and R$^9$ together with the nitrogen atom to which they are bonded form a C$_{2-9}$ heterocycle optionally substituted by 1 to 3 substituents selected from (1) a carboxyl group, (2) a C$_{1-3}$ alkyl group optionally substituted by a carboxyl group, (3) a halogen atom, and (4) a hydroxyl group, or a pharmaceutically acceptable salt thereof.

The present invention also provides a compound represented by the aforementioned formula (I), wherein X is —OH or —NR$^{8'}$R$^{9'}$, wherein R$^{8'}$ is a substituted C$_{1-8}$ alkyl group, a substituted aryl group, a substituted C$_{3-6}$ heterocyclic group, a substituted C$_{3-8}$ cycloalkyl group, or a substituted C$_{3-8}$ cycloalkenyl group, each of which has one carboxyl group, and R$^{9'}$ is a hydrogen atom, an optionally substituted C$_{1-8}$ alkyl group which has no carboxyl group, or an optionally substituted C$_{3-8}$ alkenyl group which has no carboxyl group; or R$^{8'}$ and R$^{9'}$ together with the nitrogen atom to which they are bonded form a substituted C$_{2-9}$ heterocycle which has one carboxyl group, or a pharmaceutically acceptable salt thereof.

The present invention also provides a compound represented by the aforementioned formula (I), wherein R$^{8'}$ is (1) a C$_{1-8}$ alkyl group substituted by 1 to 3 substituents selected from (a) a carboxyl group, (b) a hydroxyl group, (c) an aryl group optionally substituted by a carboxyl group or a hydroxyl group, (d) a sulfo group, (e) a C$_{3-8}$ cycloalkyl group, (f) a carbamoyl group, (g) an amino group, (h) a cyano group, (i) a C$_{1-8}$ heterocyclic group, and (j) a C$_{1-3}$ alkylcarbamoyl group optionally substituted by a carboxyl group, provided that said substituted C$_{1-8}$ alkyl group has one carboxyl group, (2) an aryl group substituted by 1 to 3 substituents selected from (a) a carboxyl group, (b) a hydroxyl group, (c) a C$_{1-3}$ alkyl group optionally substituted by a carboxyl group, (d) a C$_{1-3}$ alkoxy-carbonyl group, and (e) a sulfo group, provided that said substituted aryl group has one carboxyl group, (3) a C$_{3-8}$ cycloalkyl group substituted by one carboxyl group, or (4) a C$_{3-8}$ cycloalkenyl group substituted by one carboxyl group, and R$^{9'}$ is a hydrogen atom, a C$_{1-8}$ alkyl group optionally substituted by a C$_{3-8}$ cycloalkyl group, or a C$_{3-8}$ alkenyl group; or R$^{8'}$ and R$^{9'}$ together with the nitrogen atom to which they is are bonded form a C$_{2-9}$ heterocycle substituted by 1 to 3 substituents selected from (1) a carboxyl group, (2) a C$_{1-3}$ alkyl group optionally substituted by a carboxyl group, (3) a halogen atom, and (4) a hydroxyl group, provided that said substituted C$_{2-9}$ heterocycle formed by R$^{8'}$ and R$^{9'}$ has one carboxyl group, or a pharmaceutically acceptable salt thereof.

The present invention also provides a compound represented by the aforementioned formula (I), wherein R$^1$ and R$^2$ are the same or different and each is independently a C$_{1-3}$ alkyl group, or a pharmaceutically acceptable salt thereof.

The present invention also provides a compound represented by the aforementioned formula (I), wherein R$^7$ is a halogen atom, or a pharmaceutically acceptable salt thereof.

Further, the present invention provides a compound represented by any of the following formulae:

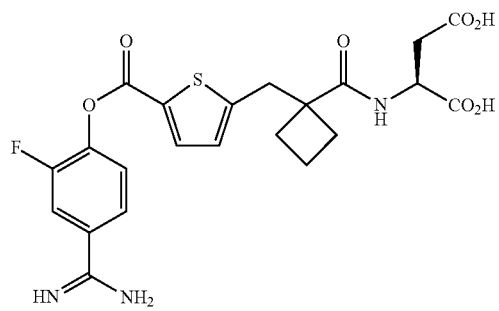

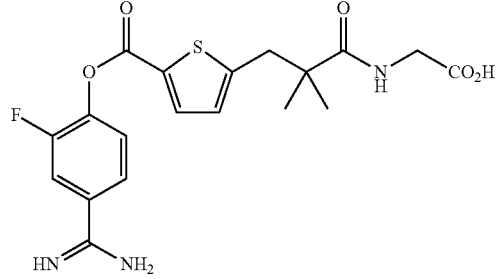

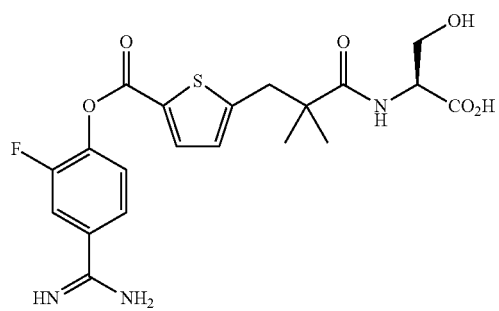

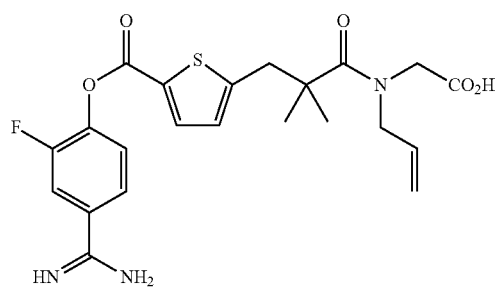

11
-continued
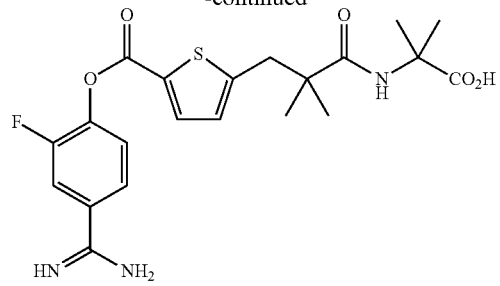
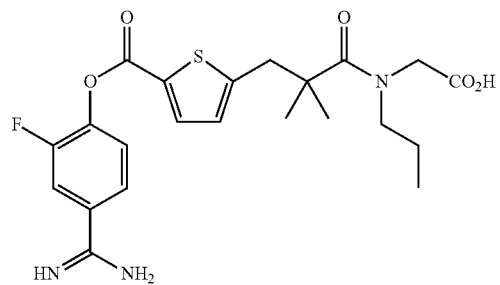
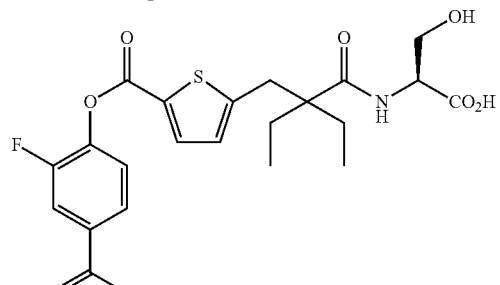
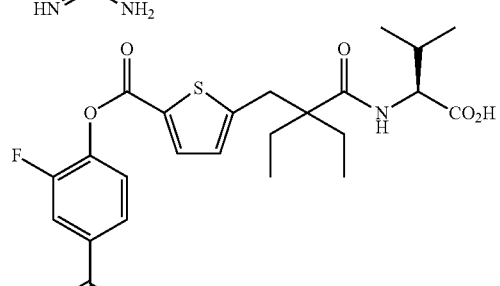
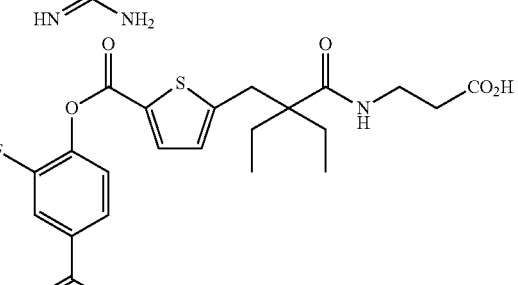
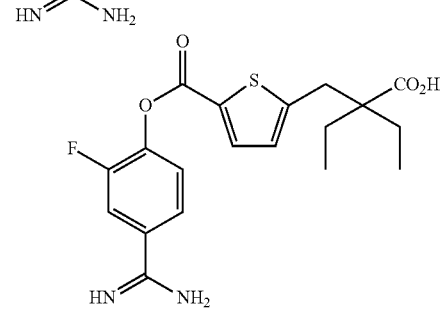
12
-continued
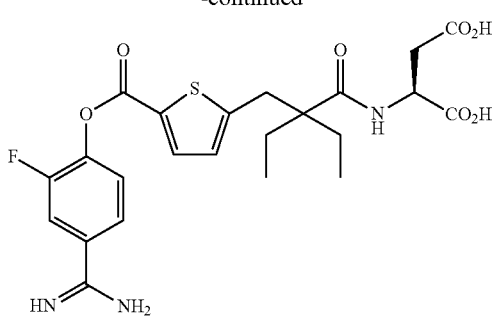
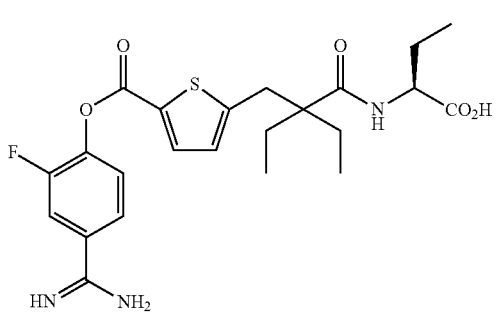
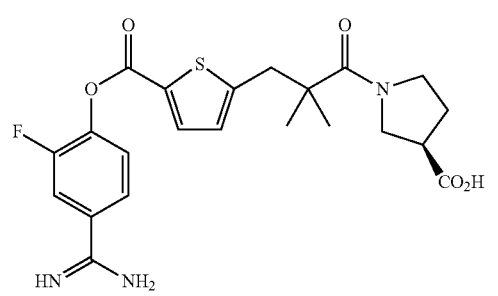
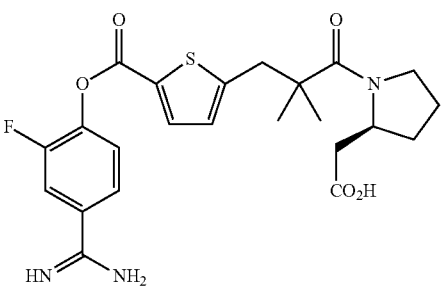
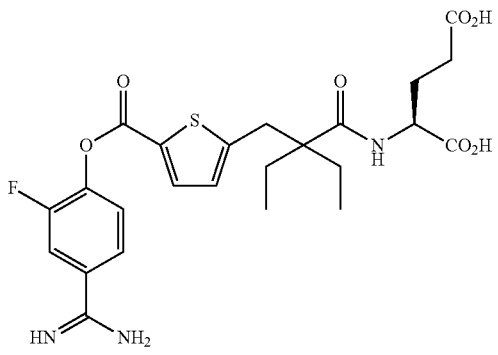

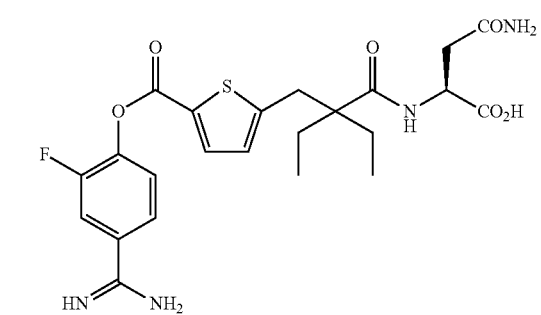
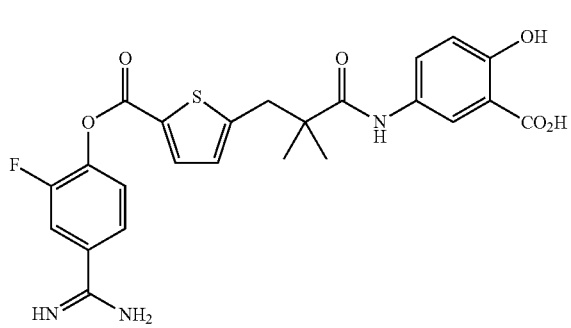
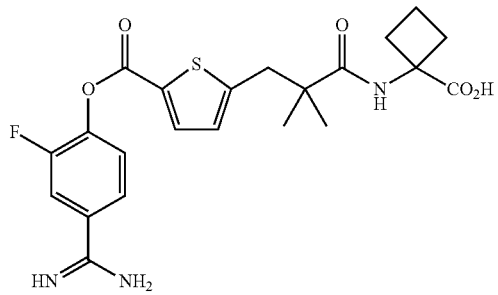
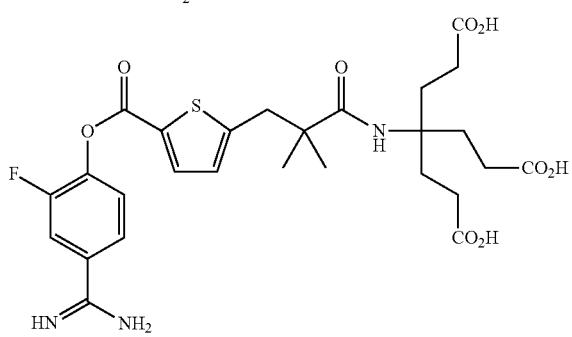
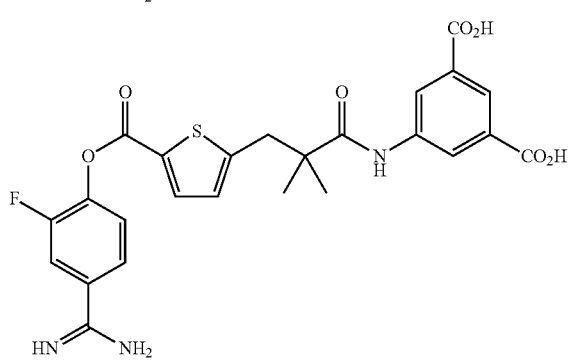
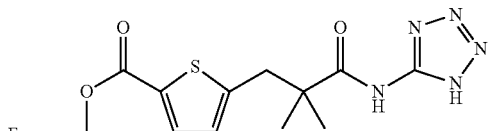
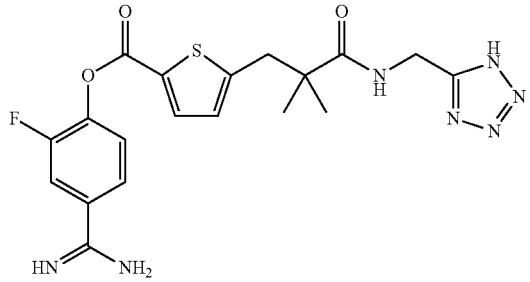
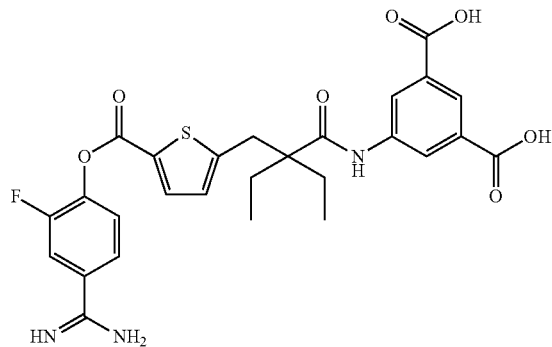
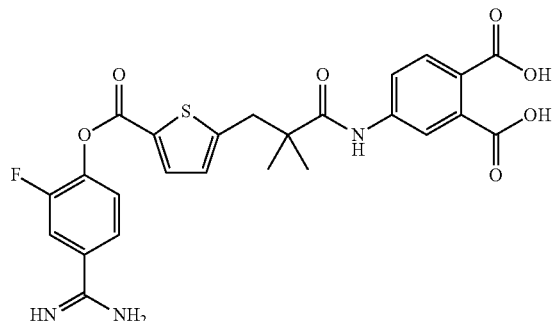
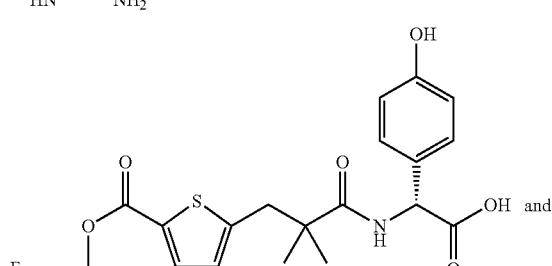

-continued

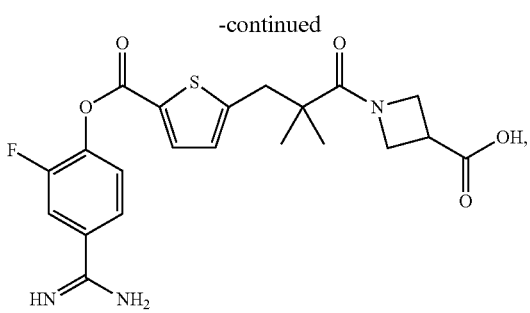

or a pharmaceutically acceptable salt of said compound.

Further, the present invention provides a compound represented by any of the following formulae:

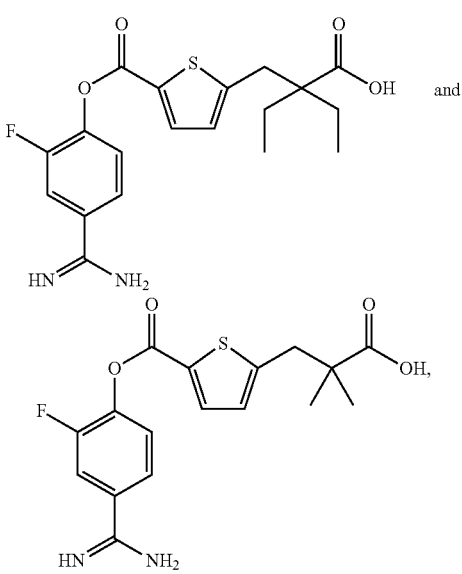

or a pharmaceutically acceptable salt of said compound.

Further, the present invention provides a pharmaceutical composition, comprising the above-mentioned compound or a pharmaceutically acceptable salt thereof, and at least one pharmaceutically acceptable carrier or excipient.

Further, the present invention provides a pharmaceutical composition comprising the above-mentioned compound, or a pharmaceutically acceptable salt thereof as an active ingredient.

The present invention also provides a method of inhibiting serine protease, comprising administering an effective amount of the above-mentioned compound or a pharmaceutically acceptable salt thereof to a subject in need thereof.

The present invention also provides a method of inhibiting intestinal serine protease, comprising administering an effective amount of the above-mentioned compound or a pharmaceutically acceptable salt thereof to a subject in need thereof.

The present invention also provides a method for inhibiting trypsin and enteropeptidase, comprising administering an effective amount of the above-mentioned compound or a pharmaceutically acceptable salt thereof to a subject in need thereof.

The present invention also provides a method for treating hyperglycemia, comprising administering an effective amount of the above-mentioned compound or a pharmaceutically acceptable salt thereof to a subject in need thereof.

The present invention also provides a method for prophylaxis or treatment of diabetes, comprising administering an effective amount of the above-mentioned compound or a pharmaceutically acceptable salt thereof to a subject in need thereof.

The present invention also provides a method for improving sensitivity to insulin, comprising administering an effective amount of the above-mentioned compound or a pharmaceutically acceptable salt thereof to a subject in need thereof.

The present invention also provides a method for prophylaxis or treatment of obesity, hyperlipidemia, a diabetic complication or metabolic syndrome, comprising administering an effective amount of the above-mentioned compound or a pharmaceutically acceptable salt thereof to a subject in need thereof.

The present invention also provides an intestinal serine protease inhibitor, comprising the above-mentioned compound, or a pharmaceutically acceptable salt thereof as an active ingredient.

The present invention also provides a dual inhibitor of trypsin and enteropeptidase, comprising the above-mentioned compound, or a pharmaceutically acceptable salt thereof as an active ingredient.

The present invention also provides a hyperglycemic inhibitor or hypoglycemic agent, comprising the above-mentioned compound, or a pharmaceutically acceptable salt thereof as an active ingredient.

The present invention also provides a prophylactic or therapeutic drug for diabetes, comprising the above-mentioned compound, or a pharmaceutically acceptable salt thereof as an active ingredient.

The present invention also provides an insulin sensitizer comprising the above-mentioned compound, or a pharmaceutically acceptable salt thereof as an active ingredient.

The present invention also provides a prophylactic or therapeutic drug for obesity, hyperlipidemia, diabetic complication or metabolic syndrome, comprising the above-mentioned compound, or a pharmaceutically acceptable salt thereof as an active ingredient.

The present invention also provides use of the above-mentioned compound, or a pharmaceutically acceptable salt thereof for the prophylaxis or treatment of diabetes.

The present invention also provides use of the above-mentioned compound, or a pharmaceutically acceptable salt thereof for the improvement of insulin resistance.

The present invention also provides use of the above-mentioned compound, or a pharmaceutically acceptable salt thereof for the prophylaxis or treatment of obesity, hyperlipidemia, diabetic complication or metabolic syndrome.

The present invention also provides a method for treating hyperglycemia or diabetes, comprising administering an effective amount of a compound represented by formula (I):

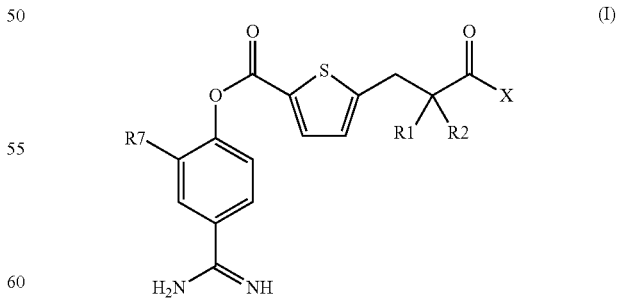

wherein:

$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;

X is —OR³, —NR⁴R⁵ or a group represented by formula (II):

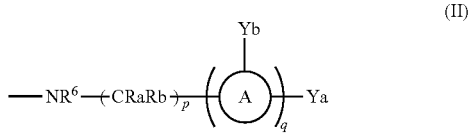

wherein:
R³ is a hydrogen atom or a $C_{1-4}$ alkyl group;
R⁴, R⁵ and R⁶ are the same or different and each is independently a hydrogen atom, a $C_{1-8}$ alkyl group, a carboxyl $C_{1-8}$ alkyl group or a $C_{3-8}$ alkenyl group, or R⁴ and R⁵ together with the nitrogen atom to which they are bonded form a $C_{3-9}$ heterocycle, wherein said $C_{1-8}$ alkyl group, said $C_{3-8}$ alkenyl group and said $C_{3-9}$ heterocycle may be substituted with one or more substituents;
Ra and Rb are the same or different and each is independently a hydrogen atom, a $C_{1-8}$ alkyl group, a carboxyl $C_{1-8}$ alkyl group, a carboxyl group, an aryl group, a $C_{3-6}$ heterocyclic group containing 1 to 4 heteroatoms selected from the group consisting of O, N and S, or a $C_{3-8}$ cycloalkyl group, or Ra and Rb together with the atom(s) to which they are bonded form a $C_{3-8}$ cycloalkane ring or a $C_{3-9}$ heterocycle containing 1-4 heteroatoms selected from the group consisting of O, N and S, wherein said $C_{1-8}$ alkyl group, said aryl group, said $C_{3-8}$ cycloalkyl group, said $C_{3-8}$ cycloalkane ring and said $C_{3-9}$ heterocycle may be substituted with one or more substituents;
Ring A is an arene, a $C_{3-6}$ heterocycle containing 1-4 heteroatoms selected from the group consisting of O, N and S, or a $C_{3-8}$ cycloalkane ring;
Ya is a hydrogen atom, a halogen atom, a carboxyl group, a hydroxyl group, a carbonyl group, a carboxyl $C_{1-3}$ alkyl group or a sulfo group;
Yb is a hydrogen atom, a halogen atom, a carboxyl group, a hydroxyl group, a carbonyl group, a carboxyl $C_{1-3}$ alkyl group, a nitro group, a cyano group or a $C_{1-3}$ alkoxyl group;
p is 0, 1, 2, 3 or 4;
q is 0 or 1; and
R⁷ is a hydrogen atom, a halogen atom or a nitro group;
with the proviso that when R¹ and R² are both methyl groups, then neither of R⁴ nor R⁵ is an ethyl group substituted with two carboxyl groups, and when R¹ and R² are both methyl groups, then the group represented by formula (II) is not a group represented by formula:

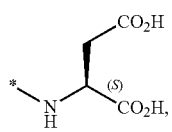

or a pharmaceutically acceptable salt thereof,
to a subject in need thereof.
The present invention also provides the above-mentioned method, wherein X is —NR⁴R⁵ or a group represented by formula (II), wherein R⁴, R⁵ and R⁶ are each independently a hydrogen atom or a $C_{1-8}$ alkyl group.

The present invention also provides the above-mentioned method, wherein X is —NR⁴R⁵, wherein R⁴ and R⁵ together with the nitrogen atom to which they are bonded form a $C_{3-9}$ heterocycle substituted by a hydrogen atom, a halogen atom, a carboxyl group, a carboxyl $C_{1-3}$ alkyl group or a hydroxyl group.

The present invention also provides the above-mentioned method, wherein X is a group represented by formula (II), wherein p=1 or 2, and q=0.

The present invention also provides the above-mentioned method, wherein X is a group represented by formula (II), wherein p=0 and q=1.

The present invention also provides the above-mentioned method, wherein X is a group represented by formula (II), wherein p=1, q=1, and Ra and Rb are the same or different and each is independently a hydrogen atom or a $C_{1-8}$ alkyl group, or Ra and Rb together with the atom(s) to which they are bonded form a $C_{3-8}$ cycloalkane ring, wherein said $C_{1-8}$ alkyl group and said $C_{3-8}$ cycloalkane ring may substituted with a group selected from the group consisting of a hydrogen atom, a carboxyl group, a carbamoyl group, a hydroxyl group, a phenyl group and a $C_{3-8}$ cycloalkyl group.

The present invention also provides the above-mentioned method, wherein R¹ and R² are the same or different and each is independently a methyl group, an ethyl group or a propyl group, or R¹ and R² together with the carbon atom to which they are bonded form a cyclobutane ring or a cyclopentane ring.

The present invention also provides the above-mentioned method, wherein X is a group represented by formula (II), wherein q=1, and Ring A is a benzene ring, a pyridine ring, or a $C_{1-6}$ heterocycle containing 1-4 oxygen atoms.

The present invention also provides the above-mentioned method, wherein X is a group represented by formula (II), wherein q=1, Ya is a halogen atom, a carboxyl group, a carboxyl $C_{1-3}$ alkyl group, a hydroxyl group, a sulfo group or a carbonyl group, and Yb is a hydrogen atom, a halogen atom, a carboxyl group or a hydroxyl group.

The present invention also provides the above-mentioned method, wherein X is —NR⁴R⁵, wherein when R⁴ or R⁵ has substituent(s), said substituent is selected from the group consisting of a halogen atom, a carboxyl group, a hydroxyl group, a carboxyl $C_{1-3}$ alkyl group, a $C_{3-8}$ alkenyl group, a carbamoyl group, a phenyl group, an amino group, a sulfo group, a cyano group, a $C_{3-8}$ cycloalkyl group, and a $C_{1-8}$ heterocyclic group containing 1 to 4 heteroatoms selected from the group consisting of O, N and S.

The present invention also provides the above-mentioned method, wherein X is a group represented by formula (II), wherein, when Ra or Rb has substituent(s), said substituent is selected from the group consisting of a carboxyl group, a hydroxyl group, a phenyl group, an amino group, a methylthio group, a thiol group, a carbamoyl group, a guanidino group, a $C_{3-8}$ cycloalkyl group, and a $C_{1-8}$ heterocyclic group containing 1-4 heteroatoms selected from the group consisting of O, N and S.

The present invention also provides the above-mentioned method, wherein, said compound represented by formula (I) is a compound represented by any of the following formulae:

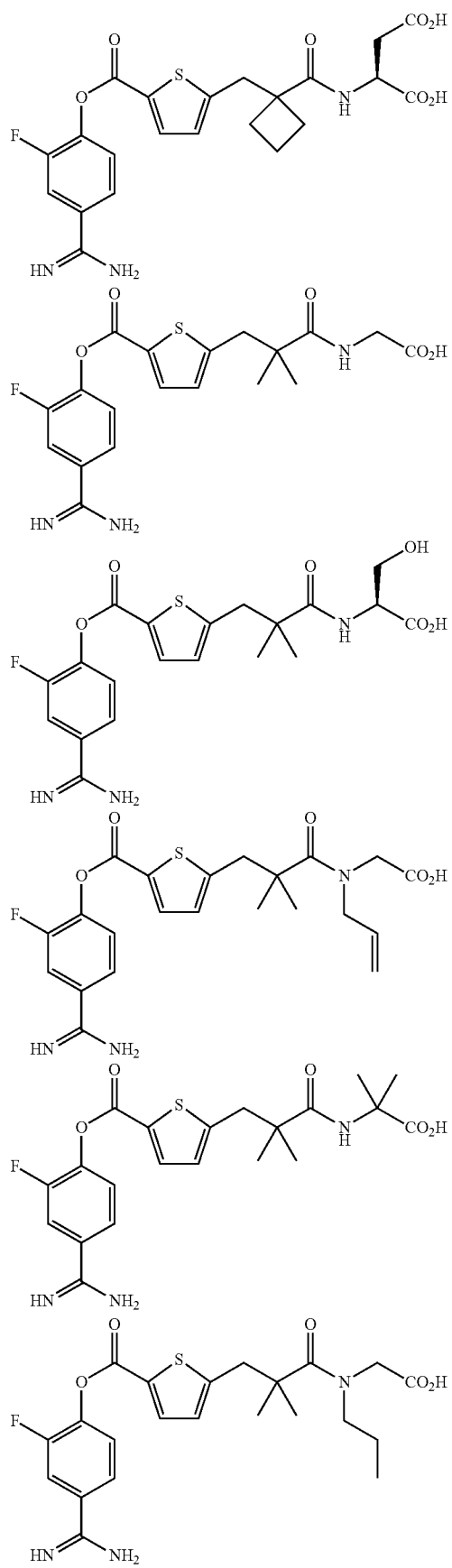
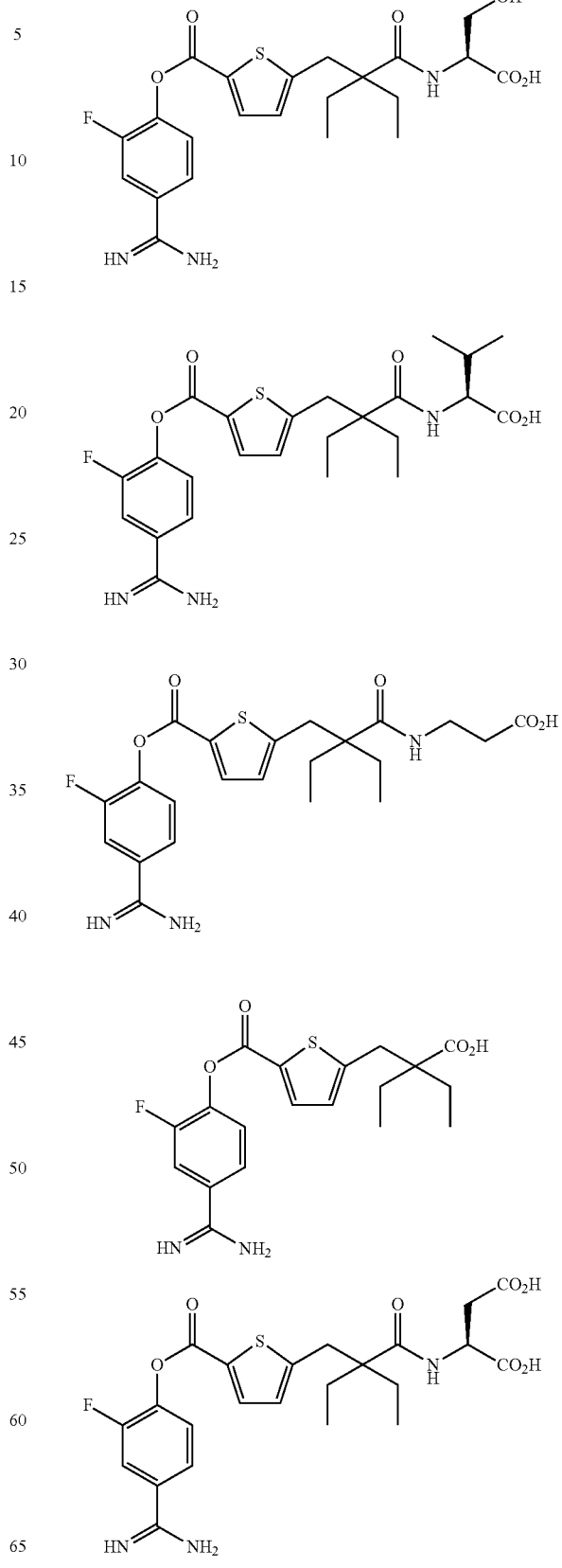

-continued
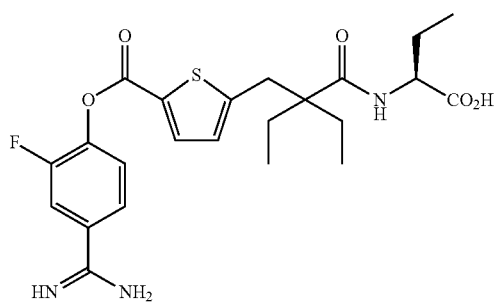
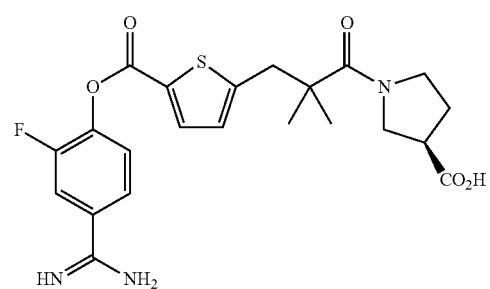
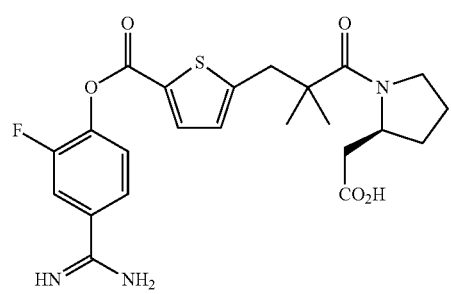
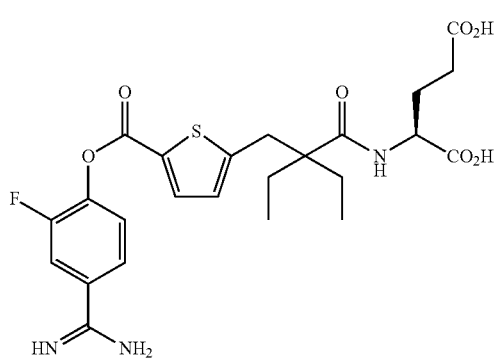
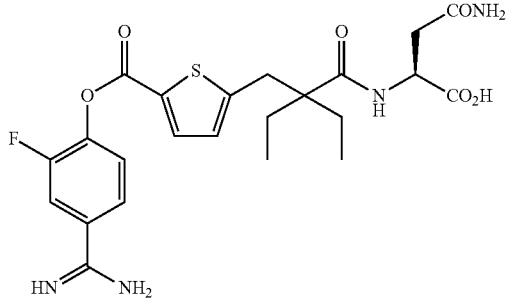
-continued
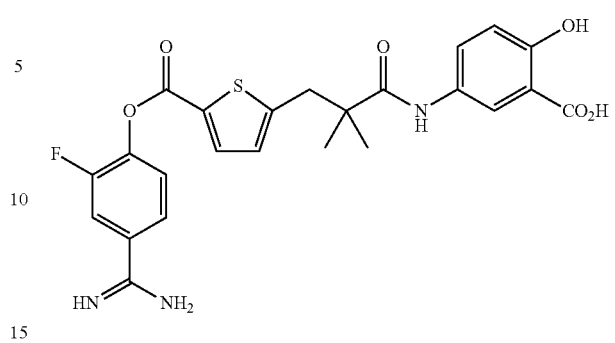
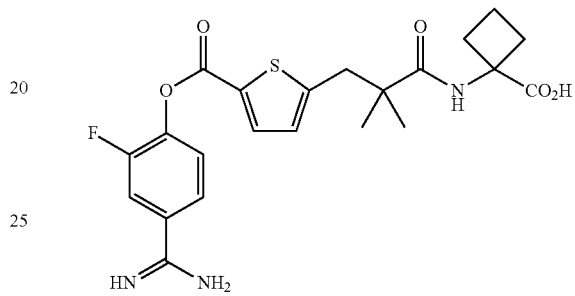
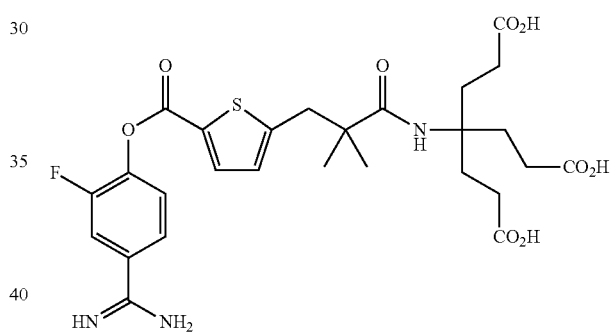
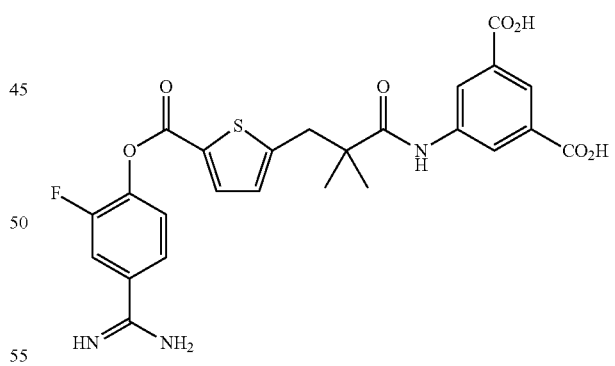
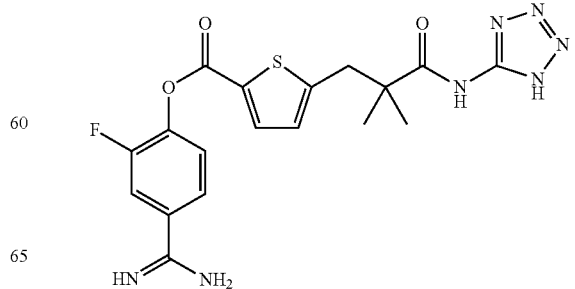

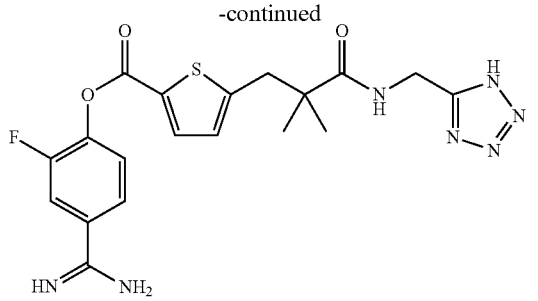

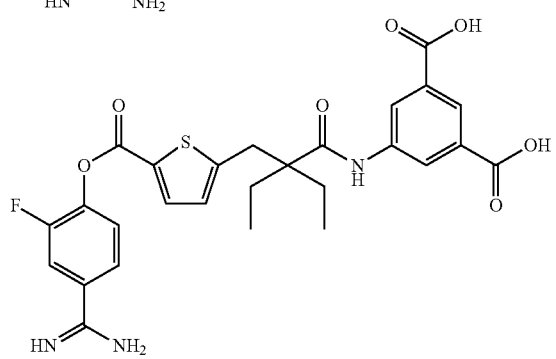

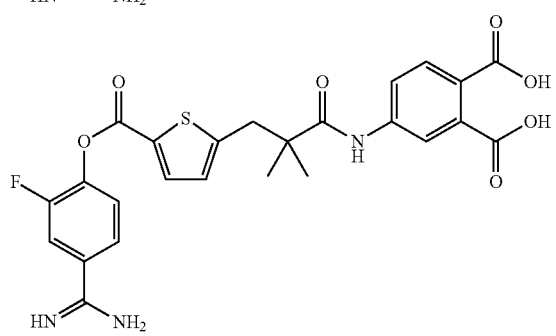

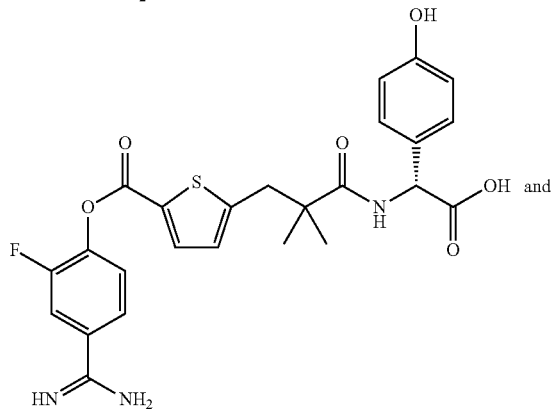

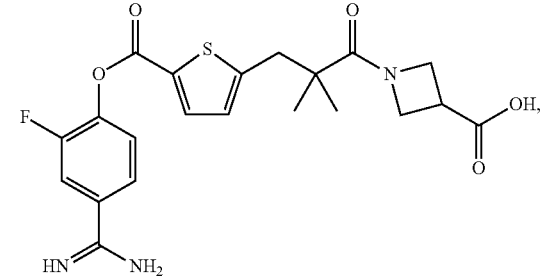

The present invention also provides the above-mentioned method, wherein said compound represented by formula (I) is a compound represented by any of the following formulae:

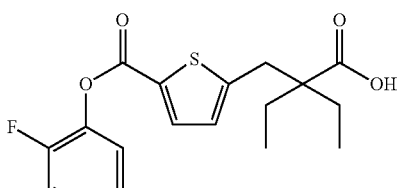

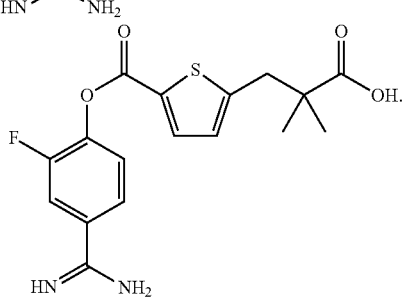

The compound of the present invention has a blood glucose elevation suppressing action and can be preferably used as a drug for the treatment or prophylaxis of diabetes.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein.

DETAILED DESCRIPTION OF THE PREFERRED EMBODIMENTS

Figure 1:
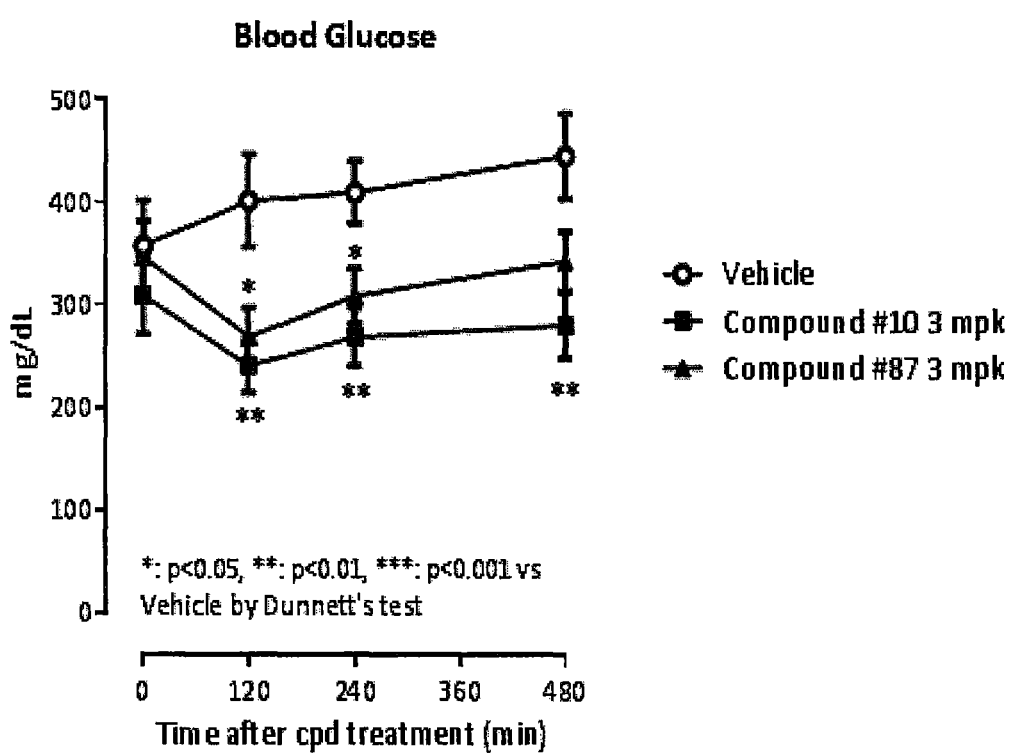
FIG. 1 shows blood glucose levels at 0, 2, 4, and 8 hours after dosing compounds of No. 10 and 87, and the vehicle at the dose of 3 mg/kg in KK-A$^y$/JCL mice.

The present invention is explained in detail in the following.

In the present specification, the phrase "may be substituted" or "optionally having substituent(s)" means "being substituted or unsubstituted". Unless otherwise specified, the position and number of the substituents may be any, and are not particularly limited. When substituted by two or more substituents, the substituents may be the same or different. Examples of the substituent include a nitro group, a halogen atom, a cyano group, a hydroxyl group, a sulfanyl group, an amino group, a guanidino group, a formyl group, a phenyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group and the like.

In the present specification, examples of the substituent of the "aryl group optionally having substituent(s)" and "heterocyclic group optionally having substituent(s)" include a nitro group, a halogen atom, a cyano group, a hydroxyl group, a sulfanyl group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group and the like.

The "cyclic amino group" in the present specification is a saturated or unsaturated cyclic amino group having a carbon number of 2 to 7, which may contain one or more hetero atoms in the ring, such as a nitrogen atom, an oxygen atom, a sulfur atom and the like. For example, a pyrrolidinyl group, a pyrrolinyl group, a piperidyl group, a morpholinyl group, a piperazinyl group, a thiomorpholinyl group, a piperidinonyl group, a piperazinonyl group and the like can be mentioned.

The term "lower" in, for example, a lower alkyl group in the present specification indicates that the group has 1 to 6 carbon atoms, preferably 1 to 4 carbon atoms, and more preferably, 1 to 3 carbon atoms, unless otherwise specified.

The "alkyl group" is a linear or branched or cyclic alkyl group (in particular, a linear or branched alkyl group), preferably, having a carbon number of 1 to 10, more preferably, having a carbon number of 1 to 8 (i.e., the "$C_{1-8}$ alkyl"). For example, a methyl group, an ethyl group, an n-propyl group, an n-butyl group, an n-pentyl group, an n-hexyl group, an isopropyl group, an isobutyl group, a sec-butyl group, a tert-butyl group, an isopentyl group, a tert-pentyl group, a neopentyl group, a 2-pentyl group, a 3-pentyl group, a 2-hexyl group, a cyclopropyl group, a cyclobutyl group, a cyclopentyl group, a cyclohexyl group and the like can be mentioned. Examples of the "$C_{1-4}$ alkyl group" include an alkyl group with 1 to 4 carbon atoms, from among the above-mentioned alkyl group. Examples of the "$C_{1-3}$ alkyl group" include an alkyl group with 1 to 3 carbon atoms, from among the above-mentioned alkyl group. Examples of the "$C_{3-4}$ alkyl group" include an alkyl group with 3 or 4 carbon atoms, from among the above-mentioned alkyl group.

The "carboxyl $C_{1-8}$ alkyl group" is the $C_{1-8}$ alkyl substituted by one or more (e.g., 1 to 3, preferably 1 or 2, more preferably one) carboxyl groups. The "carboxyl $C_{1-3}$ alkyl" is the $C_{1-3}$ alkyl group substituted by one or more (e.g., 1 to 3, preferably 1 or 2, more preferably one) carboxyl groups.

The "cycloalkyl group" is a cyclic alkyl group, preferably, having a carbon number of 3 to 10. Examples of the "cycloalkyl" include a cyclopropyl group, a cyclobutyl group, a cyclopentyl group, a cyclohexyl group and the like. Examples of the "$C_{3-8}$ cycloalkyl group" include a cycloalkyl group with 3 to 8 carbon atoms, from among the above-mentioned cycloalkyl group.

The "cycloalkane ring" is a ring moiety in a cycloalkyl group, preferably, having a carbon number of 3 to 10. Examples of the "cycloalkane ring" include a cyclopropane ring, a cyclobutane ring, a cyclopentane ring, a cyclohexane ring and the like. Examples of the "$C_{3-8}$ cycloalkane ring" include a cycloalkane ring with 3 to 8 carbon atoms, from among the above-mentioned cycloalkane ring. Examples of the "$C_{3-5}$ cycloalkane ring" include a cycloalkane ring with 3 to 5 carbon atoms, from among the above-mentioned cycloalkane ring.

The "alkenyl group" is a linear or branched alkenyl group, preferably, having a carbon number of 2 to 10, which includes each isomer. For example, a vinyl group, an allyl group, a propenyl group, a butenyl group, a pentenyl group, a hexenyl group and the like can be mentioned. Examples of the "$C_{3-8}$ alkenyl group" include an alkenyl group with 3 to 8 carbon atoms, from among the above-mentioned alkenyl group. Examples of the "$C_{2-4}$ alkenyl group" include an alkenyl group with 2 to 4 carbon atoms, from among the above-mentioned alkenyl group.

The "cycloalkenyl group" is a cyclic alkenyl group preferably, having a carbon number of 3 to 10. For example, a cyclopropenyl group, a cyclobutenyl group a cyclopentenyl group, a cyclohexenyl group and the like can be mentioned. Examples of the "$C_{3-8}$ cycloalkenyl group" include a cycloalkenyl group with 3 to 8 carbon atoms, from among the above-mentioned cycloalkenyl group.

The "$C_{3-8}$ cycloalkene ring" is a ring moiety in a cyclic alkenyl group having a carbon number of 3 to 8. For example, a cyclopropene ring, a cyclobutene ring, a cyclopentene ring, a cyclohexene ring and the like can be mentioned.

The "alkynyl group" is a linear or branched alkynyl group having a carbon number of 2 to 10, which includes each isomer. For example, an ethynyl group, a 1-propynyl group, a 2-propynyl group, a 2-butynyl group, a 3-butynyl group, a pentynyl group and the like can be mentioned.

Examples of the "halogen atom" include a fluorine atom, a chlorine atom, a bromine atom, an iodine atom and the like.

The "acyl group" is an acyl group having a linear or branched or cyclic alkyl group or alkenyl group having a carbon number of 1 to 10, preferably, 1 to 8, more preferably, 1 to 6. For example, an acetyl group, a propionyl group, a butyryl group, an isobutyryl group, a valeryl group, an isovaleryl group, a pivaloyl group, a hexanoyl group, an acryloyl group, a methacryloyl group, a crotonoyl group, an isocrotonoyl group, a cyclopropanoyl group, a cyclobutanoyl group, a cyclopentanoyl group, a cyclohexanoyl group and the like can be mentioned.

The "alkoxyl group" is an alkoxyl group having a linear or branched or cyclic alkyl group having a carbon number of 1 to 10, preferably, 1 to 8, more preferably, 1 to 6, and further more preferably 1 to 3 (i.e., the "$C_{1-3}$ alkoxyl group"). For example, a methoxy group, an ethoxy group, an n-propoxy group, an n-butoxy group, an n-pentyloxy group, an n-hexyloxy group, an isopropoxy group, an isobutoxy group, a sec-butoxy group, a tert-butoxy group, a cyclopropyloxy group, a cyclobutyloxy group, a cyclopentyloxy group and a cyclohexyloxy group can be mentioned. Examples of "$C_{1-3}$ alkoxyl group" include an alkoxyl group with 1 to 3 carbon atoms, from among the above-mentioned alkoxyl group.

The "alkylthio group" is an alkylthio group having a linear or branched or cyclic alkyl group having a carbon number of 1 to 10, preferably, 1 to 8, more preferably, 1 to 6. For example, a methylthio group, an ethylthio group, an n-propylthio group, an isopropylthio group, an n-butylthio group, an isobutylthio group, a sec-butylthio group, a tert-butylthio group, a cyclopropylthio group, a cyclobutylthio group, a cyclopentylthio group, a cyclobutylthio group and the like can be mentioned.

The "alkylamino group" is an amino group mono- or di-substituted by the aforementioned "alkyl group", preferably, "lower alkyl group". For example, a methylamino group, an ethylamino group, a propylamino group, an isopropylamino group, a dimethylamino group, a diethylamino group, a dipropylamino group, a diisopropylamino group, an ethylmethylamino group and the like can be mentioned.

The "acyloxy group" is a group wherein an oxygen atom is bonded to the carbon of the carbonyl moiety of the aforementioned "acyl group", preferably, "lower acyl group". For example, an acetyloxy group, a propionyloxy group, a butyryloxy group, an isobutyryloxy group, a valeryloxy group, an isovaleryloxy group, a pivaloyloxy group, a hexanoyloxy group, an acryloyloxy group, a methacryloyloxy group, a crotonoyloxy group, an isocrotonoyloxy group and the like can be mentioned.

The "acylamino group" is a group wherein a nitrogen atom is bonded to the carbon of the carbonyl moiety of the aforementioned "acyl group", preferably, "lower acyl group". For example, an acetylamino group, a propionylamino group, a butyrylamino group, an isobutyrylamino group, a valerylamino group, an isovalerylamino group, a pivaloylamino group, a hexanoylamino group, an acryloylamino group, a methacryloylamino group, a crotonoylamino group, an isocrotonoylamino group and the like can be mentioned.

The "alkoxycarbonyl group" is a carbonyl group having the aforementioned "alkoxyl group", preferably, "lower alkoxyl group" such as $C_{1-3}$ alkoxyl group For example, a methoxycarbonyl group, an ethoxycarbonyl group, a propoxycarbonyl group, an isopropoxycarbonyl group, an n-butoxycarbonyl group, an isobutoxycarbonyl group, a sec-butoxycarbonyl group, a tert-butoxycarbonyl group and the like can be mentioned. Examples of the "$C_{1-3}$ alkoxy-carbonyl group" include a carbonyl group with the above-mentioned $C_{1-3}$ alkoxyl group, from among the above-mentioned alkoxycarbonyl group.

The "alkylcarbamoyl group" is a group wherein a nitrogen atom of the aforementioned "alkylamino group" or "cyclic amino group", and a carbon atom of the carbonyl group are bonded. For example, an N-methylcarbamoyl group, an N-ethylcarbamoyl group, an N,N-dimethylcarbamoyl group, a 1-pyrrolidinylcarbonyl group, a 1-piperidylcarbonyl group, a 4-morpholinylcarbonyl group, and the like can be mentioned. Examples of the "$C_{1-3}$ alkyl-carbamoyl group" include an alkylcarbamoyl group with 1 to 3 carbon atoms in the "alkylamino group" or the "cyclic amino group", from among the above-mentioned alkylcarbamoyl group.

The "alkylsulfonylamino group" is a group wherein a nitrogen atom is bonded to a sulfonyl group wherein the aforementioned "alkyl group", preferably, "lower alkyl group" is bonded to a sulfur atom. For example, a methylsulfonylamino group, an ethylsulfonylamino group, a propylsulfonylamino group, an isopropylsulfonylamino group, a butylsulfonylamino group, an isobutylsulfonylamino group and the like can be mentioned.

The "arylsulfonylamino group" is a group wherein a nitrogen atom is bonded to a sulfur atom of a sulfonyl group substituted by an aryl group. For example, a phenylsulfonylamino group, a naphthylsulfonylamino group and the like can be mentioned.

Examples of the "aryl group" include an aryl group having a carbon number of 6 to 14 such as a phenyl group, a naphthyl group and the like, preferably, a phenyl group.

The "arene" is a ring moiety in the aryl group having a carbon number of 6 to 14. Examples of "arene" include a benzene ring, a naphthalene ring and the like, preferably, a benzene ring.

The "heterocyclic group" is a 3- to 14-membered monocyclic to tricyclic heterocyclic group containing, as a ring atom, 1 to 4 hetero atoms selected from an oxygen atom, a sulfur atom and a nitrogen atom. Any carbon atom as a ring atom may be substituted by an oxo group, and a sulfur atom or a nitrogen atom may be oxidized to form an oxide. In addition, it may be condensed with a benzene ring. For example, a pyridyl group, a pyridazinyl group, a pyrimidinyl group, a pyrazinyl group, a furyl group, a thienyl group, a pyrrolyl group, an isoxazolyl group, an oxazolyl group, an isothiazolyl group, a thiazolyl group, a pyrazolyl group, an imidazolyl group, an oxadiazolyl group, a thiadiazolyl group, a triazolyl group, a tetrazolyl group, a benzofuranyl group, a benzothienyl group, an indolyl group, an isoindolyl group, a benzoxazolyl group (=a benzooxazolyl group), a benzothiazolyl group, a benzimidazolyl group (=a benzoimidazolyl group), an indazolyl group, a benzisoxazolyl group, a benzisothiazolyl group, a benzofurazanyl group, a benzothiadiazolyl group, a purinyl group, a quinolinyl group, an isoquinolyl group, a cinnolinyl group, a phthalazinyl group, a quinazolinyl group, a quinoxalinyl group, a pteridinyl group, an imidazooxazolyl group, an imidazothiazolyl group, an imidazoimidazolyl group, a dibenzofuryl group, a dibenzothienyl group, a carbazolyl group, an acridinyl group, a pyrrolidinyl group, a pyrazolidinyl group, an imidazolidinyl group, a pyrrolinyl group, a pyrazolinyl group, an imidazolinyl group, a tetrahydrofuryl group, a tetrahydrothiophenyl group, a thiazolidinyl group, a piperidyl group, a piperazinyl group, a quinuclidinyl group, a tetrahydropyranyl group, a tetrahydrothiopyranyl group, a morpholinyl group, a thiomorpholinyl group, a dioxolanyl group, a homopiperidyl group, a homopiperazinyl group, an indolinyl group, an isoindolinyl group, a chromanyl group, an isochromanyl group, a tetrahydronaphthyridinyl group, an azaindolyl group, a tetrahydroisoquinolinyl group, an aziridinyl group, an azetidinyl group, a dihydropyridyl group and the like can be mentioned. Preferably, a thiadiazolyl group, an imidazolyl group, a 1H-tetrazolyl group, a piperidyl group, a piperazinyl group, a thiazolidinyl group, a tetrahydroisoquinolinyl group, an aziridinyl group, an azetidinyl group, a tetrahydrofuryl group, a dihydropyridyl group and the like can be mentioned. Examples of the "$C_{3-8}$ heterocyclic group" include a heterocyclic group with 3 to 8 carbon atoms as a ring atom, from among the above-mentioned heterocyclic group. Examples of the "$C_{3-6}$ heterocyclic group" include a heterocyclic group with 3 to 6 carbon atoms as a ring atom, from among the above-mentioned heterocyclic group. Examples of the "$C_{1-8}$ heterocyclic group" include a heterocyclic group with 1 to 8 carbon atoms as a ring atom, from among the above-mentioned heterocyclic group.

The "heterocycle" is a 3- to 14-membered monocyclic to tricyclic heterocycle containing, as a ring atom, 1 to 4 hetero atoms selected from an oxygen atom, a sulfur atom and a nitrogen atom. Any carbon atom as a ring atom may be substituted by an oxo group, and a sulfur atom or a nitrogen atom may be oxidized to form an oxide. In addition, it may be condensed with a benzene ring. For example, a pyridine ring, a pyridazine ring, a pyrimidine ring, a pyrazine ring, a furan ring, a thiophene ring, a pyrrole ring, an isoxazole ring, an oxazole ring, an isothiazole ring, a thiazole ring, a pyrazole ring, an imidazole ring, an oxadiazole ring, a thiadiazole ring, a triazole ring, a tetrazole ring, a benzofuran ring, a benzothiophene ring, an indole ring, an isoindole ring, a benzoxazole ring (=a benzooxazole ring), a benzothiazole ring, a benzimidazole ring (=a benzoimidazole ring), an indazole ring, a benzisoxazole ring, a benzisothiazole ring, a benzofurazane ring, a benzothiadiazole ring, a purine ring, a quinoline ring, an isoquinoline ring, a cinnoline ring, a phthalazine ring, a quinazoline ring, a quinoxaline ring, a pteridine ring, an imidazooxazole ring, an imidazothiazole ring, an imidazoimidazole ring, a dibenzofuran ring, a dibenzothiophene ring, a carbazole ring, an acridine ring, a pyrrolidine ring, a pyrazolidine ring, an imidazolidine ring, a pyrroline ring, a pyrazoline ring, an imidazoline ring, a tetrahydrofuran ring, a tetrahydrothiophene ring, a thiazolidine ring, a piperidine ring, a piperazine ring, a quinuclidine ring, a tetrahydropyrane ring, a tetrahydrothiopyrane ring, a morpholine ring, a thiomorpholine ring, a dioxolane ring, a homopiperidine ring, a homopiperazine ring, an indoline ring, an isoindoline ring, a chromane ring, an isochromane ring, a tetrahydronaphthyridine ring, an azaindole ring, a tetrahydroisoquinoline ring, an aziridine ring, an azetidine ring, a dihydropyridine ring and the like can be mentioned. Preferably, a thiadiazole ring, an imidazole ring, a tetrazole ring, a piperidine ring, a piperazine ring, a thiazolidine ring, a tetrahydroisoquinoline ring, an aziridine ring, an azetidine ring, a tetrahydrofuran ring, a dihydropyridine ring and the like can be mentioned. Examples of the "$C_{2-9}$ heterocycle" include a heterocycle with 2 to 9 carbon atoms as a ring atom, from among the above-mentioned heterocycle. Examples of the "$C_{3-9}$ heterocycle" include a heterocycle with 3 to 9 carbon atoms as a ring atom, from among the above-mentioned heterocycle. Examples of the "$C_{3-6}$ heterocycle" include a heterocycle with 3 to 6 carbon atoms as a ring atom, from among the above-mentioned heterocycle. Examples of the "$C_{1-6}$ heterocycle" include a heterocycle with 1 to 6 carbon atoms as a ring atom, from among the above-mentioned heterocycle.

The "serine protease" in the present specification is a protease having, as a catalytic residue, a serine residue having nucleophilicity. For example, trypsin, chymotrypsin, elastase, enteropeptidase, kallikrein, thrombin, factor Xa, and tryptase, and the like can be mentioned. In addition, the term "serine protease inhibition" in the present specification means a decrease or disappearance of the aforementioned serine protease activity. Preferably, it is an inhibition of the activity of intestinal serine proteases such as trypsin, enteropeptidase, chymotrypsin, elastase and the like, particularly preferably inhibition of trypsin and enteropeptidase activities.

The serine protease inhibitor of the present invention is a dual inhibitor that simultaneously inhibits at least trypsin and enteropeptidase.

The diabetes in the present specification means type I diabetes mellitus and type II diabetes mellitus, with preference given to type II diabetes mellitus.

In the present invention, the compound represented by the formula (I) or a pharmaceutically acceptable salt thereof is preferably as follows.

In the formula (I), $R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring. Preferably, $R^1$ and $R^2$ are the same or different from each other and each is independently a linear or branched $C_{1-4}$ alkyl group (specifically, a methyl group, an ethyl group and the like), or $R^1$ and $R^2$ together with the carbon atom to which they are bonded form a $C_{3-5}$ cycloalkane ring (specifically, a cyclobutane ring, a cyclopentane ring and the like). More preferably $R^1$ and $R^2$ are independently a $C_{1-3}$ alkyl group (specifically, a methyl group, an ethyl group and the like), particularly extremely preferably a methyl group and an ethyl group and the like.

In other aspect, it is also preferable that $R^1$ and $R^2$ are the same.

In other aspect, $R^1$ and $R^2$ are, preferably, both a methyl group or an ethyl group. In other aspect, $R^1$ and $R^2$ are, preferably, both methyl groups. In other aspect, $R^1$ and $R^2$ are, preferably, both ethyl groups.

In other aspect, $R^1$ and $R^2$ are, preferably, the same or different and each is independently a methyl group, an ethyl group or a propyl group, or $R^1$ and $R^2$ together with the carbon atom to which they are bonded form a cyclobutane ring or a cyclopentane ring.

In the formula (I), X is —$OR^3$, —$NR^4R^5$ or a group represented by the formula (II):

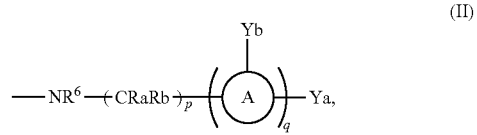

preferably, —$NR^4R^5$ or a group represented by the formula (II), more preferably, a group represented by the formula (II). In other aspect, X is more preferably —$NR^4R^5$. In other aspect, X is preferably —$OR^3$, more preferably —OH.

In other aspect, X is preferably —OH, —$NR^4R^5$ or a group represented by the formula (II), and each of —$NR^4R^5$ and the group represented by the formula (II) has one carboxyl group, particularly, X is —OH, from the aspect of stability and few side effects.

In the group —$OR^3$, $R^3$ is a hydrogen atom or a $C_{1-4}$ alkyl group, preferably a hydrogen atom (i.e., —$OR^3$ is preferably —OH).

In the group —$NR^4R^5$, $R^4$ and $R^5$ are the same or different and each is independently a hydrogen atom, a $C_{1-8}$ alkyl group, a carboxyl $C_{1-8}$ alkyl group or a $C_{3-8}$ alkenyl group, or $R^4$ and $R^5$ together with the nitrogen atom to which they are bonded form a $C_{3-9}$ heterocycle, wherein said $C_{1-8}$ alkyl group, said $C_{3-8}$ alkenyl group and said $C_{3-9}$ heterocycle may be substituted with one or more substituents.

In other aspect, in the group —$NR^4R^5$, $R^4$ and $R^5$ are the same or different and each is independently a hydrogen atom, a $C_{1-8}$ alkyl group, a carboxyl $C_{1-8}$ alkyl group or a $C_{3-8}$ alkenyl group, or $R^4$ and $R^5$ together with the nitrogen atom to which they are bonded form a $C_{2-9}$ heterocycle, wherein said $C_{1-8}$ alkyl group, said carboxyl $C_{1-8}$ alkyl group, said $C_{3-8}$ alkenyl group and said $C_{2-9}$ heterocycle may be substituted with one or more substituents.

Preferably $R^4$ and $R^5$ are the same or different and each is independently a hydrogen atom, a $C_{1-8}$ alkyl group, a carboxyl $C_{1-8}$ alkyl group or a $C_{3-8}$ alkenyl group, wherein said $C_{1-8}$ alkyl group, said carboxyl $C_{1-8}$ alkyl group and said $C_{3-8}$ alkenyl group may be substituted with one or more substituents.

More preferably, $R^4$ and $R^5$ are the same or different and each is independently a hydrogen atom, a $C_{1-3}$ alkyl group or a carboxyl $C_{1-3}$ alkyl group, wherein said $C_{1-3}$ alkyl group and said carboxyl $C_{1-3}$ alkyl group may be substituted with one or more substituents.

In other aspect, preferably,
$R^4$ is
(1) a carboxyl $C_{1-8}$ alkyl group optionally substituted by 1 to 3 substituents selected from
  (a) a hydroxyl group,
  (b) an aryl group (specifically, a phenyl group and the like),
  (c) a $C_{3-8}$ cycloalkyl group (specifically, a cyclohexyl group and the like),
  (d) a carbamoyl group,
  (e) an amino group,
  (f) an aryl group (specifically, a phenyl group and the like) optionally substituted by a hydroxyl group,
  (g) a $C_{1-3}$ alkyl-carbamoyl group (specifically, an N-methylcarbamoyl group and the like) optionally substituted by a carboxyl group, and
  (h) a $C_{1-8}$ heterocyclic group (specifically, a 1H-tetrazolyl group and the like), or
(2) a $C_{1-8}$ alkyl group optionally substituted by 1 to 3 substituents selected from
  (a) a sulfo group,
  (b) a cyano group, (c) a $C_{1-8}$ heterocyclic group (specifically, a 1H-tetrazolyl group and the like), and
(d) an aryl group (specifically, a phenyl group and the like) optionally substituted by a carboxyl group, and $R^5$ is a hydrogen atom, a $C_{1-3}$ alkyl group optionally substituted by a $C_{3-8}$ cycloalkyl group (specifically, a cyclopropyl group and the like), or a $C_{3-8}$ alkenyl group; or $R^4$ and $R^5$ together with the nitrogen atom to which they are bonded form a $C_{2-9}$ heterocycle substituted by 1 to 3 substituents selected from
(1) a halogen atom (specifically, a fluorine atom and the like),
(2) a hydroxyl group,
(3) a carboxyl group, and
(4) a carboxyl $C_{1-3}$ alkyl group (specifically, a carboxylmethyl and group the like).

More preferably,
$R^4$ is
(1) a carboxyl $C_{1-8}$ alkyl group optionally substituted by 1 to 3 substituents selected from
(a) a hydroxyl group,
(b) an aryl group (specifically, a phenyl group and the like),
(c) a $C_{3-8}$ cycloalkyl group (specifically, a cyclohexyl group and the like),
(d) a carbamoyl group,
(e) an amino group,
(f) an aryl group (specifically, a phenyl group and the like) optionally substituted by a carboxyl group or a hydroxyl group,
(g) a $C_{1-3}$ alkyl-carbamoyl group (specifically, an N-methylcarbamoyl group and the like) optionally substituted by a carboxyl group, and
(h) a $C_{1-8}$ heterocyclic group (specifically, a 1H-tetrazolyl group and the like), or
(2) a $C_{1-8}$ alkyl group optionally substituted by 1 to 3 substituents selected from
(a) a sulfo group,
(b) a cyano group, and
(c) a $C_{1-8}$ heterocyclic group (specifically, a 1H-tetrazolyl group and the like), and $R^5$ is a hydrogen atom, a $C_{1-3}$ alkyl group optionally substituted by a $C_{3-8}$ cycloalkyl group (specifically, a cyclopropyl group and the like), or a $C_{3-8}$ alkenyl group.

In other aspect, preferably, $R^4$ is a hydrogen atom, a methyl group, an ethyl group, a propyl group or a propenyl group, and $R^5$ is a $C_{3-4}$ alkyl group having 1 or 2 substituent(s) selected from the group of a carboxyl and hydroxyl group.

In other aspect, preferably, $R^4$ is a hydrogen atom, a methyl group, an ethyl group, a propyl group or a propenyl group, and $R^5$ is a $C_{1-6}$ alkyl group having 1 or 2 substituent(s) selected from the group of a carboxyl group, a hydroxyl group, an amino group and a carbamoyl group.

In other aspect, preferably, $R^4$ and $R^5$ are each independently a hydrogen atom or a $C_{1-8}$ alkyl group.

In other aspect, preferably, $R^4$ and $R^5$ together with the nitrogen atom to which they are bonded form a $C_{2-9}$ heterocycle substituted by a halogen atom (specifically, a fluorine atom and the like), a carboxyl group, a carboxyl $C_{1-3}$ alkyl group (specifically, a carboxylmethyl group and the like) or a hydroxyl group.

As the $C_{1-8}$ alkyl group or the $C_{1-3}$ alkyl group for $R^4$ and $R^5$, a methyl group, an ethyl group, a propyl group and the like can be mentioned.

As the carboxyl $C_{1-8}$ alkyl for $R^4$ and $R^5$, a linear or branched carboxyl $C_{1-8}$ alkyl group such as a 1,2-dicarboxylethyl group, a carboxylmethyl group, a 1-carboxyl-1-methylethyl group, a 1-carboxyl-2-methylpropyl group, a 2-carboxylethyl group, a 1-carboxylethyl group, a 1,3-dicarboxylpropyl group, a 1-carboxylpropyl group, a 1-carboxylbutyl group, a 3-carboxylpropyl group, a 1-(carboxylmethyl)-2-methylpropyl group, a 4-carboxylbutyl group, a 1,1-bis(2-carboxylethyl)-3-carboxylpropyl group and a 5-carboxylpentyl group; and a cyclic carboxyl $C_{3-8}$ alkyl group such as a 1-carboxylcyclopropyl group, a 1-carboxylcyclobutyl group, a 2-carboxylcyclohexyl group and a 3-carboxylcyclohexyl group can be mentioned.

As the carboxyl $C_{1-3}$ alkyl for $R^4$ and $R^5$, a linear or branched carboxyl $C_{1-3}$ alkyl group such as a 1,2-dicarboxylethyl group, a carboxylmethyl group, a 1-carboxyl-1-methylethyl group, a 2-carboxylethyl group, a 1-carboxylethyl group, a 1,3-dicarboxylpropyl group, a 1-carboxylpropyl group and a 3-carboxylpropyl group; and a 1-carboxylcyclopropyl group can be mentioned.

As the $C_{3-8}$ alkenyl group for $R^4$ and $R^5$, an allyl group and the like can be mentioned.

In one aspect, when the $C_{1-8}$ alkyl group, the carboxyl $C_{1-8}$ alkyl group, the $C_{3-8}$ alkenyl group, the $C_{1-3}$ alkyl group or the carboxyl $C_{1-3}$ alkyl group for $R^4$ or $R^5$ has one or more substituents, unless otherwise indicated, examples of the substituent include a nitro group, a halogen atom, a cyano group, a hydroxyl group, a sulfanyl group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally m having substituent(s), a cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group is optionally having substituent(s), an aralkylthio group optionally having substituent(s), a heterocyclic group optionally having substituent(s), a heterocyclyloxy group optionally having substituent(s), a heterocyclylthio group optionally having substituent(s), an oxo group and the like. A halogen atom, a hydroxyl group, a carboxyl group, a sulfo group, a cyano group, a phosphono group, a lower alkoxycarbonyl group, an aryl group optionally having substituent(s), a heterocyclic group optionally having substituent(s), an oxo group, and the like are preferable, and a hydroxyl group, a carboxyl group, a sulfo group, a lower alkoxycarbonyl group, and the like are particularly preferable. A carboxyl group, a hydroxyl group, a carboxyl $C_{1-3}$ alkyl group, a $C_{3-8}$ alkenyl group, a halogen atom, a carbamoyl group, a phenyl group, an amino group, a sulfo group, a cyano group, a $C_{3-8}$ cycloalkyl group, and a $C_{1-8}$ heterocyclic group containing 1-4 heteroatoms selected from the group consisting of O, N and S, and the like are also preferable. As for the $C_{1-8}$ heterocyclic group containing 1-4 heteroatoms, a 1H-tetrazolyl group, a 2,4-dioxo-1,3-thiazolidinyl group, and the like can be preferably mentioned. The number of the substituents is preferably 1 to 3, more preferably 1 or 2.

In other aspect, when the $C_{1-8}$ alkyl group, the carboxyl $C_{1-8}$ alkyl group, the $C_{3-8}$ alkenyl group, the $C_{1-3}$ alkyl group or the carboxyl $C_{1-3}$ alkyl group for $R^4$ or $R^5$ has one or more substituent, unless otherwise indicated, examples of the substituent include a lower alkylcarbamoyl group optionally having substituent(s), a hydroxyl group, a sulfo group, a cycloalkyl group, a carbamoyl group, an amino group, a cyano group, an aryl group optionally having substituent(s), a $C_{1-8}$ heterocyclic group and the like. Preferable examples of the substituent include a $C_{1-3}$ alkyl-carbamoyl group (specifically, an N-methylcarbamoyl group and the like) optionally substituted by a carboxyl group, a hydroxyl group, a sulfo group, a $C_{3-8}$ cycloalkyl group (specifically, a cyclopropyl group, a cyclohexyl group and the like), a carbamoyl group, an amino group, a cyano group, an aryl group (specifically, a phenyl group and the like) optionally substituted by a carboxyl group or a hydroxyl group, a $C_{1-8}$ heterocyclic group (specifically, a 1H-tetrazolyl group and the like) and the like. The number of the substituents is preferably 1 to 3, more preferably 1 or 2.

As the $C_{2-9}$ heterocycle or the $C_{3-9}$ heterocycle (i.e., a cyclic amino group) formed by $R^4$ and $R^5$ bonded to each other, an aziridine ring, an azetidine ring, a pyrrolidine ring, a piperidine ring, a tetrahydroisoquinoline ring and the like are preferable.

In one embodiment, when the $C_{2-9}$ heterocycle or the $C_{3-9}$ heterocycle formed by $R^4$ and $R^5$ bonded to each other has one or more substituents, unless otherwise indicated, examples of the substituent include a nitro group, a halogen atom, a cyano group, a hydroxyl group, a sulfanyl group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, an oxo group, and the like. A carboxyl group, a hydroxyl group, a carboxyl $C_{1-3}$ alkyl group, a $C_{3-43}$ alkenyl group, a halogen atom, a carbamoyl group, a phenyl group, an amino group, a sulfo group, and a $C_{1-8}$ heterocyclic group containing 1-4 heteroatoms selected from the group consisting of O, N and S, and the like are preferable. A hydroxyl group, a carboxyl group, a sulfo group, a phosphono group, a lower alkoxycarbonyl group, and the like are also preferable. The number of the substituents is preferably 1 to 3, more preferably 1 or 2. As for the $C_{1-8}$ heterocyclic group containing 1-4 heteroatoms, a 1H-tetrazolyl group, a 2,4-dioxo-1,3-thiazolidinyl group, and the like can be preferably mentioned.

In other aspect, when the $C_{2-9}$ heterocycle or the $C_{3-9}$ heterocycle formed by $R^4$ and $R^5$ bonded to each other has one or more substituents, unless otherwise indicated, examples of the substituent include a halogen atom, a hydroxyl group, a carboxyl group, a lower alkyl group optionally having substituent(s) and the like. Preferable examples of the substituent include a halogen atom (specifically, a fluorine atom and the like), a hydroxyl group, a carboxyl group, a carboxyl $C_{1-3}$ alkyl group (specifically, a carboxylmethyl group and the like) and the like. The number of the substituents is preferably 1 to 3, more preferably 1 or 2.

In the formula (II), $R^6$ is a hydrogen atom, a $C_{1-8}$ alkyl group, a carboxyl $C_{1-8}$ alkyl group or a $C_{3-8}$ alkenyl group, wherein said $C_{1-8}$ alkyl group, said carboxyl $C_{1-8}$ alkyl and said $C_{3-8}$ alkenyl group may be substituted with one or more substituents.

In other aspect, in the formula (II), $R^6$ is a hydrogen atom, a $C_{1-8}$ alkyl group, a carboxyl $C_{1-8}$ alkyl group or a $C_{3-8}$ alkenyl group, wherein said $C_{1-8}$ alkyl group and said $C_{3-8}$ alkenyl group may be substituted with one or more substituents.

Preferably, $R^6$ is a hydrogen atom, a $C_{1-8}$ alkyl group or a $C_{3-8}$ alkenyl group, wherein said $C_{1-8}$ alkyl group and said $C_{3-8}$ alkenyl group may be substituted with one or more substituents.

More preferably, $R^6$ is a hydrogen atom or a $C_{1-3}$ alkyl group, wherein said $C_{1-3}$ alkyl group may be substituted with one or more substituents.

In other aspect, preferably, $R^6$ is a hydrogen atom, a $C_{1-3}$ alkyl group optionally substituted by a $C_{3-8}$ cycloalkyl group (specifically, a cyclopropyl group and the like), or a $C_{3-8}$ alkenyl group.

In other aspect, preferably, $R^6$ is a hydrogen atom or a $C_{1-8}$ alkyl group.

As the $C_{1-3}$ alkyl group or the $C_{1-8}$ alkyl group for $R^6$, a methyl group, a propyl group and the like can be mentioned. As the $C_{3-8}$ alkenyl group for $R^6$, an allyl group and the like can be mentioned.

When the $C_{3-8}$ alkenyl group, the $C_{1-3}$ alkyl group, the $C_{1-8}$ alkyl group or the carboxyl $C_{1-8}$ alkyl group for $R^6$ has one or more substituents, unless otherwise indicated, examples of the substituent include a cycloalkyl group. Preferable examples of the substituent include a $C_{3-8}$ cycloalkyl group (specifically, a cyclopropyl group and the like).

In the formula (II), Ra and Rb are the same or different and each is independently a hydrogen atom, a $C_{1-8}$ alkyl group, a carboxyl $C_{1-8}$ alkyl group, a carboxyl group, an aryl group, a $C_{3-6}$ heterocyclic group containing 1 to 4 heteroatoms selected from the group of O, N and S, or a $C_{3-8}$ cycloalkyl group, or Ra and Rb together with the atom(s) to which they are bonded form a $C_{3-8}$ cycloalkane ring or a $C_{3-9}$ heterocycle containing 1-4 heteroatoms selected from the group of O, N and S, wherein said $C_{1-8}$ alkyl group, said aryl group, said $C_{3-8}$ cycloalkyl group, said $C_{3-8}$ cycloalkane ring and said $C_{3-9}$ heterocycle may be substituted with one or more substituents.

In other aspect, in the formula (II), Ra and Rb are the same or different and each is independently a hydrogen atom, a $C_{1-8}$ alkyl group, a carboxyl $C_{1-8}$ alkyl group, a carboxyl group, an aryl group, a $C_{3-6}$ heterocyclic group containing 1 to 4 heteroatoms selected from the group of O, N and S, or a $C_{3-8}$ cycloalkyl group, or Ra and Rb together with the atom(s) to which they are bonded form a $C_{3-8}$ cycloalkane ring or a $C_{3-9}$ heterocycle containing 1-4 heteroatoms selected from the group of O, N and S, wherein said $C_{1-8}$ alkyl group, said carboxyl $C_{1-8}$ alkyl group, said aryl group, said $C_{3-6}$ heterocyclic group, said cycloalkyl group, said $C_{3-8}$ cycloalkane ring and said $C_{3-9}$ heterocycle may be substituted with one or more substituents.

In the formula (II), when Ra and Rb do not form a ring, preferably, Ra and Rb are the same or different from each other and each is independently a hydrogen atom, a phenyl group, a $C_{1-8}$ alkyl group, a carboxyl group or a carboxyl $C_{1-8}$ alkyl group, wherein said phenyl group, said $C_{1-8}$ alkyl group and said is carboxyl $C_{1-8}$ alkyl group may be substituted with one or more substituents.

In the formula (II), when Ra and Rb do not form a ring, more preferably, Ra and Rb are the same or different from each other and each is independently a hydrogen atom or a $C_{1-3}$ alkyl group, wherein said $C_{1-3}$ alkyl group may be substituted with one or more substituents.

In the formula (II), when Ra and Rb form a ring, said ring is preferably, a $C_{3-8}$ cycloalkane ring which may have one or more substituents, more preferably a cyclopropane ring, a cyclobutane ring or a cyclopentane ring, which may have one or more substituents.

In other aspect, preferably, Ra and Rb are the same or different and each is independently a hydrogen atom or a $C_{1-8}$ alkyl group, or Ra and Rb together with the atom(s) to which they are bonded form a $C_{3-8}$ cycloalkane ring, wherein said $C_{1-8}$ alkyl group and said $C_{3-8}$ cycloalkane ring may substituted with a group selected from a carboxyl group, a carbamoyl group, a hydroxyl group, a phenyl group and a $C_{3-8}$ cycloalkyl group.

In other aspect, preferably, Ra and Rb are the same or different and each is independently
(1) a hydrogen atom,
(2) a $C_{1-8}$ alkyl optionally group substituted by 1 to 3 substituents selected from (a) an aryl group (specifically, a phenyl group), (b) a hydroxyl group, (c) a carbamoyl group, and (d) a $C_{1-8}$ heterocyclic group containing 1 to 4 heteroatoms selected from O, N and S (specifically, a 1H-tetrazolyl group),
(3) a carboxyl $C_{1-8}$ alkyl group,
(4) an aryl group optionally substituted by a hydroxyl group,
(5) a $C_{3-6}$ heterocyclic group containing 1 to 4 heteroatoms selected from the group of O, N and S, or
(6) a $C_{3-8}$ cycloalkyl group, or
Ra and Rb together with the atom(s) to which they are bonded form a $C_{3-8}$ cycloalkane ring, or a $C_{3-9}$ heterocycle containing 1-4 heteroatoms selected from the group of O, N and S, each of which is optionally substituted by an oxo group.

As the $C_{1-8}$ alkyl group or the $C_{1-3}$ alkyl group for Ra and Rb, a methyl group, an ethyl group, a propyl group, an isopropyl group, a sec-butyl group and the like can be mentioned.

As the carboxyl $C_{1-8}$ alkyl group for Ra and Rb, a carboxylmethyl group, a 2-carboxylethyl group, and the like can be mentioned. As the aryl group for Ra and Rb, a phenyl group and the like can be mentioned. As the $C_{3-6}$ heterocyclic group for Ra and Rb, a 1H-tetrazolyl group and the like can be mentioned. As the $C_{3-8}$ cycloalkyl group for Ra and Rb, a cyclohexyl group and the like can be mentioned.

When the $C_{1-8}$ alkyl group, the $C_{1-3}$ alkyl group, the carboxyl $C_{1-8}$ alkyl group, the aryl group, the $C_{3-6}$ heterocyclic group or the $C_{3-8}$ cycloalkyl group for Ra or Rb has one or more substituents, unless otherwise indicated, examples of the substituent include a nitro group, a halogen atom, a cyano group, a hydroxyl group, a sulfanyl group, an amino group, a guanidino group, a formyl group, a lower acyl group, a carboxyl group, a sulfo group, a phosphono group, a lower alkoxyl group, a lower alkylthio group, a lower alkylamino group, a lower acyloxy group, a lower acylamino group, a lower alkoxycarbonyl group, a carbamoyl group, a lower alkylcarbamoyl group, a lower alkylsulfonylamino group, an arylsulfonylamino group optionally having substituent(s), a cycloalkyl group optionally having substituent(s), an aryl group optionally having substituent(s), an aryloxy group optionally having substituent(s), an arylthio group optionally having substituent(s), an aralkyl group optionally having substituent(s), an aralkyloxy group optionally having substituent(s), an aralkylthio group optionally having substituent(s), a heterocyclic group optionally having substituent(s), a heterocyclyloxy group optionally having substituent(s), a heterocyclylthio group optionally having substituent(s), an oxo group, and the like. A carboxyl group, a hydroxyl group, a phenyl group, an amino group, a lower alkylthio group, a sulfanyl group, a carbamoyl group, a guanidino group, a $C_{3-8}$ cycloalkyl group, a $C_{1-8}$ heterocyclic group containing 1 to 4 heteroatoms selected from O, N and S, and the like are preferable, and a hydroxyl group, a carboxyl group, a sulfo group, a lower alkoxycarbonyl group, a 1H-tetrazolyl group, and the like are particularly preferable.

In other aspect, when the $C_{1-8}$ alkyl group, the $C_{1-3}$ alkyl group, the carboxyl $C_{1-8}$ alkyl group, the aryl group, the $C_{3-6}$ heterocyclic group or the $C_{3-8}$ cycloalkyl group for Ra or Rb has one or more substituents, unless otherwise indicated, examples of the substituent include (a) an aryl group (specifically, a phenyl group), (b) a hydroxyl group, (c) a carbamoyl group, and (d) a $C_{1-8}$ heterocyclic group containing 1 to 4 heteroatoms selected from O, N and S (specifically, a 1H-tetrazolyl group) are particularly preferable.

In other aspect, when Ra or Rb has substituent(s), unless otherwise indicated, said substituent is selected from a carboxyl group, a hydroxyl group, a phenyl group, an amino group, a methylthio group, a sulfanyl group, a carbamoyl group, a guanidino group, a $C_{3-8}$ cycloalkyl group, and a $C_{1-8}$ heterocyclic group containing 1-4 heteroatoms selected from the group consisting of O, N and S.

As the $C_{3-8}$ cycloalkane ring formed by Ra and Rb bonded to each other, a cyclopropane ring, a cyclobutane ring, a cyclopentane ring and the like can be mentioned; a cyclopropane ring and a cyclobutane ring are preferable.

As the $C_{3-9}$ heterocycle ring formed by Ra and Rb bonded to each other, a tetrahydrofuran ring, a pyrrolidine ring and the like can be mentioned; a tetrahydrofuran ring is preferable.

When the $C_{3-8}$ cycloalkane ring, the $C_{3-9}$ heterocyclie, the cyclopropane ring, the cyclobutane ring or the cyclopentane ring formed by Ra and Rb bonded to each other has one or more substituents, unless otherwise indicated, examples of the substituent include a nitro group, a halogen atom, a cyano group, a hydroxyl group, a sulfanyl group, an amino group, a guanidino group, a formyl group, a lower alkyl group, a lower alkenyl group, a lower alkynyl group, a lower acyl group, a carboxyl group, a sulfo group, a phosphono group, a lower alkoxyl group, a lower alkylthio group, a lower alkylamino group, a lower alkoxycarbonyl group, a carbamoyl group, a lower alkylcarbamoyl group, a lower alkylsulfonylamino group, a sulfamoyl group, an oxo group, and the like. A carboxyl group, a hydroxyl group, an oxo group, a phenyl group, an amino group, a lower alkylthio group, a sulfanyl group, a carbamoyl group, a guanidino group, a $C_{3-8}$ heterocyclic group containing 1 to 4 heteroatoms selected from O, N and S, a $C_{3-8}$ cycloalkyl group, and the like are preferable, and an oxo group is more preferable. The number of the substituents is preferably 1 to 3, more preferably 1 or 2, particularly preferably 1.

In the formula (II), Ring A is an arene (specifically, a benzene ring and the like), a $C_{3-6}$ heterocycle containing 1-4 heteroatoms selected from the group of O, N and S (specifically, a pyridine ring and the like), or a $C_{3-8}$ cycloalkane ring (specifically, a cyclohexane ring and the like).

In other aspect, in the formula (II), Ring A is an arene (specifically, a benzene ring and the like), a $C_{3-6}$ heterocycle containing 1-4 heteroatoms selected from the group of O, N and (specifically, a pyridine ring, a 1,2-dihydropyridine ring, a tetrahydrofuran ring and the like), a $C_{3-8}$ cycloalkane ring (specifically, a cyclohexane ring and the like) or a $C_{3-8}$ cycloalkene ring (specifically, a cyclohexene ring and the like), wherein said $C_{3-6}$ heterocycle, said $C_{3-8}$ cycloalkane ring and said $C_{3-8}$ cycloalkene ring (preferably, said $C_{3-6}$ heterocycle) may be further substituted with an oxo group, in addition to Ya and Yb.

In the formula (II), Ring A is, preferably, a benzene ring, a pyridine ring, a 1,2-dihydropyridine ring, or a $C_{3-6}$ heterocycle containing 1-4 oxygen atoms (specifically, a tetrahydrofuran ring and the like), more preferably, a benzene ring, a pyridine ring or a $C_{3-6}$ heterocycle containing 1 to 4 oxygen atoms (specifically, a tetrahydrofuran ring and the like), still more preferably, a benzene ring or a pyridine ring, most preferably, a benzene ring, wherein said 1,2-dihydropyridine ring and said $C_{3-6}$ heterocycle containing 1-4 oxygen atoms may be further substituted with an oxo group, in addition to Ya and Yb.

In the formula (II), Ya is a hydrogen atom, a halogen atom, a carboxyl group, a hydroxyl group, a carbonyl group (e.g., a $C_{1-3}$ alkoxy-carbonyl group), a carboxyl $C_{1-3}$ alkyl group or a sulfo group.

In other aspect, in the formula (II), Ya is a hydrogen atom, a halogen atom, a carboxyl group, a hydroxyl group, a $C_{1-3}$ alkoxy-carbonyl group, a carboxyl $C_{1-3}$ alkyl group or a sulfo group.

In the formula (II), Ya is, preferably a carboxyl group, a carboxyl $C_{1-3}$ alkyl group, a hydroxyl group, a sulfo group, a halogen atom or a $C_{1-3}$ alkoxy-carbonyl group, more preferably, a carboxyl group, a carboxyl $C_{1-3}$ alkyl group, a hydroxyl group or a halogen atom, even more preferably, a carboxyl group or a carboxyl $C_{1-3}$ alkyl group.

As the halogen atom for Ya, a fluorine atom and the like can be mentioned. As the carboxyl $C_{1-3}$ alkyl group for Ya, a carboxylmethyl group and the like can be mentioned. As the $C_{1-3}$ alkoxy-carbonyl group for Ya, a methoxycarbonyl and the like can be mentioned.

In the formula (II), Yb is a hydrogen atom, a halogen atom, a carboxyl group, a hydroxyl group, a carbonyl group (e.g., a $C_{1-3}$ alkoxy-carbonyl group), a carboxyl $C_{1-3}$ alkyl group, a nitro group, a cyano group or a $C_{1-3}$ alkoxyl group.

In other aspect, in the formula (II), Yb is a hydrogen atom, a halogen atom, a carboxyl group, a hydroxyl group, a $C_{1-3}$ alkoxy-carbonyl group, a carboxyl $C_{1-3}$ alkyl group, a nitro group, a cyano group or a $C_{1-3}$ alkoxyl group.

In the formula (II), Yb is, preferably a hydrogen atom, a $C_{1-3}$ alkoxycarboxyl group, a hydroxyl group or a halogen atom, more preferably, a carboxyl group or a hydroxyl group.

In other aspect, in the formula (II), Yb is preferably, a hydrogen atom, a halogen atom, a carboxyl group or a hydroxyl group.

In other aspect, in the formula (II), Yb is preferably, a hydrogen atom, a carboxyl group, a hydroxyl group, a $C_{1-3}$ alkoxy-carbonyl group or a $C_{1-3}$ alkoxyl group.

As the $C_{1-3}$ alkoxy-carbonyl group for Yb, a methoxycarbonyl group and the like can be mentioned. As the $C_{1-3}$ alkoxyl group for Yb, a methoxy group and the like can be mentioned.

In the formula (II), p is 0, 1, 2, 3 or 4, preferably, 0, 1, 2 or 3, more preferably, 0, 1 or 2.

In the formula (II), q is 0 or 1, preferably, 1.

In the formula (II), preferable combinations of p and q are when p=1 or 2, and q=0, and when p=0 or 1, and q=1, further preferable combinations are when p=1 or 2, and q=0, or when p=0 and q=1.

In the formula (I), $R^7$ is a hydrogen atom, a halogen atom or a nitro group, preferably a hydrogen atom, a halogen atom such as a fluorine atom or a chlorine atom, more preferably, a halogen atom such as a fluorine atom or a chlorine atom, still more preferably, a fluorine atom. The structure-activity relationship for the variation on this substituent is well-supported by the previous application by the present inventors, WO2011/071048, which is incorporated herein by reference in its entirety.

In another preferable embodiment, in the formula (I), X is —OR³ or —NR⁸R⁹, preferably —OR³, more preferably —OH.

$R^8$ is an optionally substituted $C_{1-8}$ alkyl group, an optionally substituted aryl group, an optionally substituted $C_{3-6}$ heterocyclic group, an optionally substituted $C_{3-8}$ cycloalkyl group, or an optionally substituted $C_{3-8}$ cycloalkenyl group, and $R^9$ is a hydrogen atom, an optionally substituted $C_{1-8}$ alkyl group or an optionally substituted $C_{3-8}$ alkenyl group; or $R^8$ and $R^9$ together with the nitrogen atom to which they are bonded form an optionally substituted $C_{2-9}$ heterocycle.

Preferably, $R^8$ is (1) a $C_{1-8}$ alkyl group (e.g., a methyl group, an ethyl group, a propyl group, an isopropyl group, a butyl group, an isobutyl group, a pentyl group, a 1,2-dimethylbutyl group, a 1,1-diethylpropyl group) optionally substituted by 1 to 3 substituents selected from
  (a) a carboxyl group,
  (b) a hydroxyl group,
  (c) an aryl group (e.g., a phenyl group) optionally substituted by a carboxyl group or a hydroxyl group,
  (d) a sulfo group,
  (e) a $C_{3-8}$ cycloalkyl group (e.g., a cyclohexyl group),
  (f) a carbamoyl group,
  (g) an amino group,
  (h) a cyano group,
  (i) a $C_{1-8}$ heterocyclic group (e.g., a 1H-tetrazolyl group), and
  (j) a $C_{1-3}$ alkyl-carbamoyl group (e.g., an N-methylcarbamoyl group) optionally substituted by a carboxyl group, (2) an aryl group (e.g., a phenyl group) optionally substituted by 1 to 3 substituents selected from
  (a) a carboxyl group,
  (b) a hydroxyl group,
  (c) a $C_{1-3}$ alkyl group (e.g., a methyl group) optionally substituted by a carboxyl group,
  (d) a $C_{1-3}$ alkoxy-carbonyl group (e.g., a methoxycarbonyl group), and
  (e) a sulfo group, (3) a $C_{3-8}$ heterocyclic group (e.g., a tetrahydrofuryl group, a pyridyl group, a 1,2-dihydropyridyl group) optionally substituted by 1 to 3 substituents selected from
  (a) an oxo group,
  (b) a $C_{1-3}$ alkoxyl group (e.g., a methoxy group), and
  (c) a halogen atom (e.g., a fluorine atom), (4) a $C_{1-8}$ cycloalkyl group (e.g., a cyclopropyl group, a cyclobutyl group, a cyclohexyl group) optionally substituted by a carboxyl group, or (5) a $C_{3-8}$ cycloalkenyl group (e.g., a cyclohexenyl group) optionally substituted by a carboxyl group, and $R^9$ is a hydrogen atom, a $C_{1-8}$ alkyl group (e.g., a methyl group, a propyl group) optionally substituted by a $C_{3-8}$ cycloalkyl group (e.g., a cyclopropyl group), or a $C_{3-8}$ alkenyl group (e.g., an allyl group); or $R^8$ and $R^9$ together with the nitrogen atom to which they are bonded form a $C_{2-9}$ heterocycle (e.g., an aziridine ring, an azetidine ring, a pyrrolidine ring, a piperidine ring, a tetrahydroisoquinoline ring) optionally substituted by 1 to 3 substituents selected from
  (1) a carboxyl group,
  (2) a $C_{1-3}$ alkyl group (e.g., a methyl group) optionally substituted by a carboxyl group,
  (3) a halogen atom (e.g., a fluorine atom), and
  (4) a hydroxyl group.

In more preferable embodiment, X is preferably —OH or —NR⁸'R⁹', more preferably —OH, from the aspect of stability and few side effects.

$R^{8'}$ is a substituted $C_{1-8}$ alkyl group, a substituted aryl group, a substituted $C_{3-6}$ heterocyclic group, a substituted $C_{3-8}$ cycloalkyl group, or a substituted $C_{3-8}$ cycloalkenyl group, each of which has one carboxyl group, and $R^{9'}$ is a hydrogen atom, an optionally substituted $C_{1-8}$ alkyl group which has no carboxyl group, or an optionally substituted $C_{3-8}$ alkenyl group which has no carboxyl group; or $R^{8'}$ and $R^{9'}$ together with the nitrogen atom to which they are bonded form a substituted $C_{2-9}$ heterocycle which has one carboxyl group.

Preferably, $R^{8'}$ is (1) a $C_{1-8}$ alkyl group (e.g., a methyl group, an ethyl group, a propyl group, an isopropyl group, a butyl group, an isobutyl group, a pentyl group, a 1,2-dimethylbutyl group, a 1,1-diethylpropyl group) substituted by 1 to 3 substituents selected from
  (a) a carboxyl group,
  (b) a hydroxyl group,
  (c) an aryl group (e.g., a phenyl group) optionally substituted by a carboxyl group or a hydroxyl group,
  (d) a sulfo group,
  (e) a $C_{3-8}$ cycloalkyl group (e.g., a cyclohexyl group),
  (f) a carbamoyl group,
  (g) an amino group,
  (h) a cyano group,
  (i) a $C_{1-8}$ heterocyclic group (e.g., a 1H-tetrazolyl group), and
  (j) a $C_{1-3}$ alkyl-carbamoyl group (e.g., an N-methylcarbamoyl group) optionally substituted by a carboxyl group,
  provided that said substituted $C_{1-8}$ alkyl group has one carboxyl group, (2) an aryl group (e.g., a phenyl group) substituted by 1 to 3 substituents selected from
  (a) a carboxyl group,
  (b) a hydroxyl group,
  (c) a $C_{1-3}$ alkyl group (e.g., a methyl group) optionally substituted by a carboxyl group,
  (d) a $C_{1-3}$ alkoxy-carbonyl group (e.g., a methoxycarbonyl group), and
  (e) a sulfo group,
  provided that said substituted aryl group has one carboxyl group, (3) a $C_{3-8}$ cycloalkyl group (e.g., a cyclopropyl group, a cyclobutyl group, a cyclohexyl group) substituted by one carboxyl group, or (4) a $C_{3-8}$ cycloalkenyl group (e.g., a cyclohexenyl group) substituted by one carboxyl group, and $R^{9'}$ is a hydrogen atom, a $C_{1-8}$ alkyl group (e.g., a methyl group, a propyl group) optionally substituted by a $C_{3-8}$ cycloalkyl group (e.g., a cyclopropyl group), or a $C_{3-8}$ alkenyl group (e.g., an allyl group); or $R^{8'}$ and $R^{9'}$ together with the nitrogen atom to which they are bonded form a $C_{2-9}$ heterocycle (e.g., an aziridine ring, an azetidine ring, a pyrrolidine ring, a piperidine ring, a tetrahydroisoquinoline ring) substituted by 1 to 3 substituents selected from
  (1) a carboxyl group,
  (2) a $C_{1-3}$ alkyl group (e.g., a methyl group) optionally substituted by a carboxyl group,
  (3) a halogen atom (e.g., a fluorine atom), and
  (4) a hydroxyl group,
  provided that said substituted $C_{2-9}$ heterocycle formed by $R^{8'}$ and $R^{9'}$ has one carboxyl group.

More preferably, $R^{8'}$ is (1) a $C_{1-8}$ alkyl group (e.g., a methyl group, an ethyl group, a propyl group, an isopropyl group, a butyl group, an isobutyl group, a pentyl group, a 1,2-dimethylbutyl group) substituted by 1 to 3 substituents selected from
  (a) a carboxyl group,
  (b) a hydroxyl group,
  (c) an aryl group (e.g., a phenyl group) optionally substituted by a carboxyl group or a hydroxyl group,
  (d) a $C_{3-8}$ cycloalkyl group (e.g., a cyclohexyl group),
  (e) a carbamoyl group,
  (f) an amino group,
  (g) a $C_{1-8}$ heterocyclic group (e.g., a 1H-tetrazolyl group), and
  (h) a $C_{1-3}$ alkyl-carbamoyl group (e.g., an N-methylcarbamoyl group) optionally substituted by a carboxyl group,
  provided that said substituted $C_{1-8}$ alkyl group has one carboxyl group, (2) an aryl group (e.g., a phenyl group) substituted by 1 to 3 substituents selected from
  (a) a carboxyl group,
  (b) a hydroxyl group,
  (c) a $C_{1-3}$ alkyl group (e.g., a methyl group) optionally substituted by a carboxyl group, and
  (d) a $C_{1-3}$ alkoxy-carbonyl group (e.g., a methoxycarbonyl group),
  provided that said substituted aryl group has one carboxyl group, (3) a $C_{3-8}$ cycloalkyl group (e.g., a cyclopropyl group, a cyclobutyl group, a cyclohexyl group) substituted by one carboxyl group, or (4) a $C_{3-8}$ cycloalkenyl group (e.g., a cyclohexenyl group) substituted by one carboxyl group, and $R^{9'}$ is a hydrogen atom, a $C_{1-8}$ alkyl group (e.g., a methyl group, a propyl group) optionally substituted by a $C_{3-8}$ cycloalkyl group (e.g., a cyclopropyl group), or a $C_{3-8}$ alkenyl group (e.g., an allyl group); or $R^{8'}$ and $R^{9'}$ together with the nitrogen atom to which they are bonded form a $C_{2-9}$ heterocycle (e.g., an aziridine ring, an azetidine ring, a pyrrolidine ring, a piperidine ring, a tetrahydroisoquinoline ring) substituted by 1 to 3 substituents selected from
  (1) a carboxyl group,
  (2) a $C_{1-3}$ alkyl group (e.g., a methyl group) optionally substituted by a carboxyl group, and
  (3) a hydroxyl group,
  provided that said substituted $C_{2-9}$ heterocycle formed by $R^{8'}$ and $R^{9'}$ has one carboxyl group.

In the formula (I), when $R^1$ and $R^2$ are both methyl groups, then neither of $R^4$ nor $R^5$ is an ethyl group substituted with two carboxyl groups, and when $R^1$ and $R^2$ are both methyl groups, then the group represented by the formula (II) is not a group represented by the formula:

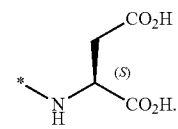

In other aspect, in the formula (I), when $R^1$ and $R^2$ are both methyl groups, then X is not a group represented by the formula:

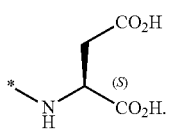

As preferable embodiments of the compound represented by the formula (I) or a pharmaceutically acceptable salt thereof, the following can also be mentioned;

provided, however, that when $R^1$ and $R^2$ are both methyl groups, then X is not a group represented by the formula:

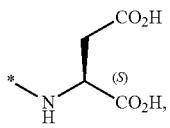

in the formula (I).

Compound 1-A.

The compound represented by the formula (I) wherein,
$R^1$ and $R^2$ are both methyl groups,
X is —$NR^4R^5$, wherein
$R^4$ is a hydrogen atom, a methyl group, an ethyl group, a propyl group or a propenyl group,
$R^5$ is a $C_{3-4}$ alkyl group having 1 or 2 substituent(s) selected from the group of a carboxyl group and a hydroxyl group, and
$R^7$ is a fluorine atom,
or a pharmaceutically acceptable salt thereof.

Compound 1-B.

The compound represented by the formula (I) wherein,
$R^1$ and $R^2$ are both ethyl groups,
X is —$NR^4R^5$, wherein
$R^4$ is a hydrogen atom, a methyl group, an ethyl group, a propyl group or a propenyl group,
$R^5$ is a $C_{1-6}$ alkyl group having 1 or 2 substituent(s) selected from the group of a carboxyl group, a hydroxyl group, an amino group and a carbamoyl group, and
$R^7$ is a fluorine atom,
or a pharmaceutically acceptable salt thereof.

Compound 1-C.

The compound represented by the formula (I) wherein,
$R^1$ and $R^2$ are both methyl groups or an ethyl group,
X is the group represented by formula (II) wherein,
$R^6$ is a hydrogen atom or a methyl group,
$R^7$ is a fluorine atom,
p=0,
q=1,
Ring A is a phenyl group, a 3-pyridyl group or a 4-pyridyl group,
Ya is a hydrogen group, a carboxyl group, a hydroxyl group, a methoxy group, a carboxylmethyl group, an oxo group or a halogen atom,
Yb is a hydrogen atom or a halogen atom, or a pharmaceutically acceptable salt thereof.

Compound 2-A.

The compound represented by the formula (I) wherein:
$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;
X is —$OR^3$, —$NR^4R^5$ or the group represented by the formula (II) wherein,
$R^3$ is a hydrogen atom or a $C_{1-4}$ alkyl group;

$R^4$ is
(1) a carboxyl $C_{1-8}$ alkyl group optionally substituted by 1 to 3 substituents selected from (a) a hydroxyl group, (b) an aryl group, (c) a $C_{3-8}$ cycloalkyl group, (d) a carbamoyl group, (e) an amino group, (f) an aryl group optionally substituted by a hydroxyl group, (g) a $C_{1-3}$ alkylcarbamoyl group optionally substituted by a carboxyl group, and (h) a $C_{1-8}$ heterocyclic group, or
(2) a $C_{1-8}$ alkyl group optionally substituted by 1 to 3 substituents selected from (a) a sulfo group, (b) a cyano group, (c) a $C_{1-8}$ heterocyclic group, and (d) an aryl group optionally substituted by a carboxyl group, and $R^5$ is a hydrogen atom, a $C_{1-3}$ alkyl group optionally substituted by a $C_{3-8}$ cycloalkyl group, or a $C_{3-8}$ alkenyl group; or $R^4$ and $R^5$ together with the nitrogen atom to which they are bonded form a $C_{2-9}$ heterocycle substituted by 1 to 3 substituents selected from (1) a halogen atom, (2) a hydroxyl group, (3) a carboxyl group, and (4) a carboxyl $C_{1-3}$ alkyl group;

$R^6$ is a hydrogen atom, a $C_{1-3}$ alkyl group optionally substituted by a $C_{3-8}$ cycloalkyl group, or a $C_{3-8}$ alkenyl group; and Ra and Rb are the same or different and each is independently
(1) a hydrogen atom,
(2) a $C_{1-8}$ alkyl group optionally substituted by 1 to 3 substituents selected from (a) an aryl group, (b) a hydroxyl group, (c) a carbamoyl group, and (d) a $C_{1-8}$ heterocyclic group containing 1 to 4 heteroatoms selected from O, N and S,
(3) a carboxyl $C_{1-8}$ alkyl group,
(4) an aryl group optionally substituted by a hydroxyl group,
(5) a $C_{3-6}$ heterocyclic group containing 1 to 4 heteroatoms selected from the group of O, N and S, or
(6) a $C_{3-8}$ cycloalkyl group, or Ra and Rb together with the atom(s) to which they are bonded form a $C_{3-8}$ cycloalkane ring, or a $C_{3-9}$ heterocycle containing 1-4 heteroatoms selected from the group of O, N and S, each of which is optionally substituted by an oxo group;

Ring A is an arene, a $C_{3-6}$ heterocycle containing 1-4 heteroatoms selected from the group of O, N and S, a $C_{3-8}$ cycloalkane ring or a $C_{3-8}$ cycloalkene ring, wherein said $C_{3-6}$ heterocycle, said $C_{3-8}$ cycloalkane ring and said $C_{3-8}$ cycloalkene ring may be further substituted with an oxo group, in addition to Ya and Yb;

Ya is a hydrogen atom, a halogen atom, a carboxyl group, a hydroxyl group, a $C_{1-3}$ alkoxy-carbonyl group, a carboxyl $C_{1-3}$ alkyl group or a sulfo group;

Yb is a hydrogen atom, a halogen atom, a carboxyl group, a hydroxyl group, a $C_{1-3}$ alkoxy-carbonyl group, a carboxyl $C_{1-3}$ alkyl group, a nitro group, a cyano group or a $C_{1-3}$ alkoxyl group;

p is 0, 1, 2, 3 or 4;

q is 0 or 1; and $R^7$ is a hydrogen atom, a halogen atom or a nitro group, or a pharmaceutically acceptable salt thereof.

Compound 2-B.

The compound represented by the formula (I) wherein:
$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;
X is —$OR^3$, wherein
$R^3$ is a hydrogen atom or a $C_{1-4}$ alkyl group; and
$R^7$ is a hydrogen atom, a halogen atom or a nitro group, or a pharmaceutically acceptable salt thereof.

Compound 2-C.

The compound represented by the formula (I) wherein:

$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;

X is —OH, and $R^7$ is a hydrogen atom, a halogen atom or a nitro group, or a pharmaceutically acceptable salt thereof.

Compound 2-A'.

The compound represented by the formula (I) wherein:

$R^1$ and $R^2$ are the same or different and each is independently a $C_{1-4}$ alkyl group or a $C_{2-4}$ alkenyl group, or $R^1$ m and $R^2$ together with the carbon atom to which they are bonded form a $C_{3-8}$ cycloalkane ring;

X is —$OR^3$ or —$NR^8R^9$; wherein $R^3$ is a hydrogen atom or a $C_{1-4}$ alkyl group;

$R^8$ is
(1) a $C_{1-8}$ alkyl group optionally substituted by 1 to 3 substituents selected from (a) a carboxyl group, (b) a hydroxyl group, (c) an aryl group optionally substituted by a carboxyl group or a hydroxyl group, (d) a sulfo group, (e) a $C_{3-8}$ cycloalkyl group, (f) a carbamoyl group, (g) an amino group, (h) a cyano group, (i) a $C_{1-8}$ heterocyclic group, and (j) a $C_{1-3}$ alkylcarbamoyl group optionally substituted by a carboxyl group,
(2) an aryl group optionally substituted by 1 to 3 substituents selected from (a) a carboxyl group, (b) a hydroxyl group, (c) a $C_{1-3}$ alkyl group optionally substituted by a carboxyl group, (d) a $C_{1-3}$ alkoxy-carbonyl group, and (e) a sulfo group,
(3) a $C_{3-6}$ heterocyclic group optionally substituted by 1 to 3 substituents selected from (a) an oxo group, (b) a $C_{1-3}$ alkoxyl group, and (c) a halogen atom,
(4) a $C_{3-8}$ cycloalkyl group optionally substituted by a carboxyl group, or
(5) a $C_{3-8}$ cycloalkenyl group optionally substituted by a carboxyl group, and $R^9$ is a hydrogen atom, a $C_{1-8}$ alkyl group optionally substituted by a $C_{3-8}$ cycloalkyl group, or a $C_{3-8}$ alkenyl group; or $R^8$ and $R^9$ together with the nitrogen atom to which they are bonded form a $C_{2-9}$ heterocycle optionally substituted by 1 to 3 substituents selected from (1) a carboxyl group, (2) a $C_{1-3}$ alkyl group optionally substituted by a carboxyl group, (3) a halogen atom, and (4) a hydroxyl group; and $R^7$ is a hydrogen atom, a halogen atom or a nitro group, or a pharmaceutically acceptable salt thereof.

Compound 2-B'.

The compound represented by the formula (I) wherein:

$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;

X is —OH or —$NR^{9'}R^{9'}$, wherein $R^{8'}$ is
(1) a $C_{1-8}$ alkyl group substituted by 1 to 3 substituents selected from (a) a carboxyl group, (b) a hydroxyl group, (c) an aryl group optionally substituted by a carboxyl group or a hydroxyl group, (d) a sulfo group, (e) a $C_{3-8}$ cycloalkyl group, (f) a carbamoyl group, (g) an amino group, (h) a cyano group, (i) a $C_{1-8}$ heterocyclic group, and (j) a $C_{1-3}$ alkylcarbamoyl group optionally substituted by a carboxyl group, provided that said substituted $C_{1-8}$ alkyl group has one carboxyl group,
(2) an aryl group substituted by 1 to 3 substituents selected from (a) a carboxyl group, (b) a hydroxyl group, (c) a $C_{1-3}$ alkyl group optionally substituted by a carboxyl group, (d) a $C_{1-3}$ alkoxy-carbonyl group, and (e) a sulfo group, provided that said substituted aryl group has one carboxyl group,
(3) a $C_{3-8}$ cycloalkyl group substituted by one carboxyl group, or
(4) a $C_{3-8}$ cycloalkenyl group substituted by one carboxyl group, and $R^{9'}$ is a hydrogen atom, a $C_{1-8}$ alkyl group optionally substituted by a $C_{3-8}$ cycloalkyl group, or a $C_{3-8}$ alkenyl group; or $R^{8'}$ and $R^{9'}$ together with the nitrogen atom to which they are bonded form a $C_{2-9}$ heterocycle substituted by 1 to 3 substituents selected from (1) a carboxyl group, (2) a $C_{1-3}$ alkyl group optionally substituted by a carboxyl group, (3) a halogen atom, and (4) a hydroxyl group, provided that said substituted $C_{2-9}$ heterocycle formed by $R^{8'}$ and $R^{9'}$ has one carboxyl group; and $R^7$ is a hydrogen atom, a halogen atom or a nitro group, or a pharmaceutically acceptable salt thereof.

Compound 3-A.

A compound represented by any of the following formulas;

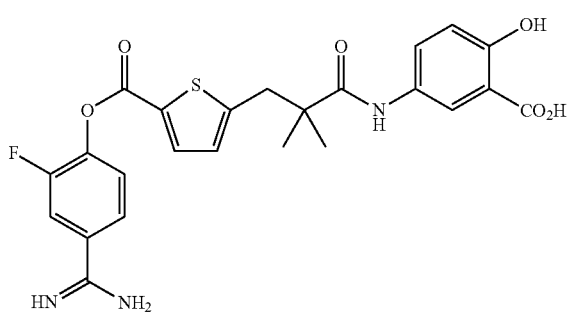

47

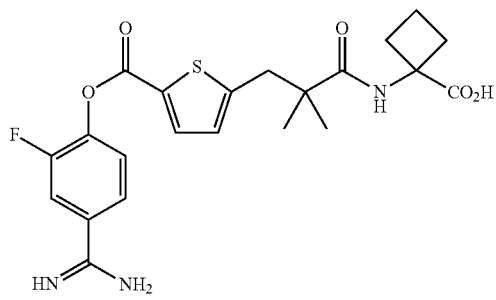

56

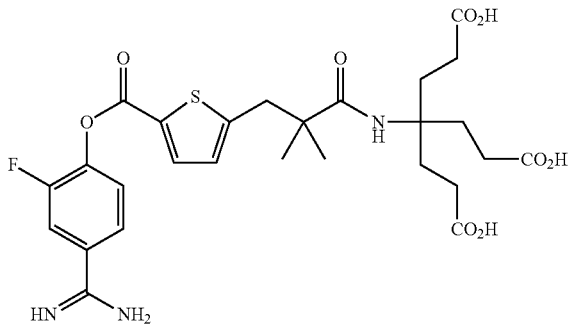

58

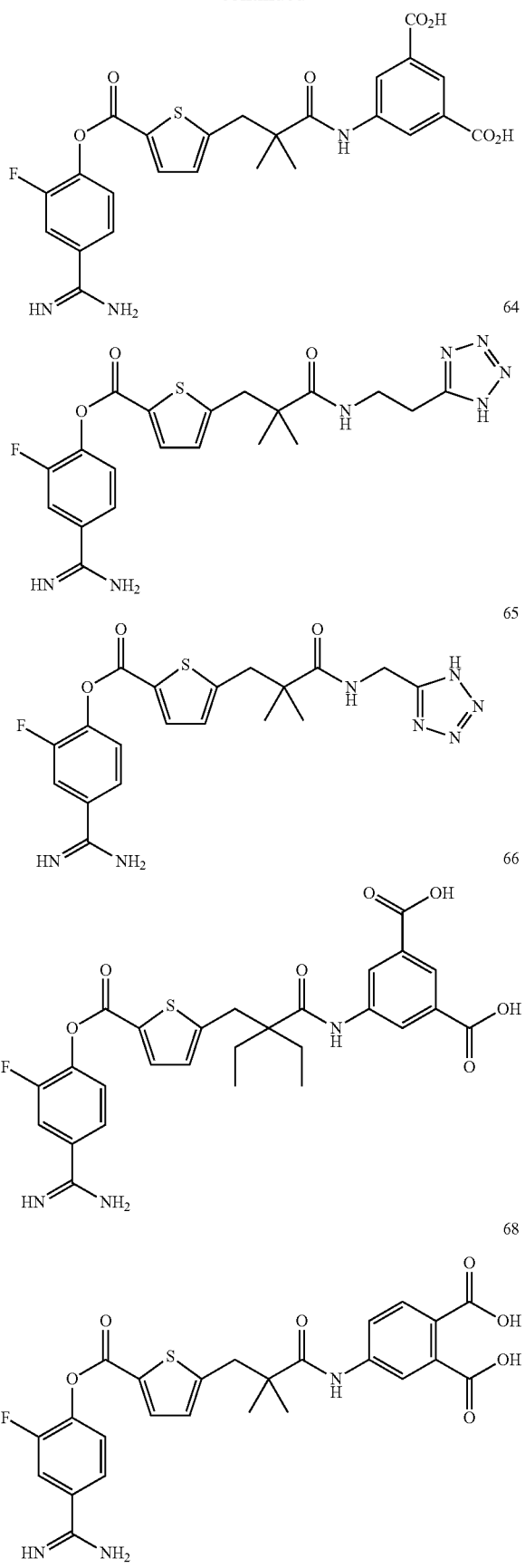
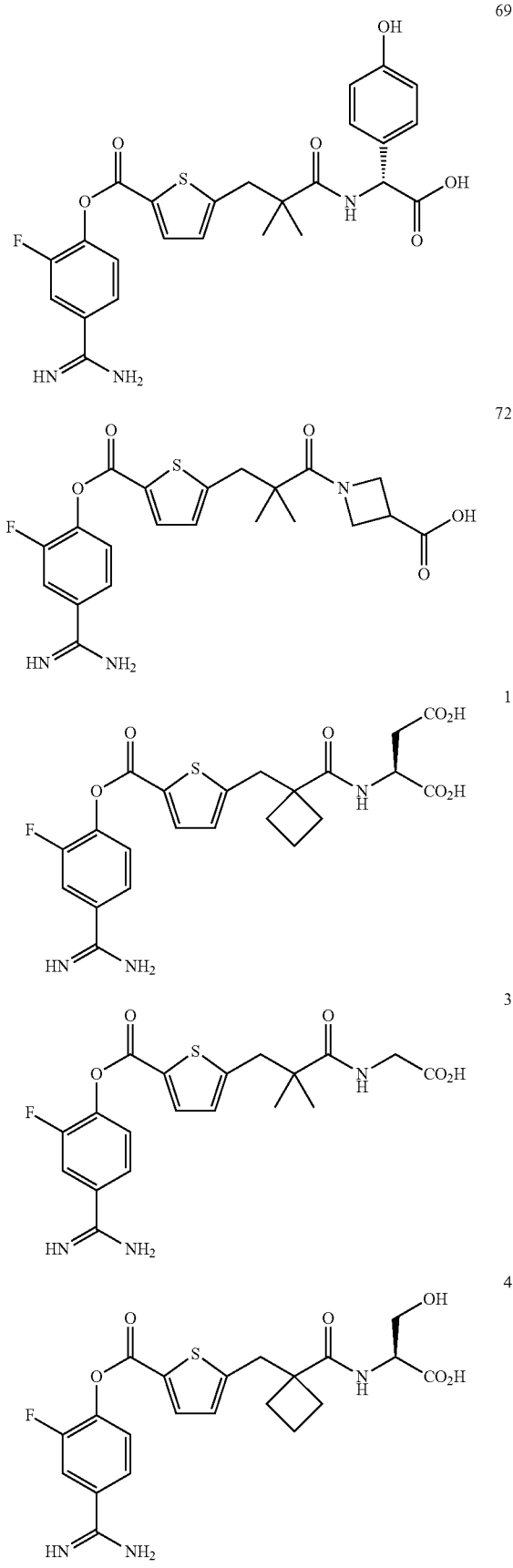

-continued
5
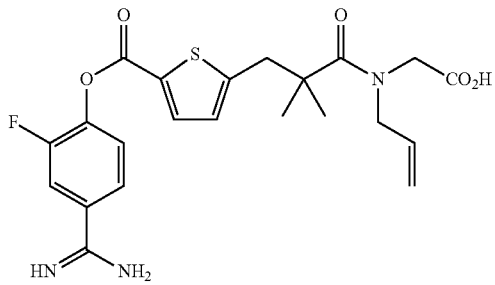
6
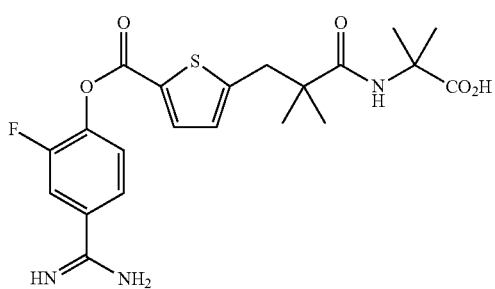
10
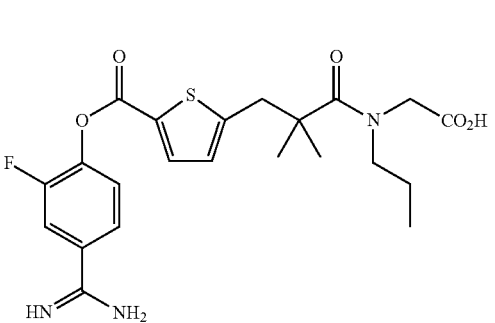
11
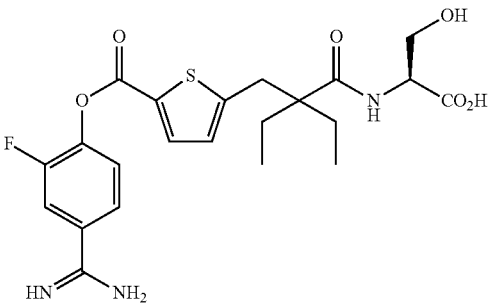
13
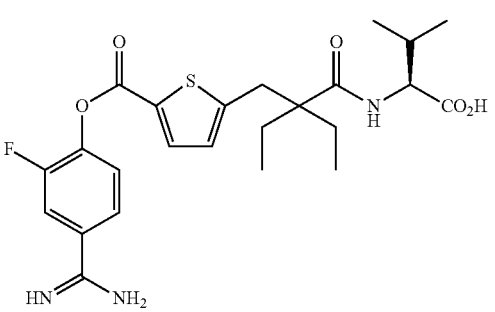
-continued
14
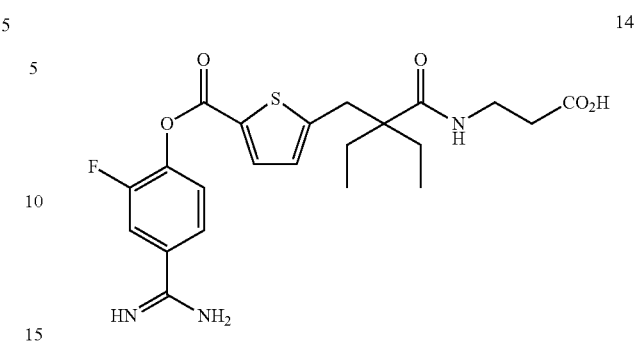
18
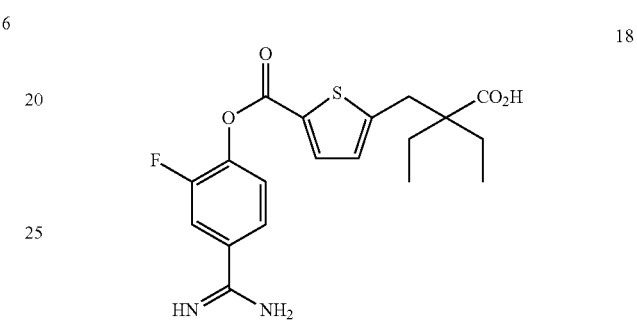
19
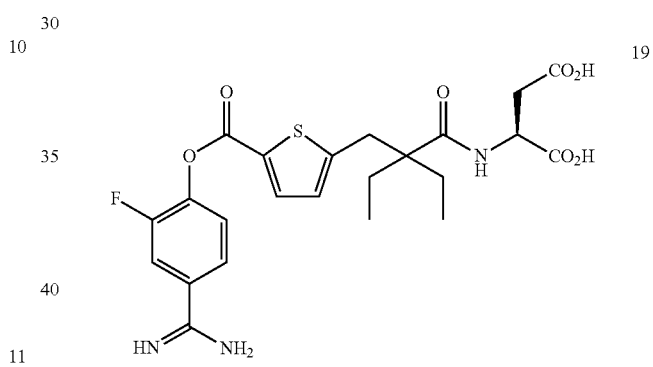
28
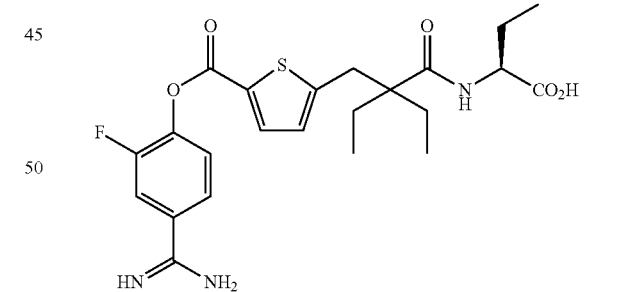
33
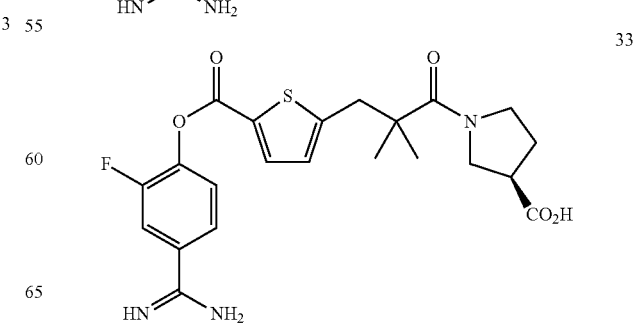

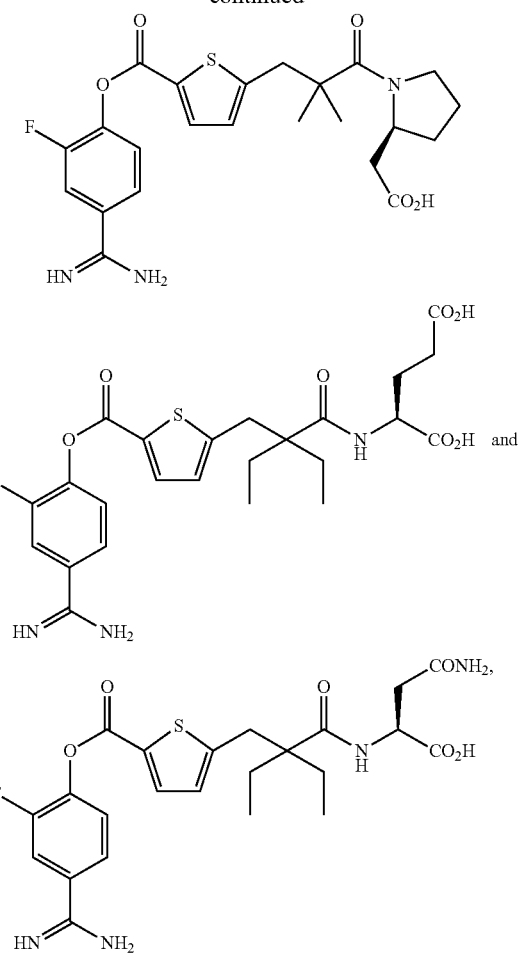

or a pharmaceutically acceptable salt thereof.
Compound 3-B.

A compound represented by any of the following formulas;

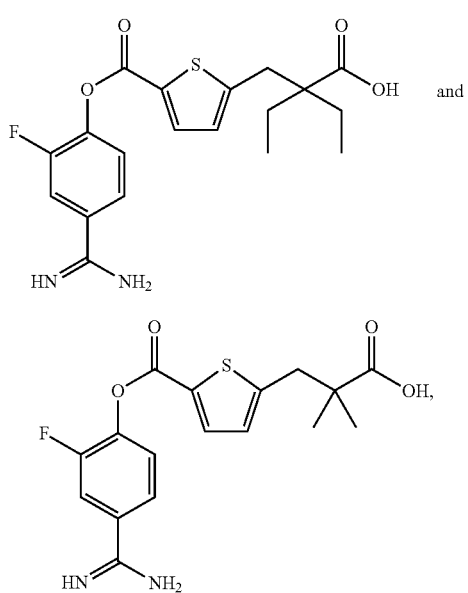

or a pharmaceutically acceptable salt thereof.

As the serine protease inhibitory activity, an activity m of simultaneously inhibiting trypsin and enteropeptidase is preferable.

When the compound of the present invention can form a salt, a pharmaceutically acceptable salt is preferable. Examples of such pharmaceutically acceptable salts for a compound having an acidic group such as a carboxyl group and the like include an ammonium salt, salts with alkali metals such as sodium, potassium, and the like, salts with alkaline earth metals such as calcium, magnesium, and the like, an aluminum salt, a zinc salt, salts with an organic amines such as triethylamine, ethanolamine, morpholine, pyrrolidine, piperidine, piperazine, dicyclohexylamine, and the like, and salts with a basic amino acid such as arginine, lysine, and the like. Examples of such pharmaceutically acceptable salts for a compound having a basic group include salts with an inorganic acid such as hydrochloric acid, sulfuric acid, phosphoric acid, nitric acid, hydrobromic acid, and the like, salts with an organic carboxylic acid such as acetic acid, citric acid, benzoic acid, maleic acid, fumaric acid, tartaric acid, succinic acid, tannic acid, butyric acid, pamoic acid, enanthic acid, decanoic acid, salicylic acid, lactic acid, oxalic acid, mandelic acid, malic acid, and the like, and salts with an organic sulfonic acid such as methanesulfonic acid, benzenesulfonic acid, p-toluenesulfonic acid, and the like.

The compound of the present invention also encompasses all optical isomers, stereoisomers, tautomers, rotamers, and mixtures thereof at optional ratios. These can be obtained each as a single product according to a synthesis method and separation method known per se. For example, an optical isomer can be obtained by using an optically active synthesis intermediate or by optically resolving a racemate of a synthesis intermediate or final product by a conventional method.

The compound of the present invention also includes solvates of the compound such as hydrates, alcohol adducts, and the like.

The compound of the present invention may be converted to a prodrug. The prodrug of the present invention means a compound that is converted in the body to produce the compound of the present invention. For example, when an active form contains a carboxyl group or a phosphoric acid group, an ester thereof, amide thereof, and the like can be mentioned. When an active form contains a carboxyl group, a group to be converted to a carboxyl group by oxidative metabolism, such as a hydroxymethyl group and the like can be mentioned. In addition, when the active form contains an amino group, examples thereof include an amide thereof, a carbamate thereof, and the like. When the active form contains a hydroxyl group, examples thereof include esters thereof, carbonates thereof, carbamates thereof, and the like. When the compound of the present invention is converted to a prodrug, it may be bonded to an amino acid or saccharide.

The present invention also encompasses a metabolite of the compound of the present invention. The metabolite of the compound of present invention means a compound resulting from the conversion of the compound of the present invention by a metabolic enzyme and the like in the body. For example, a compound wherein a hydroxyl group is introduced on the benzene ring of the compound of the present invention due to the metabolism, a compound wherein glucuronic acid, glucose, or an amino acid is bonded to the carboxylic acid moiety of the compound of the present invention or a hydroxyl group is added by the metabolism, and the like can be mentioned.

The compound of the present invention and a pharmaceutically acceptable salt thereof have a superior blood glucose elevation suppressing action for mammals such as humans, bovines, horses, dogs, mice, rats, cats, and the like, and can be used as a medicament, which is administered as it is or as a pharmaceutical composition containing the same mixed with a pharmaceutically acceptable carrier according to a method known per se. While oral administration is generally preferable, parenteral administration can also be employed (e.g., routes such as intravenous, subcutaneous, intramuscular, suppository, enema, ointment, patch, sublingual, eye drop, inhalation administrations, and the like). While the dose used for the above-mentioned objects is determined according to the desired treatment effect, administration method, duration of treatment, age, body weight, and the like, a daily dose of 1 µg to 10 g for oral administration and 0.01 µg to 1 g, preferably 0.1 µg to 1 g, for parenteral administration is used, which is generally administered to an adult by an oral or parenteral route in one to several portions per day. In addition, the content of the compound of the present invention in the above-mentioned pharmaceutical composition is about 0.01 wt % to 100 wt % of the whole composition.

Examples of the pharmaceutically acceptable carrier for the pharmaceutical composition of the present invention include various organic or inorganic carrier substances conventionally used as preparation materials. For example, an excipient, lubricant, binder, disintegrant, water-soluble polymer, and basic inorganic salt in a solid preparation; a solvent, solubilizing agents, suspending agent, isotonicity agent, buffering agent, and soothing agent in a liquid preparation, and the like can be mentioned. Where necessary, general additives such as a preservative, antioxidant, colorant, sweetening agent, souring agent, effervescing agent, flavor, and the like can also be used.

The dosage form of such a pharmaceutical composition may be a tablet, powder, pill, granule, capsule, suppository, solution, sugar-coated agent, depot, syrup, suspension, emulsion, troche, sublingual agent, adhesive preparation, oral disintegrant (tablet), inhalant, enema, ointment, patch, tape, or eye drop, and these can be produced using conventional formulation auxiliaries and according to a conventional method.

The pharmaceutical composition of the present invention can be produced according to a method conventionally used in the technical field of pharmaceutical formulation, for example, the method described in the Japanese Pharmacopoeia, which is incorporated herein by reference in its entirety, and the like. Specific production methods of the preparation are explained in detail in the following.

For example, when the compound of the present invention is prepared as an oral preparation, an excipient and, where necessary, a binder, disintegrant, lubricant, colorant, flavoring agent, and the like are further added, and the mixture is processed to give, for example, a tablet, powder, pill, granule, capsule, suppository, solution, sugar-coated agent, depot, syrup, and the like according to a conventional method. Examples of the excipient include lactose, cornstarch, sucrose, glucose, sorbitol, crystalline cellulose, and the like. Examples of the binder include polyvinyl alcohol, polyvinyl ether, ethylcellulose, methylcellulose, gum arabic, tragacanth, gelatin, shellac, hydroxypropylcellulose, hydroxypropylstarch, polyvinylpyrrolidone, and the like. Examples of the disintegrant include starch, agar, gelatin powder, crystalline cellulose, calcium carbonate, sodium hydrogen carbonate, calcium citrate, dextran, pectin, and the like. Examples of the lubricant include magnesium stearate, talc, polyethylene glycol, silica, hydrogenated vegetable oil, and the like. As the colorant, one acceptable to add to a pharmaceutical product is used, and as the flavoring agent, cocoa powder, menthol, aromatic acid, peppermint oil, borneol, powdered cinnamon bark, and the like are used. Where necessary, these tablets and granules are applied with a coating as appropriate such as a sugar coating, gelatin coating, and the like.

When an injection is to be prepared, a pH adjuster, buffering agent, stabilizer, preservative, and the like are added where necessary, and the mixture is processed to give subcutaneous, intramuscular, or intravenous injection according to a conventional method.

While the compound of the present invention can be used as an agent for the treatment or prophylaxis of diabetes as mentioned above, it can also be used in combination with other therapeutic agents for diabetes and agents for the treatment or prophylaxis of diabetic complications, which are used generally. Examples of the therapeutic agents for diabetes and agents for the treatment or prophylaxis of diabetic complications, which are used generally, include combinations and mixtures of one or more kinds of an insulin preparation, insulin derivative, insulin-like agent, insulin secretagogue, insulin sensitizer, biguanide, gluconeogenesis inhibitor, glucose absorption inhibitor, renal glucose reabsorption inhibitor, $\beta 3$ adrenoceptor agonist, glucagon-like peptide-1 (7-37), glucagon-like peptide-1 (7-37) analogs, glucagon-like peptide-1 receptor agonist, dipeptidyl peptidase IV inhibitor, aldose reductase inhibitor, inhibitor of advanced glycation end product formation, glycogen synthase kinase-3 inhibitor, glycogen phosphorylase inhibitor, antihyperlipidemic drug, anorectic agent, lipase inhibitor, antihypertensive agent, peripheral circulation improving agent, antioxidant, a therapeutic drug for diabetic neuropathy, and the like.

A medicament to be used in combination with the compound of the present invention may be mixed to give a single agent or each may be formulated into separate preparations, or prepared into a combination preparation (set, kit, or pack) obtained by packaging each of the separately formulated preparations in one container.

The administration form of combined use is not particularly limited and, for example, (1) administration as a single preparation, (2) simultaneous administration of separate preparations by the same administration route, (3) administration of separate preparations in a staggered manner by the same administration route, (4) simultaneous administration of separate preparations by different administration routes, (5) administration of separate preparations in a staggered manner by different administration routes, and the like can be mentioned.

In addition, the compound of the present invention is also useful even when contained in food.

A food composition containing the compound of the present invention is useful as a food for the treatment or prophylaxis of diabetes.

The "food" of the present invention means general foods, which include foods for specified health uses and foods with nutrient function claims defined by Food with Health Claims of Consumer Affairs Agency, Government of Japan, in addition to general foods including so-called health food, and further encompasses dietary supplements.

The form of the food composition of the present invention is not particularly limited, and the composition may take any form as long as it can be orally ingested.

Examples thereof include a powder, granule, tablet, hard capsules, soft capsule, liquid (drinks, jelly drinks, and the like), candy, chocolate, and the like, all of which can be produced according to a method known per se in the technical field.

The content of the compound of the present invention in the food composition is appropriately determined to afford an appropriate dose within the indicated range.

The food composition of the present invention can use other food additives as necessary. Examples of such food additives include those generally used as components of health foods such as a fruit juice, dextrin, cyclic oligosaccharide, saccharides (monosaccharides such as fructose, glucose, and the like, and polysaccharides), acidulant, flavor, powdered green tea, and the like, which are used for controlling and improving taste, emulsifier, collagen, whole milk powder, polysaccharide thickener, agar, and the like, which are used for improving texture, and further, vitamins, eggshell calcium, calcium pantothenate, the other minerals, royal jelly, propolis, honey, dietary fiber, Agaricus, chitin, chitosan, flavonoids, carotenoids, lutein, traditional Japanese herbal medicine, chondroitin, various amino acids, and the like.

A production method of the representative compound of the heteroarylcarboxylic acid ester derivatives represented by the formula (I), which is the compound of the present invention, is shown below.

Heteroarylcarboxylic acid ester derivative (H) represented by the formula (I) wherein X is —OR³, and R³ is as previously defined, can be produced as follows.

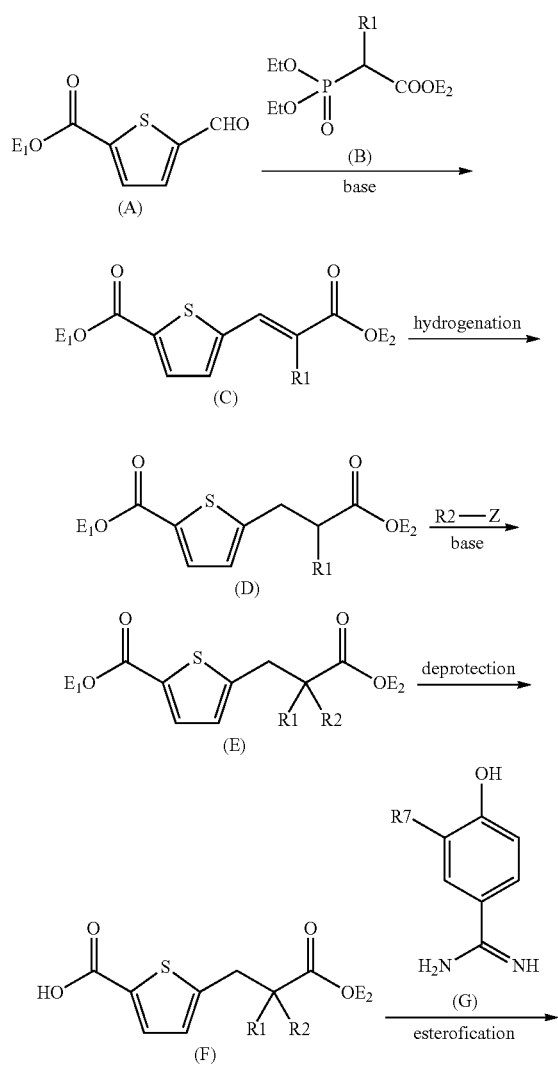

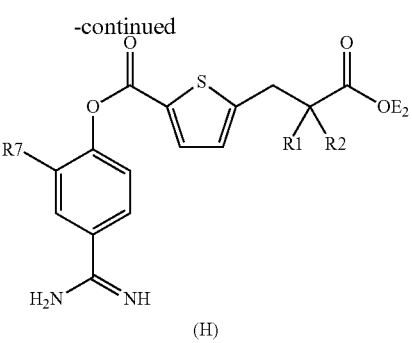

wherein $E_1$ is a protecting group such as a methyl group, an ethyl group, a tert-butyl group, a benzyl group, and the like, $E_2$ is similar to $R^3$, and $R^1$, $R^2$ and $R^7$ are as previously defined.

Alkenylene derivative (C) can be synthesized by reacting aldehyde (A) with Wittig reagent (B) in, for example, a solvent that does not adversely influence the reaction, such as tetrahydrofuran, N,N-dimethylformamide and the like, in the presence of, for example, a base such as sodium hydride and the like. Alkenylene derivative (C) can be converted to alkylene derivative (D) by hydrogenation in the presence of a catalyst, for example, 10% palladium/carbon, palladium hydroxide/carbon, and the like under a hydrogen atmosphere in a solvent that does not adversely influence the reaction, such as ethyl acetate, methanol, tetrahydrofuran, dichloromethane, chloroform and the like.

After converting alkylene derivative (D) into the enolate with a base such as lithium bis(trimethylsilyl)azanide, lithium diisopropylamide, and the like in a solvent, for example tetrahydrofuran, N,N-dimethylformamide, and like, at low temperature, it can be reacted with R2-Z (wherein Z is a leaving group such as an iodine atom, a bromine atom and the like) to can lead to dialkyl derivative (E).

Carboxylic acid derivative (F) can be obtained by deprotecting dialkyl derivative (E) by, for example, hydrolysis with a base such as sodium hydroxide and the like, hydrolysis with an acid such as hydrochloric acid, trifluoroacetic acid and the like or treating with, for example, 10% palladium/carbon and the like under a hydrogen atmosphere.

Heteroarylcarboxylic acid ester derivative (H) can be produced by esterifying carboxylic acid derivative (F) with amidinophenol derivative (G).

The esterification reaction can be performed by a known method which is, for example, (1) a method using an acid halide, (2) a method using a condensation agent and the like.

(1) The method using an acid halide is performed, for example, by reacting an acid chloride obtained by reaction with thionyl chloride, oxalyl chloride, and the like in a solvent that does not adversely influence the reaction, such as dichloromethane, N-methylpyrrolidone, and the like, or without solvent in the presence or absence of, for example, a catalyst such as N,N-dimethylformamide and the like, with the alcohol in a solvent that does not adversely influence the reaction such as dichloromethane, tetrahydrofuran, and the like in the presence of a base such as pyridine and triethylamine.

(2) The method using a condensation agent is performed, for example, by reacting the carboxylic acid with the alcohol in, for example, a solvent that does not adversely influence the reaction such as tetrahydrofuran, N,N-dimethylformamide, dichloromethane, 1,2-dichloloethane, pyridine, and the like in, for example, the presence or absence of a base such as pyridine, triethylamine, and the like, by using a condensation agent such as 1-ethyl-3-(3'-dimethylaminopropyl)carbodiimide (WSC), 1,3-dicyclohexylcarbodiimide, and the like.

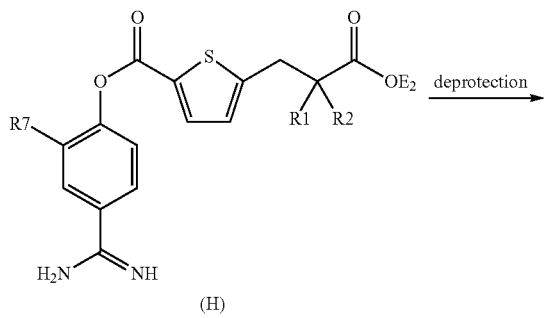

(H)

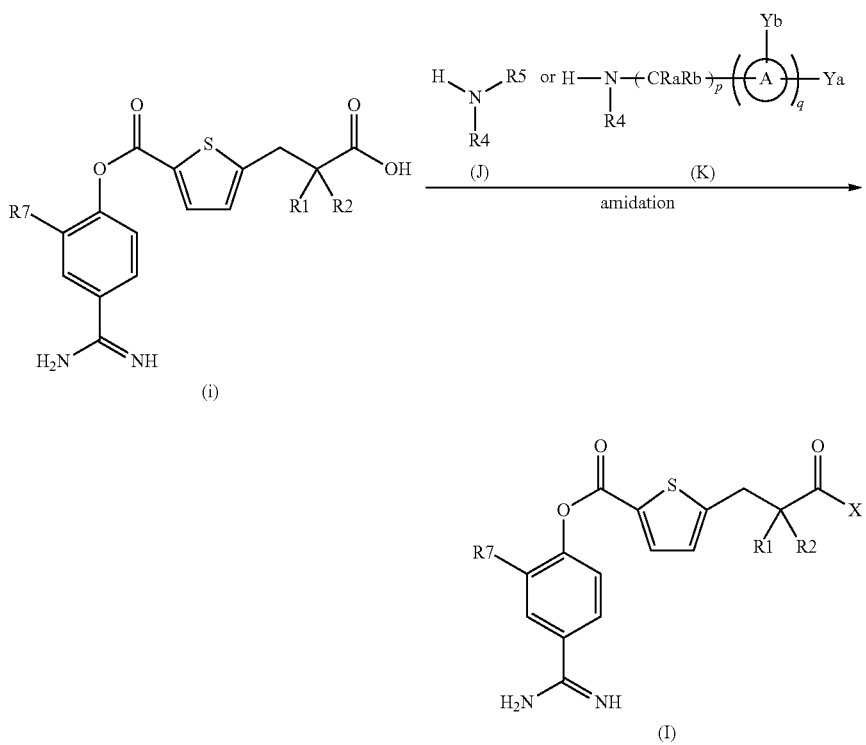

wherein, each symbol is as previously defined, provided, however, that X is other than —OR$^3$.

Heteroarylcarboxylic acid ester derivative (H) can be converted to carboxylic acid derivative (i) in the same manner as in the afore-mentioned deprotection reaction.

Heteroarylcarboxylic acid ester derivative (I) can be produced by amidating carboxylic acid derivative (i) with amine (J) or (K). H—NR$^8$R$^9$ or H—NR$^8$'R$^9$' wherein each symbol is as previously defined, may be instead of amine (J) or (K). The amidation reaction of the carboxylic acid derivative is performed using the corresponding amine instead of an alcohol and in the same manner as in the aforementioned esterification reaction.

Dialkyl derivative (E) can be also synthesized by reacting alpha-dialkyl carboxylic acid (L) with alkyl halide (M) (wherein Z is a leaving group such as a chlorine atom, a bromine atom and the like).

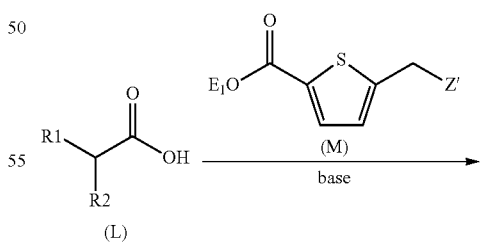

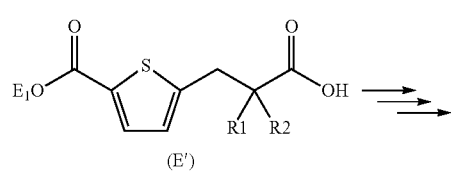

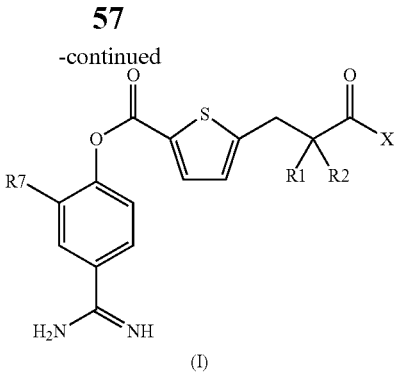

(I)

wherein, each symbol is as previously defined.

After converting alpha-dialkyl carboxyric acid (L) into the enolate with a base such as lithium bis(trimethylsilyl)azanide, lithium diisopropylamide, and the like in a solvent, for example tetrahydrofuran, N,N-dimethylformamide, and like, at low temperature, it can be reacted with alkyl halide (M) and to lead to dialkyl derivative (E').

Dialkyl derivative (E') can be converted to heteroarylcarboxylic acid ester derivative (I) in the same manner as in the afore-mentioned protection, deprotection, esterification, and amidation.

Amines (J) or (K) can be obtained according to the following Examples or any know methods.

Other features of the invention will become apparent in the course of the following descriptions of exemplary embodiments which are given for illustration of the invention and are not intended to be limiting thereof.

EXAMPLES

Example 1

Synthesis of N-[1-{5-(4-amidino-2-fluorophenoxycarbonyl)thiophen-2-ylmethyl}cyclobutylcarbonyl]-L-aspartic acid trifluoroacetic acid salt (compound 1)

Step 1. Synthesis of 3-fluoro-4-hydroxylbenzamidine hydrochloride

To 3-fluoro-4-hydroxybenzonitrile (7.56 g, 55.2 mmol) were added ethanol (20 mL) and 4N-hydrogen chloride in 1,4-dioxane (100 mL), and the mixture was stirred at room temperature. After 5 days, the mixture was concentrated and dried with a vacuum pump. Then, the mixture was dissolved in ethanol (100 mL), ammonium carbonate (11.0 g, 115 mmol) was added, and the mixture was stirred at room temperature. After 12 hours, the solvent was evaporated, and the residue was dissolved in water (100 mL). The mixture was lyophilized to give the title compound (11.2 g, quantitative).

1H-NMR (300 MHz, DMSO-d6) δ 11.28 (1H, br s), 9.19 (2H, br s), 9.02 (2H, br s), 7.75 (1H, dd, J=2.4, 12.0 Hz), 7.59 (1H, m), 7.18 (1H, dd, J=8.4, 8.7 Hz).

MS(ESI) m/z 155(M+H)+

Step 2. Synthesis of 5-formyl-2-thiophencarboxylic acid tert-butyl ester

To a solution of 5-formyl-2-thiophencarboxylic acid (25 g, 0.16 mol) in tert-butyl alcohol (200 mL) and dichloromethane (100 mL) was added di-tert-butyl dicarbonate (41 g, 0.19 mol), N,N-dimethylaminopyridine (2.0 g, 0.016 mol), and pyridine (5 mL), and the mixture was stirred at room temperature for 24 hours. The reaction mixture was concentrated under reduced pressure. The residue was added to ethyl acetate and 0.5N-hydrochloric acid solution, the organic layer was separated, and the aqueous layer was extracted two times with ethyl acetate. The organic layers were combined, washed with 0.5 N sodium hydroxide solution and brine, and dried over anhydrous magnesium sulfate. The solvent of the filtrate after filtration was evaporated under reduced pressure to give the title compound (32.1 g, 0.15 mol, 94%).

$^1$H-NMR (400 MHz, CDCl$_3$) δ 9.95 (1H, s), 7.75 (1H, d, J=4.0 Hz), 7.70 (1H, d, J=4.0 Hz), 1.59 (9H, s).

Step 3. Synthesis of 5-chloromethyl-2-thiophencarboxylic acid tert-butyl ester

To a solution of 5-formyl-2-thiophencarboxylic acid tert-butyl ester (5 g, 23.6 mmol) in tetrahydrofuran (50 mL) and methanol (5 mL), was added sodium borohydride (0.50 g, 13.0 mmol) at 0° C., and the mixture was stirred for 2 hours at room temperature. The reaction mixture was partitioned between ethyl acetate and 0.5N-hydrochloric acid solution. The aqueous layer was extracted with ethyl acetate, and the combined organic layers were washed with brine and dried over anhydrous magnesium sulfate. The solvent was removed under reduced pressure, and the obtained residue was dissolved in dichloromethane (100 mL), methanesulfonyl chloride (1.9 ml, 24 mmol) and diisopropylethylamine (5.7 ml, 33 mmol) were added at 0° C., and the mixture was stirred at room temperature overnight. The solvent was evaporated under reduced pressure, 0.5N-hydrochloric acid solution was added to the residue, and the mixture was extracted with ethyl acetate. The extract was washed with brine, dried over anhydrous magnesium sulfate, and concentrated under reduced pressure. The obtained residue was purified by silica gel column chromatography to give the title compound (5.3 g, 23 mmol).

$^1$H NMR (400 MHz, CDCl$_3$) δ 7.56 (1H, d, J=3.8 Hz), 7.03 (1H, d, J=3.8 Hz), 4.75 (2H, s), 1.57 (9H, s).

Step 4. Synthesis of 1-{5-(tert-butoxycarbonyl)thiophen-2-ylmethyl}cyclobutylcarboxylic acid To a solution of diisopropylamine (905 µL, 6.44 mmol) in tetrahydrofuran (0.5 mL), was added n-butyllithium (3.9 mL, 1.65 M in hexane) at −78° C. After stirring at 0° C. for 25 minutes, a mixture was cooled to −78° C. Cyclobutylcarboxylic acid (372 µL, 3.58 mmol) was added to the reaction mixture, and stirred at room temperature for 15 minutes. After cooled to −78° C., 5-chloromethyl-2-thiophencarboxylic acid tert-butyl ester obtained in step 3 (333 mg, 1.43 mmol) in tetrahydrofuran (0.5 mL) was added to the reaction mixture. After stirred at room temperature for 2 hours, the reaction mixture was partitioned between ethyl acetate and 1N-hydrochloric acid solution. The aqueous layer was extracted with ethyl acetate, and the combined organic layers were washed with brine and dried over anhydrous magnesium sulfate. The solvent was removed under reduced pressure, and the obtained residue was purified by high performance liquid chromatography (water-acetonitrile, each containing 0.1% trifluoroacetic acid) to give the title compound (60 mg, 0.201 mmol, 14%).

1H-NMR (400 MHz, CDCl$_3$) δ 7.53 (1H, d, J=3.7 Hz), 6.79 (1H, d, J=3.7 Hz), 3.30 (2H, s), 2.63-2.47 (2H, m), 2.18-2.05 (2H, m), 2.05-1.88 (2H, m), 1.53 (9H, s).

MS(ESI) m/z 297 (M+H)+

Step 5. Synthesis of N-{1-(5-carboxylthiophen-2-ylmethyl)cyclobutylcarbonyl}-L-aspartic acid dimethyl ester 3-{5-(tert-butylcarboxyl)thiophen-2-yl}-2-cyclobutylpropanoic acid (50 mg, 0.169 mmol) was solved in sulfonyl chloride (0.5 mL), and stirred at 60° C. for 30 minutes. After the solvent was removed under reduced pressure, to a solution of the product obtained in step 4 in dichloromethane (0.3 mL) was added L-aspartic acid dimethyl ester (50 mg, 0.253 mmol), and pyridine (0.3 mL). After the reaction mixture was stirred at room temperature for 1 hour, WSC hydrochloride (60 mg, 0.338=1) was added and stirred at room temperature for 3 hours. After the solvent was removed under reduced pressure, the residue was resolved in trifluoroacetic acid (0.5 mL). After the solution was stirred at room temperature for 1 hour, the reaction mixture was concentrated under reduced pressure. The obtained residue was purified by high performance liquid chromatography (water-acetonitrile, each containing 0.1% trifluoroacetic acid) to give the title compound (32 mg, 0.093 mmol, 55%).

1H-NMR (400 MHz, DMSO-d6) δ 8.18 (1H, d, J=7.9 Hz), 7.52 (1H, d, J=3.7 Hz), 6.85 (1H, d, J=3.7 Hz), 4.72-4.53 (1H, m), 3.61 (3H, s), 3.60 (3H, s), 3.28 (2H, s), 2.84 (1H, dd, J=16.2, 6.2 Hz), 2.66 (1H, dd, J=16.2, 7.9 Hz), 2.39-2.20 (2H, m), 2.01-1.78 (3H, m), 1.77-1.63 (1H, m).
MS(ESI) m/z 384 (M+H)+

Step 6. Synthesis of N-[1-{5-(4-amidino-2-fluorophenoxycarbonyl)thiophen-2-ylmethyl}cyclobutylcarbonyl]-L-aspartic acid trifluoroacetic acid salt (compound 1)

To a solution of N-{3-(5-carboxylthiophen-2-yl)-2-cyclobutylpropanoyl}-L-aspartic acid dimethyl ester (30 mg, 0.087 mmol) in pyridine (1.0 mL), was added 3-fluoro-4-hydroxylbenzamidine hydrochloride (25 mg, 0.131 mmol) and WSC hydrochloride (34 mg, 0.175 mmol), and the mixture was stirred at room temperature overnight. After the solvent was removed under reduced pressure, the obtained residue was dissolved in 4N-hydrogen chloride in 1,4-dioxane (0.6 mL) and water (0.2 mL). After the reaction mixture was stirred at 60° C. for 9 hours, the reaction mixture was concentrated under reduced pressure. The obtained residue was purified by high performance liquid chromatography (water-acetonitrile, each containing 0.1% trifluoroacetic acid) to give the title compound (18 mg, 0.030 mmol, 34%).

1H-NMR (400 MHz, DMSO-d6) δ 9.42 (2H, br s), 9.09 (2H, br s), 8.07 (1H, d, J=8.0 Hz), 7.99-7.83 (2H, m), 7.92-7.82 (1H, m), 7.79-7.69 (2H, m), 7.06 (1H, d, J=3.9 Hz), 4.56 (1H, dd, J=13.9, 7.6 Hz), 3.48 (2H, s), 2.74 (1H, dd, J=16.4, 6.0 Hz), 2.64-2.49 (1H, m), 2.40-2.25 (2H, m), 2.05-1.83 (3H, m), 1.80-1.69 (1H, m).
MS(ESI) m/z 492 (M+H)+

Example 2

Synthesis of N-{1-[5-(4-amidino-2-fluorophenoxycarbonyl)thiophen-2-ylmethyl]cyclopentylcarbonyl}-L-aspartic acid trifluoroacetic acid salt (compound 2)

The compound 2 was synthesized by an operation in the same manner as in the above-mentioned Example 1.
1H-NMR (400 MHz, DMSO-d6) δ 9.36 (2H, br s), 9.08 (2H, br s), 7.97 (1H, d, J=7.9 Hz), 7.89-7.80 (2H, m), 7.72-7.63 (2H, m), 7.00 (1H, d, J=3.9 Hz), 4.49 (2H, dt, J=12.9, 6.4 Hz), 3.17 (2H, s), 2.69 (1H, dd, J=16.4, 6.0 Hz), 2.57-2.45 (2H, m), 2.02-1.81 (2H, m), 1.63-1.37 (6H, m).
MS(ESI) m/z 506 (M+H)+

Example 3

Synthesis of N-{3-[5-(4-amidino-2-fluorophenoxycarbonyl)thiophen-2-yl]-2,2-dimethylpropionyl}-L-valine hydrochloride (compound 9)

Step 1. Synthesis of 2-(diethylphosphono)propanoic acid methyl ester

Methyl 2-bromopropionate (100 g, 0.60 mol) and triethylphosphite (109 g, 0.66 mol) were mixed, and the mixture was stirred at 110° C. for 2 days. The reaction mixture was dried under reduced pressure to give the title compound.

Step 2. Synthesis of 5-[(1E)-2-(methoxycarbonyl)-prop-1-en-1-yl]thiophene-2-carboxylic acid tert-butyl ester 2-(Diethylphosphono)propanoic acid methyl ester (23.0 g, 0.103 mol) was dissolved in tetrahydrofuran (150 mL), 60% sodium hydride (2.4 g, 0.06 mol) was added at 0° C., and the mixture was stirred for 30 minutes. To the reaction mixture was added a solution of 5-formyl-2-thiophenecarboxylic acid tert-butyl ester obtained in Example 1, step 2 (11.0 g, 0.052 mol) in tetrahydrofuran (10 mL), and the mixture was stirred at room temperature overnight. The solvent was evaporated, and the residue was partitioned between ethyl acetate and 1N-hydrochloric acid solution, and washed successively with water and brine. After drying over anhydrous magnesium sulfate, the residue was purified by silica gel column chromatography to give the title compound (13.1 g, 0.047 mol, 90%).
$^1$H-NMR (400 MHz, CDCl$_3$) δ 7.89 (1H, s), 7.68 (1H, d, J=4.0 Hz), 7.19 (1H, d, J=4.0 Hz), 3.82 (3H, s), 2.24 (3H, s), 1.59 (9H, s).

Step 3. Synthesis of 5-(2-methoxycarbonylpropyl)thiophene-2-carboxylic acid tert-butyl ester 5-[(1E)-2-(methoxycarbonyl)-prop-1-en-1-yl]thiophene-2-carboxylic acid tert-butyl ester (13.77 g, 0.049 mol) was dissolved in ethyl acetate (60 mL), methanol (20 mL), and chloroform (10 mL), palladium hydroxide (2.8 g) was added, and the mixture was stirred at room temperature overnight under a hydrogen atmosphere. After completion of the reaction, palladium hydroxide was removed by celite filtration, and the solvent was evaporated under reduced pressure to give the title compound (13.14 g, 0.046 mol, 94%).
$^1$H-NMR (400 MHz, CDCl$_3$) δ 7.53 (1H, d, J=4.0 Hz), 6.77 (1H, d, J=4.0 Hz), 3.67 (3H, s), 3.18 (1H, dd, J=14.4, 7.2 Hz), 2.91 (1H, dd, J=14.4, 7.2 Hz), 2.77 (1H, m), 1.56 (9H, s), 1.21 (3H, d, J=7.2 Hz).

Step 4. Synthesis of 5-(2-methyl-2-methoxycarbonylpropyl)thiophene-2-carboxylic acid tert-butyl ester 5-(2-Methoxycarbonylpropyl)thiophene-2-carboxylic acid tert-butyl ester (13.14 g, 46.3 mmol) was dissolved in tetrahydrofuran (250 mL), 1.09 M lithium bis(trimethylsilyl)azanide/tetrahydrofuran solution (65 mL, 70.9 mmol) was added dropwise at −78° C., and the mixture was stirred for 2 hours. To the reaction mixture was added methyl iodide (11.7 g, 82.4 mmol) at −78° C., and the mixture was stirred at room temperature overnight. The reaction mixture was concentrated under reduced pressure. The residue was added to ethyl acetate and 0.5N-hydrochloric acid solution, the organic layer was separated, and the aqueous layer was extracted two times with ethyl acetate. The organic layers were combined, washed with sodium thiosulfate solution and brine, and dried over anhydrous magnesium sulfate. The solvent of the filtrate after filtration was evaporated under reduced pressure. The obtained residue was purified by silica gel column chromatography to give the title compound (12.36 g, 41.4 mmol, 89%).

$^1$H-NMR (400 MHz, CDCl$_3$) δ 7.53 (1H, d, J=3.6 Hz), 6.73 (1H, d, J=3.6 Hz), 3.71 (3H, s), 3.05 (2H, s), 1.56 (9H, s), 1.23 (6H, s).

Step 5. Synthesis of 3-[5-(4-amidino-2-fluorophenoxycarbonyl)thiophen-2-yl]-2,2-dimethylpropanoic acid trifluoroacetic acid salt To 5-(2-Methyl-2-methoxycarbonylpropyl)thiophene-2-carboxylic acid tert-butyl ester (5.0 g, 16.8 mmol) was added trifluoroacetic acid (20 mL), and the mixture was stirred at room temperature for 30 minutes. The solvent was evaporated, and the residue was dissolved in pyridine (30 mL), 3-fluoro-4-hydroxybenzamidine hydrochloride (3.2 g, 16.8 mmol) and WSC hydrochloride (3.8 g, 19.8 mmol) were added, and the mixture was stirred at 50° C. for 5 hours. The reaction mixture was concentrated under reduced pressure, 4N-hydrochloric acid solution (10 mL) and 4N-Hydrogen chloride in 1,4-Dioxane (10 mL) were added to the obtained residue, and the mixture was stirred at 80° C. for 2 hours. The reaction mixture was concentrated under reduced pressure, and the obtained residue was purified by high performance liquid chromatography (water-acetonitrile, each containing 0.1% trifluoroacetic acid) to give the title compound (2.8 g, 5.86 mmol, 35%).

$^1$H-NMR (400 MHz, DMSO-d6) δ 9.41 (2H, br s), 9.10 (2H, br s), 7.96 (1H, d, J=4.0 Hz), 7.93 (1H, d, J=8.1 Hz), 7.80-7.70 (2H, m), 7.09 (1H, d, J=4.0 Hz), 3.14 (2H, s), 1.16 (6H, s).

MS(ESI) m/z 365(M+H)+

Step 6. Synthesis of N-{3-[5-(4-amidino-2-fluorophenoxycarbonyl)thiophen-2-yl]-2,2-dimethylpropionyl}-L-valine hydrochloride (compound 9)

3-[5-(4-Amidino-2-fluorophenoxycarbonyl)thiophen-2-yl]-2,2-dimethylpropanoic acid trifluoroacetic acid salt obtained in step 5 (53 mg, 0.10 mmol) was dissolved in thionyl chloride (3 mL), and the mixture was stirred at room temperature for 3 hours. Thionyl chloride was evaporated under reduced pressure to give the acid chloride. The obtained acid chloride was dissolved in dichloromethane (3 mL), L-valine tert-butyl ester hydrochloride (25 mg, 0.12 mmol) and pyridine (0.1 mL) were added thereto, and the mixture was stirred at room temperature overnight. After evaporation of the solvent, trifluoroacetic acid (2 mL) was added, and the mixture was stirred at room temperature 1 hour. The mixture was concentrated under reduced pressure. The obtained residue was purified by high performance liquid chromatography (water-acetonitrile, each containing 0.1% trifluoroacetic acid) to give the trifluoroacetic acid salt of the title compound.

To the obtained trifluoroacetic acid salt was added 0.05N-hydrochloric acid solution (10 mL), and the mixture was lyophilized to give the title compound (40 mg, 0.80 mmol, 80%).

$^1$H-NMR (400 MHz, DMSO-d6) δ 9.41 (2H, br s), 9.10 (2H, br s), 8.00-7.89 (2H, m), 7.80-7.70 (2H, m), 7.57 (1H, d, J=7.2 Hz), 7.08 (1H, s), 4.13 (1H, m), 3.21 (1H, d, J=16.0 Hz), 3.15 (1H, d, J=16.0 Hz), 2.15-2.05 (1H, m), 1.76-1.50 (4H, m), 0.90 (3H, d, J=6.8 Hz), 0.86-0.75 (6H, m).

MS(ESI) m/z 464 (M+H)+

Example 4

Synthesis of N-{3-[5-(4-amidino-2-fluorophenoxycarbonyl)thiophen-2-yl]-2,2-dimethylpropionyl}-N-propylglycine hydrochloride (compound 10)

Step 1. Synthesis of N-allylglycine benzyl ester hydrochloride

To a solution of allylamine hydrochloride (5.0 g, 53.4 mmol) in tetrahydrofuran (100 mL) was added diisopropylethylamine (10 mL) and bromoacetic acid benzyl ester (3.06 g, 13.3 mmol) at 0° C. and the mixture was stirred at room temperature overnight. The reaction mixture was concentrated under reduced pressure. The residue was added ethyl acetate and 1 N-hydrochloric acid solution, the organic layer was separated, and the aqueous layer was extracted two times with ethyl acetate. The organic layers were combined, washed with sodium thiosulfate solution and brine, and dried over anhydrous magnesium sulfate and concentrated under reduced pressure. The obtained residue was purified by silica gel column chromatography, and to the obtained oil was added 4N-Hydrogen chloride in 1,4-Dioxane (3.5 mL). The mixture was concentrated under reduced pressure and lyophilized to give the title compound (2.12 g, 8.79 mmol, 66%).

$^1$H-NMR (400 MHz, CDCl$_3$) δ 7.40-7.35 (5H, m), 6.12-6.02 (1H, m), 5.49-5.43 (2H, m), 5.22 (2H, s), 3.82 (2H, s), 3.78 (2H, d, J=7.2 Hz).

MS(ESI) m/z 206(M+H)+

Step 2. Synthesis of N-{3-[5-(4-amidino-2-fluorophenoxycarbonyl)thiophen-2-yl]-2,2-dimethylpropionyl}-N-allylglycine benzyl ester trifluoroacetic acid salt 3-[5-(4-Amidino-2-fluorophenoxycarbonyl)thiophen-2-yl]-2,2-dimethylpropanoic acid trifluoroacetic acid salt (100 mg, 0.20 mmol) obtained in Example 3, step 5 was dissolved in thionyl chloride (3 mL), and the mixture was stirred at 60° C. for 20 minutes. Thionyl chloride was evaporated under reduced pressure to give the acid chloride. The obtained acid chloride was dissolved in dichloromethane (5 mL), N-allylglycine benzyl ester hydrochloride obtained in step 1 (51 mg, 0.21 mmol) and pyridine (0.1 mL) were added thereto, and the mixture was stirred at room temperature overnight. The mixture was concentrated under reduced pressure. The obtained residue was purified by high performance liquid chromatography (water-acetonitrile, each containing 0.1% trifluoroacetic acid) to give the title compound. (37 mg, 0.056 mmol, 28%).

$^1$H-NMR (400 MHz, DMSO-d6) δ 9.40 (2H, br s), 9.05 (2H, br s), 7.90 (2H, m), 7.72 (2H, m), 7.38-7.28 (5H, m), 7.11 (1H, d, J=4.0 Hz), 5.86-5.73 (1H, m), 5.25-5.15 (2H, m), 5.12 (2H, s), 4.28-4.18 (2H, m), 4.01-4.91 (2H, s), 3.19 (2H, s), 1.23 (6H, s).

MS(ESI) m/z 552 (M+H)+

Step 3. Synthesis of N-{3-[5-(4-amidino-2-fluorophenoxycarbonyl)thiophen-2-yl]-2,2-dimethylpropionyl}-N-propylglycine hydrochloride (compound 10)

N-{3-[5-(4-Amidino-2-fluorophenoxycarbonyl)thiophen-2-yl]-2,2-dimethylpropionyl}-N-allylglycine benzyl ester trifluoroacetic acid salt (1.94 g, 2.91 mmol) was dissolved in ethanol (40 mL) and water (10 mL), palladium hydroxide (0.4 g) was added, and the mixture was stirred at room temperature for 6 hours under a hydrogen atmosphere. The reaction mixture was filtered through celite, and the filtrate was concentrated under reduced pressure. To the obtained residue was added 0.01N-hydrochloric acid solution (250 mL), and the mixture was lyophilized to give the title compound (1.19 g, 2.02 mmol, 70%).

$^1$H-NMR (400 MHz, DMSO-d6) δ 9.41 (2H, br s), 9.05 (2H, br s), 7.93 (2H, m), 7.74 (2H, m), 7.11 (1H, d, J=3.6 Hz), 3.75-3.65 (2H, m), 3.18 (2H, s), 1.58-1.48 (2H, m), 1.25 (6H, br s), 0.84 (3H, m).
MS(ESI) m/z 464 (M+H)+

Example 5

Synthesis of 3-[5-(4-amidino-2-fluorophenoxycarbonyl)thiophen-2-yl]-2,2-diethylpropanoic acid trifluoroacetic acid salt (compound 18)

Step 1. Synthesis of 2-(diethylphosphono)butyric acid methyl ester

Methyl 2-bromobutanoate (92 g, 0.508 mol) and triethylphosphite (95 g, 0.57 mol) were mixed, and the mixture was stirred at 110° C. for 3 days. The reaction mixture was dried under reduced pressure to give the title compound.

$^1$H-NMR (400 MHz, CDCl$_3$) δ 4.20-4.05 (4H, m), 3.76 (3H, s), 2.88 (1H, ddd, J=22.4, 10.4, 4.0 Hz), 2.18-1.98 (2H, m), 1.35-1.30 (6H, m), 1.19 (3H, t, J=8.0 Hz).

Step 2. Synthesis of 5-[(1E)-2-(methoxycarbonyl)-but-1-en-1-yl]thiophene-2-carboxylic acid tert-butyl ester 2-(Diethylphosphono)butyric acid methyl ester (46 g, 0.193 mol) was dissolved in tetrahydrofuran (300 mL), 60% sodium hydride (6.6 g, 0.165 mol) was added at 0° C., and the mixture was stirred for 30 minutes. To the reaction mixture was added a solution of 5-formyl-2-thiophenecarboxylic acid tert-butyl ester obtained in Example 1, step 2 (32.1 g, 0.15 mol) in tetrahydrofuran (10 mL), and the mixture was stirred at room temperature for 2 hours. The solvent was evaporated, and the residue was partitioned between ethyl acetate and 1N-hydrochloric acid solution, and washed successively with water and brine. After drying over anhydrous magnesium sulfate, the residue was purified by silica gel column chromatography to give the title compound (35.6 g, 0.12 mol, 80%).

$^1$H-NMR (400 MHz, CDCl$_3$) δ 7.71 (1H, s), 7.65 (1H, d, J=4.0 Hz), 7.17 (1H, d, J=4.0 Hz), 3.82 (3H, s), 2.73 (2H, q, J=7.6 Hz), 1.56 (9H, s), 1.18 (3H, t, J=7.6 Hz).

Step 3. Synthesis of (E)-3-(5-tert-butoxycarbonylthiophen-2-yl)-2-ethylpropenoic acid 5-[(1E)-2-(Methoxycarbonyl)-but-1-en-1-yl]thiophene-2-carboxylic acid tert-butyl ester (34.6 g, 120 mol) was dissolved in tetrahydrofuran (150 mL), and methanol (60 mL), 1 N lithium hydroxide solution (144 mL, 144 mmol) was added, and the mixture was stirred at room temperature for 2 days. The mixture was concentrated under reduced pressure. 0.5 N-Hydrochloric acid solution and ethyl acetate were added to the obtained residue, the organic layer was separated, and the aqueous layer was extracted three times with ethyl acetate. The organic layers were combined, washed with brine, and dried over anhydrous magnesium sulfate. After filtration, the solvent of the filtrate was evaporated under reduced pressure to give the title compound (32.2 g, 114 mmol, 95%).

$^1$H-NMR (400 MHz, CDCl$_3$) δ 7.82 (1H, s), 7.66 (1H, d, J=4.0 Hz), 7.21 (1H, d, J=4.0 Hz), 2.74 (2H, q, J=7.6 Hz), 1.59 (9H, s), 1.21 (3H, t, J=7.6 Hz).

Step 4. Synthesis of 2-((5-tert-butoxycarbonylthiophen-2-yl)methyl)butanoic acid (E)-3-(5-tert-butoxycarbonylthiophen-2-yl)-2-ethylpropenoic acid (20.43 g, 72.4 mmol) was dissolved in ethyl acetate (300 mL), methanol (20 mL) and chloroform (10 mL), palladium hydroxide (2.0 g) was added, and the mixture was stirred at room temperature overnight under a hydrogen atmosphere. After completion of the reaction, palladium hydroxide was removed by celite filtration, and the solvent was evaporated under reduced pressure to give the title compound (20.6 g, quantitative).

Step 5. Synthesis of 5-(2-benzyloxycarbonylbutyl)thiophene-2-carboxylic acid tert-butyl ester 2-(5-tert-Butoxycarbonylthiophen-2-yl)methyl-butanoic acid (20.6 g, 72.2 mmol) was dissolved in N,N-dimethylformamide (100 mL), potassium carbonate (10.4 g, 75.3 mmol) and benzyl bromide (13.0 g, 76.0 mmol) were added, and the mixture was stirred at room temperature overnight. The reaction mixture was filtered through celite, and the filtrate was concentrated under reduced pressure. 0.5 N-Hydrochloric acid solution and ethyl acetate were added to the obtained residue, the organic layer was separated, and the aqueous layer was extracted three times with ethyl acetate. The organic layers were combined, washed with brine, and dried over anhydrous magnesium sulfate. After filtration, the solvent of the filtrate was evaporated under reduced pressure. The obtained residue was purified by silica gel column chromatography to give the title compound (27.0 g, 72.1 mmol, 96%).

$^1$H-NMR (400 MHz, CDCl$_3$) δ 7.49 (1H, d, J=3.6 Hz), 7.35-7.25 (5H, m), 6.71 (1H, d, J=3.6 Hz), 5.11 (1H, d, J=12.4 Hz), 5.07 (1H, d, J=12.4 Hz), 3.16 (1H, dd, J=14.8, 8.8 Hz), 2.96 (1H, dd, J=14.8, 6.0 Hz), 2.72 (1H, m), 1.73-1.60 (2H, m), 1.56 (9H, s), 0.92 (3H, t, J=7.6 Hz).

Step 6. Synthesis of 5-(2-benzyloxycarbonyl-2-ethylbutyl)thiophene-2-carboxylic acid tert-butyl ester 5-(2-Benzyloxycarbonylbutyl)thiophene-2-carboxylic acid tert-butyl ester (29.5 g, 78.8 mmol) was dissolved in tetrahydrofuran (200 mL), 1.09 M lithium bis(trimethylsilyl)azanide/tetrahydrofuran solution (94 mL, 102 mmol) was added dropwise at −78° C., and the mixture was stirred for 2 hours. To the reaction mixture was added ethyl iodide (12.3 g, 156 mmol) at −78° C., and the mixture was stirred at room temperature overnight. The reaction mixture was concentrated under reduced pressure. The residue was added to ethyl acetate and 0.5 N-hydrochloric acid solution, the organic layer was separated, and the aqueous layer was extracted two times with ethyl acetate. The organic layers were combined, washed with sodium thiosulfate solution and brine, and dried over anhydrous magnesium sulfate, and concentrated under reduced pressure. The obtained residue was purified by silica gel column chromatography to give the title compound (24.9 g, 61.9 mmol, 78%).

$^1$H-NMR (400 MHz, CDCl$_3$) δ 7.49 (1H, d, J=4.0 Hz), 7.40-7.30 (5H, m), 6.67 (1H, d, J=4.0 Hz), 5.15 (2H, s), 3.11 (2H, s), 1.70-1.59 (4H, m), 1.56 (9H, s), 0.85 (6H, t, J=7.6 Hz).

Step 7. Synthesis of 5-(2-benzyloxycarbonyl-2-ethyl-butyl)thiophene-2-carboxylic acid To 5-(2-benzyloxycarbonyl-2-ethylbutyl)thiophene-2-carboxylic acid tert-butyl ester (24.9 g, 61.9 mmol) was added trifluoroacetic acid (20 mL), and the mixture was stirred at room temperature for 2 hours. The solvent was evaporated to give the title compound (quantitative).

Step 8. Synthesis of 3-[5-(4-amidino-2-fluorophenoxycarbonyl)thiophen-2-yl]-2,2-diethylpropanoic acid benzyl ester trifluoroacetic acid salt 5-(2-Benzyloxycarbonyl-2-ethyl-butyl)thiophene-2-carboxylic acid (5.0 g, 14.4 mmol) was dissolved in N-methylpyrrolidone (5 mL), and dichloromethane (5 mL), thionylchloride (1.27 mL, 17.6 mmol) was added at 0° C., and the mixture was stirred for 15 minutes at 0° C. 3-fluoro-4-hydroxybenzamidine hydrochloride (2.7 g, 14.2 mmol) and pyridine (7 mL) were added to the reaction mixture, and the mixture was stirred for 2 hours at room temperature. The reaction mixture was concentrated under reduced pressure, and the obtained residue was purified by high performance liquid chromatography (water-acetonitrile, each containing 0.1% trifluoroacetic acid) to give the title compound (4.3 g, 7.21 mmol, 51%).

MS(ESI) m/z 483(M+H)+

Step 9. Synthesis of 3-[5-(4-amidino-2-fluorophenoxycarbonyl)thiophen-2-yl]-2,2-diethylpropanoic acid trifluoroacetic acid salt (compound 18)

3-[5-(4-Amidino-2-fluorophenoxycarbonyl)thiophen-2-yl]-2,2-diethylpropanoic acid benzyl ester trifluoroacetic acid salt (4.3 g, 7.21 mmol) was dissolved in 2-propanol (160 mL) and water (40 mL), palladium hydroxide (0.9 g) was added, and the mixture was stirred at room temperature overnight under a hydrogen atmosphere. The reaction mixture was filtered through celite, and the filtrate was concentrated under reduced pressure. Water and acetonitrile was added to the residue, the mixture was lyophilized to give the title compound (3.61 g, 7.12 mmol, 99%).

$^1$H-NMR (400 MHz, DMSO-d6) δ 9.42 (2H, br s), 9.24 (2H, br s), 7.97 (1H, d, J=4.0 Hz), 7.94 (1H, d, J=10.4 Hz), 7.80-7.70 (2H, m), 7.10 (1H, d, J=4.0 Hz), 3.15 (2H, s), 1.60-1.40 (4H, m), 0.85 (6H, t, J=7.6 Hz).
MS(ESI) m/z 393(M+H)+

Example 6

Synthesis of N-{3-[5-(4-amidino-2-fluorophenoxycarbonyl)thiophen-2-yl]-2,2-diethylpropionyl}-L-serine hydrochloride (compound 11)

3-[5-(4-Amidino-2-fluorophenoxycarbonyl)thiophen-2-yl]-2,2-diethylpropanoic acid trifluoroacetic acid salt (compound 18) (616 mg, 1.2 mmol) was dissolved in thionyl chloride (6 mL), and the mixture was stirred at 60° C. for 20 minutes. Thionyl chloride was evaporated under reduced pressure to give the acid chloride. The obtained acid chloride was dissolved in dichloromethane (20 mL), O-tert-butyl-L-serine tert-butyl ester hydrochloride (334 mg, 1.32 mmol) and pyridine (0.5 mL) were added thereto, and the mixture was stirred at room temperature overnight. After evaporation of the solvent, trifluoroacetic acid (5 mL) was added, and the mixture was stirred at room temperature for 30 minutes. The mixture was concentrated under reduced pressure. The obtained residue was purified by high performance liquid chromatography (water-acetonitrile, each containing 0.1% trifluoroacetic acid) to give the trifluoroacetic acid salt of the title compound.

To the obtained trifluoroacetic acid salt was added 0.05 N-hydrochloric acid solution (30 mL), and the mixture was lyophilized to give the title compound (513 mg, 0.99 mmol, 83%).

$^1$H-NMR (400 MHz, DMSO-d6) δ 9.41 (2H, br s), 9.10 (2H, br s), 7.95-7.90 (2H, m), 7.78-7.72 (2H, m), 7.63 (1H, d, J=7.6 Hz), 7.10 (1H, d, J=4.0 Hz), 4.34 (1H, m), 3.75-3.64 (1H, m), 3.64-3.56 (1H, m), 3.16 (2H, s), 1.62-1.46 (4H, m), 0.88-0.78 (6H, m).

MS(ESI) m/z 480 (M+H)+

Example 7

Synthesis of N-{3-[5-(4-amidino-2-fluorophenoxycarbonyl)thiophen-2-yl]-2,2-diethylpropionyl}-sarcosine hydrochloride (compound 21)

Step 1. Synthesis of N-{3-[5-(4-amidino-2-fluorophenoxycarbonyl)thiophen-2-yl]-2,2-diethylpropionyl}-sarcosine benzyl ester trifluoroacetic acid salt 3-[5-(4-Amidino-2-fluorophenoxycarbonyl)thiophen-2-yl]-2,2-diethylpropanoic acid trifluoroacetic acid salt (compound 18) (100 mg, 0.20 mmol) was dissolved in thionyl chloride (2 mL), and the mixture was stirred at room temperature for 30 minutes. Thionyl chloride was evaporated under reduced pressure to give the acid chloride. The obtained acid chloride was dissolved in 1,2-dichloroethane (5 mL), sarcosine benzyl ester hydrochloride (47 mg, 0.22 mmol) and pyridine (0.2 mL) were added thereto, and the mixture was stirred at 60° C. for 5 hours. The mixture was concentrated under reduced pressure. The obtained residue was purified by high performance liquid chromatography (water-acetonitrile, each containing 0.1% trifluoroacetic acid) to give the title compound (83 mg, 0.12 mmol, 62%).

Step 2. Synthesis of N-{3-[5-(4-amidino-2-fluorophenoxycarbonyl)thiophen-2-yl]-2,2-diethylpropionyl}-sarcosine hydrochloride (compound 21)

N-{3-[5-(4-amidino-2-fluorophenoxycarbonyl)thiophen-2-yl]-2,2-diethylpropionyl}-sarcosine benzyl ester trifluoroacetic acid salt (83 mg, 0.12 mmol) was dissolved in 2-propanol (5 mL) and water (5 mL), palladium hydroxide (50 mg) was added, and the mixture was stirred at room temperature for 2 hours under a hydrogen atmosphere. The mixture was concentrated under reduced pressure. The obtained residue was purified by high performance liquid chromatography (water-acetonitrile, each containing 0.1% trifluoroacetic acid) to give the trifluoroacetic acid salt of the title compound. To the obtained trifluoroacetic acid salt were added 0.01N-hydrochloric acid solution (30 mL), and the mixture was lyophilized to give the title compound (32 mg, 0.064 mmol, 53%).

1H-NMR (400 MHz, DMSO-d6) δ 9.35 (2H, br s), 9.22 (2H, br s), 7.90-7.85 (2H, m), 7.70-7.65 (2H, m), 7.06 (1H, d, J=3.6 Hz), 3.92 (2H, m), 3.15 (3H, s), 3.12 (2H, br s), 1.70-1.60 (2H, m), 1.60-1.50 (2H, m), 0.76 (6H, t, J=7.2 Hz).

MS(ESI) m/z 464 (M+H)+

Example 8

Synthesis of N-allyl-N-{3-[5-(4-amidino-2-fluorophenoxycarbonyl)-thiophen-2-yl]-2,2-dimethylpropionyl}taurine (compound 23)

Step 1. Synthesis of N-allyltaurine isopropyl ester

2-Chloroethylsulfonyl chloride (2 g, 12.3 mmol) was is dissolved in 2-propanol (20 mL), pyridine (2.7 mL) was added, and the mixture was stirred at room temperature for 3 hours. Allylamine hydrochloride (1.15 g, 12.3 mmol) and diisopropylethylamine (6.4 mL) was added, and stirred at room temperature for 3 hours. The reaction mixture was evaporated under reduced pressure, 5% sodium bicarbonate solution was added to the residue, and the mixture was extracted with ethyl acetate. The extract was washed with brine, dried over anhydrous magnesium sulfate and concentrated under reduced pressure. The obtained residue was purified by silica gel column chromatography to give the title compound (0.5 g, 2.4 mmol, 20%).

¹H-NMR (400 MHz, CDCl₃) δ 6.55 (1H, dd, J=10.0, 16.8 Hz), 6.39 (1H, d, J=16.8 Hz), 6.07 (1H, d, J=10.0 Hz), 4.81 (1H, sep, J=6.3 Hz), 1.40 (6H, d, J=6.3 Hz).

MS(ESI) m/z 208 (M+H)+

Step 2. Synthesis of N-allyl-N-{3-[5-(4-amidino-2-fluorophenoxycarbonyl)thiophen-2-yl]-2,2-dimethylpropionyl}taurine (compound 23)

3-[5-(4-Amidino-2-fluorophenoxycarbonyl)thiophen-2-yl]-2,2-dimethylpropanoic acid trifluoroacetic acid salt (200 mg, 0.40 mmol) obtained in Example 3, step 5 was dissolved in thionyl chloride (4 mL), and the mixture was stirred at room temperature for 30 minutes. Thionyl chloride was evaporated under reduced pressure to give the acid chloride. The obtained acid chloride was dissolved in 1,2-dichloroethane (10 mL), N-allyltaurine isopropyl ester obtained in step 1 (88 mg, 0.43 mmol) and pyridine (0.4 mL) were added thereto, and the mixture was stirred at 50° C. overnight. The mixture was concentrated under reduced pressure. The obtained residue was purified by high performance liquid chromatography (water-acetonitrile, each containing 0.1% trifluoroacetic acid) to give the isopropyl ester of the title compound. The obtained solid was dissolved in 0.01 N aqueous hydrochloric acid (20 mL) solution and stirred at room temperature for 5 hours, and the precipitated solid was collected by filtration. The solid was washed with water and dried to give the title compound (47 mg, 0.092 mmol, 23%).

1H-NMR (400 MHz, DMSO-d6) δ 9.41 (2H, br s), 9.02 (2H, br s), 7.95-7.88 (2H, m), 7.81-7.70 (2H, m), 7.10 (1H, d, J=3.6 Hz), 5.76 (1H, m), 5.20-5.05 (2H, m), 4.15-3.85 (2H, m), 3.70-3.45 (2H, m), 3.21 (2H, s), 2.67 (2H, m), 1.26 (6H, s).

MS(ESI) m/z 512 (M+H)+

Example 9

Synthesis of N-{3-[5-(4-amidino-2-fluorophenoxycarbonyl)thiophen-2-yl]-2,2-diethylpropionyl}-beta-homoisoleucine hydrochloride (compound 49)

The compound 18 (76 mg, 0.15 mmol) was dissolved in thionyl chloride (1.5 mL), and the mixture was stirred at room temperature for 30 minutes. Thionyl chloride was evaporated under reduced pressure to give the acid chloride. The obtained acid chloride was dissolved in dichloromethane (1.5 mL), beta-homoisoleucine methyl ester hydrochloride (44 mg, 0.225 mmol) and pyridine (0.2 mL) were added thereto, and the mixture was stirred at room temperature overnight. After evaporation of the solvent, trifluoroacetic acid (5 mL) was added and the mixture was stirred at 60° C. for 1 hour. The mixture was concentrated under reduced pressure. After evaporation of the solvent, 4 N-hydrogen chloride in 1,4-dioxane (2 mL) and water (1 mL) were added, and the mixture was stirred at 80° C. 30 minutes. The mixture was concentrated under reduced pressure. The obtained residue was purified by high performance liquid chromatography (water-acetonitrile, each containing 0.1% trifluoroacetic acid) to give the trifluoroacetic acid salt of the title compound.

To the obtained trifluoroacetic acid salt was added 0.1 N-hydrochloric acid solution (10 mL), and the mixture was lyophilized to give the title compound (35.6 mg, 0.064 mmol, 43%).

1H NMR (400 MHz, DMSO-d6) δ 12.09 (1H, s), 9.44 (2H, s), 9.17 (2H, s), 7.98-7.91 (2H, m), 7.78-7.72 (2H, m), 7.37 (1H, d, J=8.2 Hz), 7.06 (1H, d, J=3.8 Hz), 4.19-4.09 (1H, m), 3.17-3.06 (2H, m), 2.43-2.30 (2H, m), 1.63-1.44 (4H, m), 1.40-1.27 (1H, m), 1.11-0.98 (1H, m), 0.89-0.73 (10H, m).

MS(ESI) m/z 520 (M+H)+

The compounds 39, 40, 45, 46, 51, 55, 63, 64, 65, 68, 81, and 89 shown in the following Table 1 were each synthesized using the compound 16 or the compound obtained in Example 3, step 5 and commercially available reagents and by an operation in the same manner as in the above-mentioned Example 4, step 2.

The compounds 3, 4, 6, 12, 13, 14, 15, 16, 19, 24, 25, 27, 28, 29, 30, 31, 34, 42, 43, 44, 52, 58, 83, and 87 shown in the following Table 1 were each synthesized using the compound 16 or the compound obtained in Example 3, step 5 and commercially available reagents and by an operation in the same manner as in the above-mentioned Example 6.

The compounds 7, 8, 17, 20, 22, 26, 32, 33, 41, 48, 56, 57, 62, 66, 67, 69, 70, 71, 73, 75, 76, 77, 78, 79, 80, 84, 85, 86, 88, 90, 91, 92, and 93 shown in the following Table 1 were each synthesized using the compound 16 or the compound obtained in Example 3, step 5 and commercially available reagents and by an operation in the same manner as in the above-mentioned Example 7.

The compounds 5, 35, 36, 37, 38, 47, 50, 53, 54, 59, 60, 61, 72, 74, 82, and 94 shown in the following Table 1 were each synthesized using the compound 16 or the compound obtained in Example 3, step 5 and commercially available reagents and by an operation in the same manner as in the above-mentioned Example 9.

TABLE 1

| Compound No. | Structure | Analysis data |
|---|---|---|
| 1 | 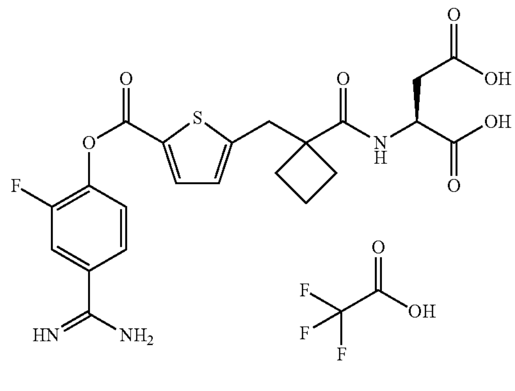 [SMILES: N=C(N)c1ccc(OC(=O)c2ccc(CC3(C(=O)N[C@@H](CC(=O)O)C(=O)O)CCC3)s2)c(F)c1 ; O=C(O)C(F)(F)F] | 1H-NMR (400 MHz, DMSO-d6) δ 9.42 (2H, br s), 9.09 (2H, br s), 8.07 (1H, d, J = 8.0 Hz), 7.99-7.83 (2H, m), 7.92-7.82 (1H, m), 7.79-7.69 (2H, m), 7.06 (1H, d, J = 3.9 Hz), 4.56 (1H, dd, J = 13.9, 7.6 Hz), 3.48 (2H, s), 2.74 (1H, dd, J = 16.4, 6.0 Hz), 2.64-2.49 (1H, m), 2.40-2.25 (2H, m), 2.05-1.83 (3H, m), 1.80-1.69 (1H, m). MS (ESI) m/z 492 (M + H)+ |
| 2 | 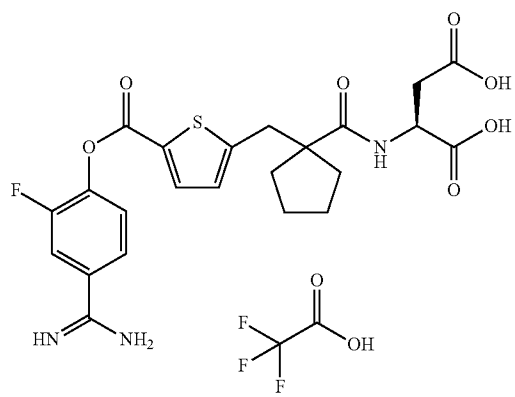 [SMILES: N=C(N)c1ccc(OC(=O)c2ccc(CC3(C(=O)N[C@@H](CC(=O)O)C(=O)O)CCCC3)s2)c(F)c1 ; O=C(O)C(F)(F)F] | 1H-NMR (400 MHz, DMSO-d6) δ 9.36 (2H, br s), 9.08 (2H, br s), 7.97 (1H, d, J = 7.9 Hz), 7.89-7.80 (2H, m), 7.72-7.63 (2H, m), 7.00 (1H, d, J = 3.9 Hz), 4.49 (2H, dt, J = 12.9, 6.4 Hz), 3.17 (2H, s), 2.69 (1H, dd, J = 16.4, 6.0 Hz), 2.57-2.45 (2H, m), 2.02-1.81 (2H, m), 1.63-1.37 (6H, m). MS (ESI) m/z 506 (M + H)+ |
| 3 | 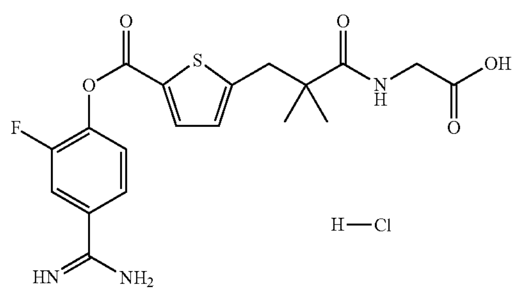 [SMILES: CC(C)(Cc1ccc(C(=O)Oc2ccc(C(=N)N)cc2F)s1)C(=O)NCC(=O)O ; Cl] | 1H NMR (400 MHz, DMSO-d6) δ 9.42 (2H, br s), 9.17 (2H, br s), 8.12-7.98 (1H, m), 7.98-7.87 (2H, m), 7.83-7.68 (2H, m), 7.08 (1H, d, J = 3.9 Hz), 3.73 (2H, d, J = 5.8 Hz), 3.12 (2H, s), 1.13 (6H, s) MS (ESI) m/z 422 (M + H)+ |
| 4 | 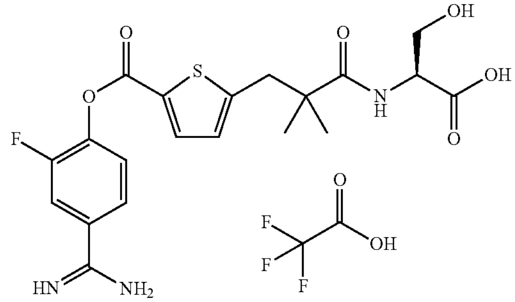 | 1H NMR (400 MHz, DMSO-d6) δ 9.41 (2H, br s), 9.07 (2H, br s), 7.98-7.87 (2H, m), 7.82-7.69 (2H, m), 7.56 (1H, d, J = 7.8 Hz), 7.09 (1H, d, J =3.9 Hz), 4.30 (1H, dt, J = 7.9, 5.0 Hz), 3.70 (2H, ddd, J = 15.2, 11.1, 4.9 Hz), 3.16 (2H, s), 1.17 (6H, s) MS (ESI) m/z 452 (M + H)+ |

TABLE 1-continued

| Compound No. | Structure | Analysis data |
|---|---|---|
| 5 | 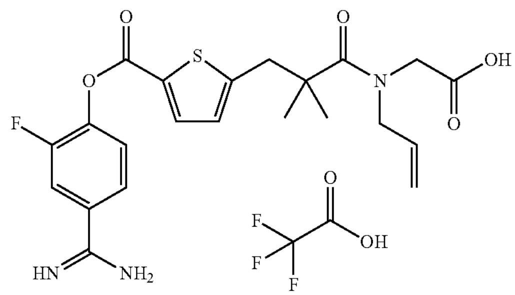 [SMILES: C=CCN(CC(=O)O)C(=O)C(C)(C)Cc1ccc(C(=O)Oc2ccc(C(=N)N)cc2F)s1 ; O=C(O)C(F)(F)F] | MS (ESI) m/z 462 (M + H)+ |
| 6 | 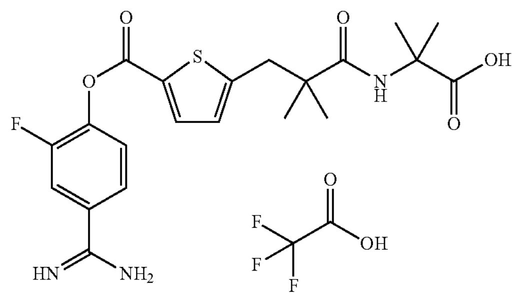 [SMILES: CC(C)(Cc1ccc(C(=O)Oc2ccc(C(=N)N)cc2F)s1)C(=O)NC(C)(C)C(=O)O ; O=C(O)C(F)(F)F] | 1H NMR (400 MHz, DMSO-d6) δ 9.41 (2H, br s), 9.12 (2H, br s), 8.00-7.87 (2H, m), 7.81-7.68 (2H, m), 7.54 (1H, s), 7.08 (1H, d, J = 3.8 Hz), 3.13 (2H, s), 1.36 (6H, s), 1.14 (6H, s) MS (ESI) m/z 450 (M + H)+ |
| 7 | 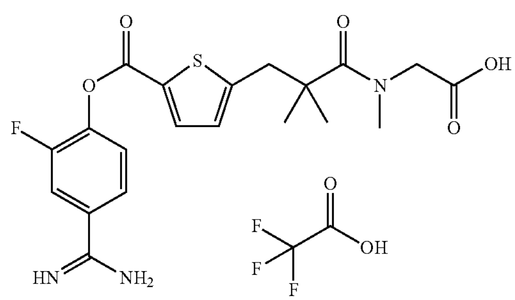 [SMILES: CN(CC(=O)O)C(=O)C(C)(C)Cc1ccc(C(=O)Oc2ccc(C(=N)N)cc2F)s1 ; O=C(O)C(F)(F)F] | ¹H NMR (400 MHz, DMSO-d6) δ 9.41 (2H, br s), 9.18 (2H, br s), 7.98-7.88 (2H, m), 7.81-7.70 (2H, m), 7.12 (1H, d, J = 3.8 Hz), 3.99 (3H, s), 3.21 (2H, s), 1.26 (6H, s) MS (ESI) m/z 436 (M + H)+ |
| 8 | 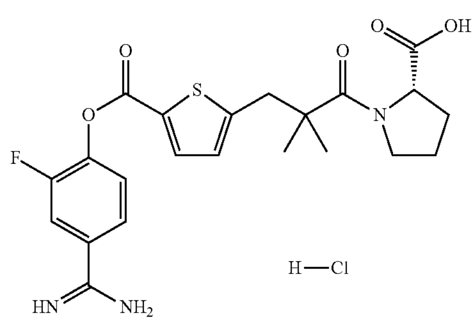 [SMILES: CC(C)(Cc1ccc(C(=O)Oc2ccc(C(=N)N)cc2F)s1)C(=O)N1CCC[C@H]1C(=O)O ; Cl] | MS (ESI) m/z 462 (M + H)+ |
| 9 | 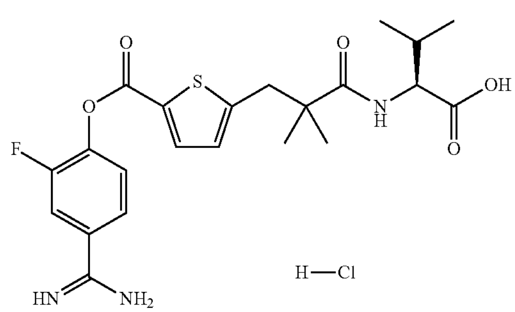 [SMILES: CC(C)[C@H](NC(=O)C(C)(C)Cc1ccc(C(=O)Oc2ccc(C(=N)N)cc2F)s1)C(=O)O ; Cl] | 1H-NMR (400 MHz, DMSO-d6) δ 9.41 (2H, br s), 9.10 (2H, br s), 8.00-7.89 (2H, m), 7.80-7.70 (2H, m), 7.57 (1H, d, J = 7.2 Hz), 7.08 (1H, s), 4.13 (1H, m), 3.21 (1H, d, J = 16.0 Hz), 3.15 (1H, d, J = 16.0 Hz), 2.15-2.05 (1H, m), 1.76-1.50 (4H, m), 0.90 (3H, d, J = 6.8 Hz), 0.86-0.75 (6H, m). MS (ESI) m/z 464 (M + H)+ |

TABLE 1-continued

| Compound No. | Structure | Analysis data |
|---|---|---|
| 10 | 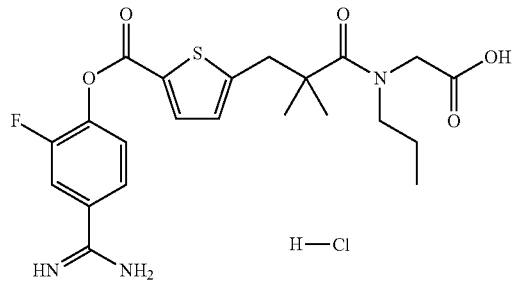 [SMILES: CCCN(CC(=O)O)C(=O)C(C)(C)Cc1ccc(C(=O)Oc2ccc(C(=N)N)cc2F)s1 ; Cl] | 1H-NMR (400 MHz, DMSO-d6) δ 9.41 (2H, br s), 9.05 (2H, br s), 7.93 (2H, m), 7.74 (2H, m), 7.11 (1H, d, J = 3.6 Hz), 3.75-3.65 (2H, m), 3.18 (2H, s), 1.58-1.48 (2H, m), 1.25 (6H, br s), 0.84 (3H, m).<br>MS (ESI) m/z 464 (M + H)+ |
| 11 | 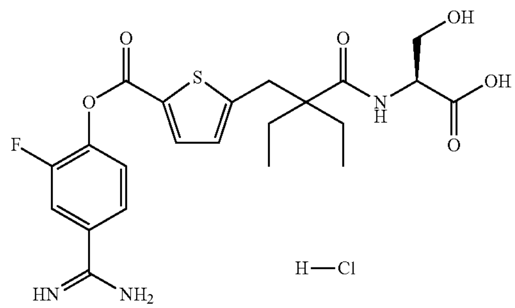 [SMILES: CCC(CC)(Cc1ccc(C(=O)Oc2ccc(C(=N)N)cc2F)s1)C(=O)N[C@@H](CO)C(=O)O ; Cl] | 1H-NMR (400 MHz, DMSO-d6) δ 9.41 (2H, br s), 9.10 (2H, br s), 7.95-7.90 (2H, m), 7.78-7.72 (2H, m), 7.63 (1H, d, J = 7.6 Hz), 7.10 (1H, d, J = 4.0 Hz), 4.34 (1H, m), 3.75-3.64 (1H, m), 3.64-3.56 (1H, m), 3.16 (2H, s), 1.62-1.46 (4H, m), 0.88-0.78 (6H, m).<br>MS (ESI) m/z 480 (M + H)+ |
| 12 | 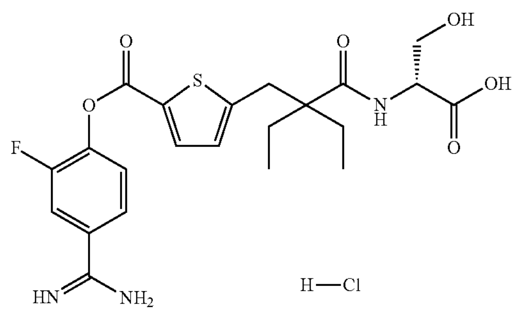 [SMILES: CCC(CC)(Cc1ccc(C(=O)Oc2ccc(C(=N)N)cc2F)s1)C(=O)N[C@H](CO)C(=O)O ; Cl] | 1H-NMR (400 MHz, DMSO-d6) δ 9.37 (4H, br s), 7.95-7.88 (2H, m), 7.78-7.72 (2H, m), 7.56 (1H, d, J = 6.8 Hz), 7.10 (1H, d, J = 3.6 Hz), 4.23 (1H, m), 3.72-3.68 (1H, m), 3.65-3.58 (1H, m), 3.16 (2H, s), 1.62-1.49 (4H, m), 0.88-0.80 (6H, m).<br>MS (ESI) m/z 480 (M + H)+ |
| 13 | 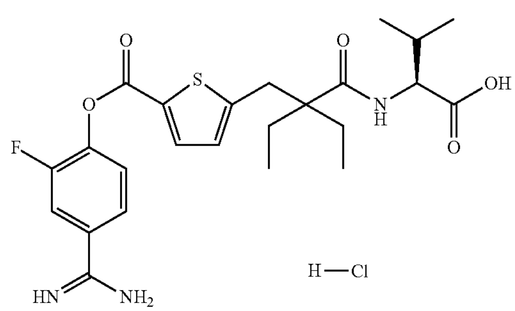 [SMILES: CCC(CC)(Cc1ccc(C(=O)Oc2ccc(C(=N)N)cc2F)s1)C(=O)N[C@H](C(=O)O)C(C)C ; Cl] | 1H-NMR (400 MHz, DMSO-d6) δ 9.41 (2H, br s), 9.10 (2H, br s), 7.95-7.88 (2H, m), 7.80-7.70 (2H, m), 7.57 (1H, d, J = 7.2 Hz), 7.08 (1H, d, J = 3.6 Hz), 4.13 (1H, m), 3.23-3.10 (2H, m), 2.08 (1H, m), 1.65-1.45 (4H, m), 0.90 (6H, d, J = 6.8 Hz), 0.88-0.80 (6H, m).<br>MS (ESI) m/z 492 (M + H)+ |
| 14 | 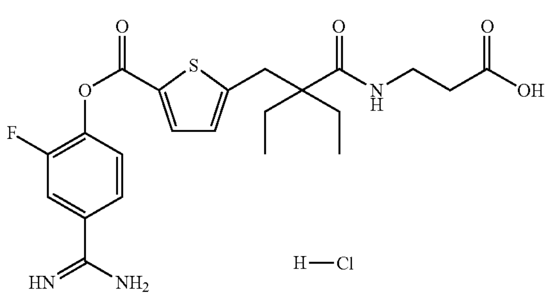 [SMILES: CCC(CC)(Cc1ccc(C(=O)Oc2ccc(C(=N)N)cc2F)s1)C(=O)NCCC(=O)O ; Cl] | 1H-NMR (400 MHz, DMSO-d6) δ 9.39 (2H, br s), 9.10 (2H, br s), 7.90-7.85 (2H, m), 7.75-7.65 (3H, m), 6.97 (1H, d, J = 2.4 Hz), 3.30 (2H, m), 3.05 (2H, s), 2.35 (2H, t, J = 6.4 Hz), 1.50-1.30 (4H, m), 0.75-0.65 (6H, t, J = 7.2 Hz).<br>MS (ESI) m/z 464 (M + H)+ |

TABLE 1-continued

| Compound No. | Structure | Analysis data |
|---|---|---|
| 15 | 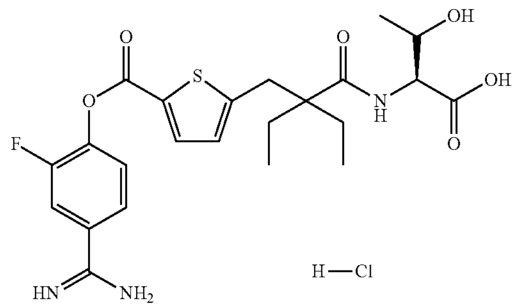 [SMILES: CCC(CC)(Cc1ccc(C(=O)Oc2ccc(C(=N)N)cc2F)s1)C(=O)N[C@H](C(=O)O)C(C)O ; Cl] | 1H-NMR (400 MHz, DMSO-d6) δ 9.41 (2H, br s), 9.18 (2H, br s), 7.95-7.90 (2H, m), 7.78-7.72 (2H, m), 7.18 (1H, d, J = 8.0 Hz), 7.10 (1H, d, J = 4.0 Hz), 4.22 (1H, m), 4.12 (1H, m), 3.16 (2H, s), 1.62-1.49 (4H, m), 1.03 (3H, d, J = 6.4 Hz), 0.88-0.80 (6H, t, J = 7.2 Hz).<br>MS (ESI) m/z 494 (M + H)+ |
| 16 | 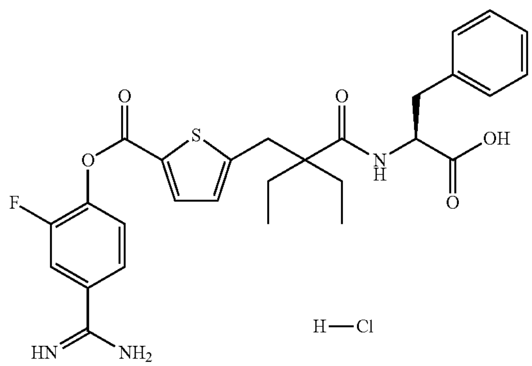 [SMILES: CCC(CC)(Cc1ccc(C(=O)Oc2ccc(C(=N)N)cc2F)s1)C(=O)N[C@@H](Cc1ccccc1)C(=O)O ; Cl] | 1H-NMR (400 MHz, DMSO-d6) δ 9.44 (4H, br s), 7.95 (1H, d, J = 11.2 Hz), 7.88-7.80 (2H, m), 7.78-7.70 (2H, m), 7.30-7.20 (4H, m), 7.20-7.12 (1H, m), 6.88 (1H, d, J = 4.0 Hz), 4.54 (1H, m), 3.18-2.92 (4H, m), 1.55-1.30 (4H, m), 0.72 (3H, t, J = 7.2 Hz), 0.53 (3H, t, J = 7.2 Hz).<br>MS (ESI) m/z 540 (M + H)+ |
| 17 | 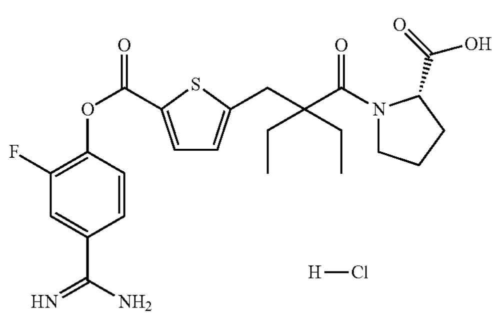 [SMILES: CCC(CC)(Cc1ccc(C(=O)Oc2ccc(C(=N)N)cc2F)s1)C(=O)N1CCC[C@H]1C(=O)O ; Cl] | 1H-NMR (400 MHz, DMSO-d6) δ 9.43 (2H, br s), 9.16 (2H, br s), 7.98-7.92 (2H, m), 7.80-7.70 (2H, m), 7.11 (1H, d, J = 4.0 Hz), 4.39 (1H, m), 3.78-3.60 (2H, m), 3.24 (1H, d, J = 15.2 Hz), 3.16 (1H, d, J = 15.2 Hz), 2.10 (1H, m), 2.00-1.85 (2H, m), 1.80-1.45 (5H, m), 0.88 (3H, t, J = 7.2 Hz), 0.78 (3H, t, J = 7.2 Hz).<br>MS (ESI) m/z 490 (M + H)+ |
| 18 | 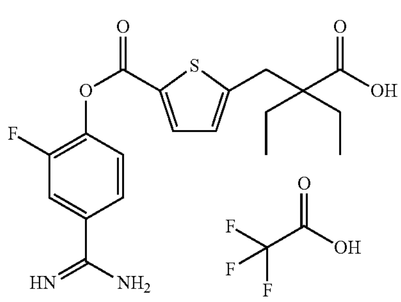 | 1H-NMR (400 MHz, DMSO-d6) δ 9.42 (2H, br s), 9.24 (2H, br s), 7.97 (1H, d, J = 4.0 Hz), 7.94 (1H, d, J = 10.4 Hz), 7.80-7.70 (2H, m), 7.10 (1H, d, J = 4.0 Hz), 3.15 (2H, s), 1.60-1.40 (4H, m), 0.85 (6H, t, J = 7.6 Hz).<br>MS (ESI) m/z 393 (M + H)+ |

TABLE 1-continued

| Compound No. | Structure | Analysis data |
|---|---|---|
| 19 | 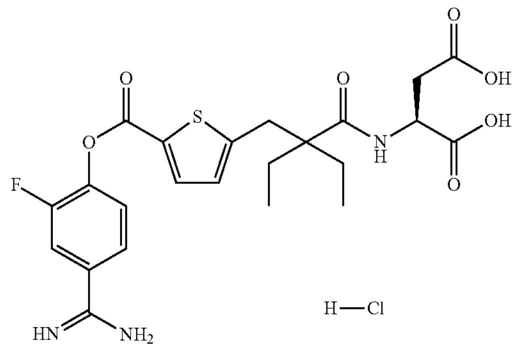 [SMILES: CCC(CC)(Cc1ccc(C(=O)Oc2ccc(C(=N)N)cc2F)s1)C(=O)N[C@@H](CC(=O)O)C(=O)O ; Cl] | 1H-NMR (400 MHz, DMSO-d6) δ 9.39 (2H, br s), 9.12 (2H, br s), 7.90-7.85 (3H, m), 7.70-7.65 (2H, m), 7.02 (1H, d, J = 4.0 Hz), 4.50 (1H, m), 3.06 (2H, s), 2.70 (1H, dd, J = 16.4, 6.0 Hz), 2.51 (1H, dd, J = 16.4, 7.2 Hz), 1.50-1.38 (4H, m), 0.80-0.70 (6H, m).<br>MS (ESI) m/z 508 (M + H)+ |
| 20 | 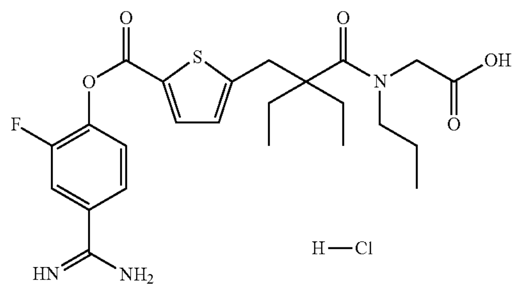 [SMILES: CCCN(CC(=O)O)C(=O)C(CC)(CC)Cc1ccc(C(=O)Oc2ccc(C(=N)N)cc2F)s1 ; Cl] | 1H-NMR (400 MHz, DMSO-d6) δ 9.46 (4H, br s), 8.00-7.92 (2H, m), 7.80-7.70 (2H, m), 7.13 (1H, d, J = 3.6 Hz), 3.89 (2H, m), 3.40 (2H, m), 3.21 (2H, s), 1.80-1.40 (6H, m), 0.90-0.70 (9H, m).<br>MS (ESI) m/z 492 (M + H)+ |
| 21 | 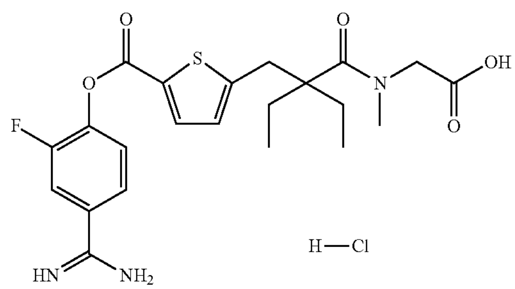 [SMILES: CCC(CC)(Cc1ccc(C(=O)Oc2ccc(C(=N)N)cc2F)s1)C(=O)N(C)CC(=O)O ; Cl] | 1H-NMR (400 MHz, DMSO-d6) δ 9.35 (2H, br s), 9.22 (2H, br s), 7.90-7.85 (2H, m), 7.70-7.65 (2H, m), 7.06 (1H, d, J = 3.6 Hz), 3.92 (2H, m), 3.15 (3H, s), 3.12 (2H, br s), 1.70-1.60 (2H, m), 1.60-1.50 (2H, m), 0.76 (6H, t, J = 7.2 Hz).<br>MS (ESI) m/z 464 (M + H)+ |
| 22 | 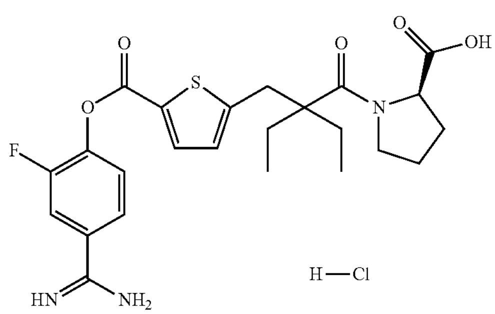 [SMILES: CCC(CC)(Cc1ccc(C(=O)Oc2ccc(C(=N)N)cc2F)s1)C(=O)N1CCC[C@@H]1C(=O)O ; Cl] | 1H-NMR (400 MHz, DMSO-d6) δ 9.46 (2H, br s), 9.21 (2H, br s), 7.98-7.94 (2H, m), 7.78-7.74 (2H, m), 7.11 (1H, d, J = 3.6 Hz), 4.39 (1H, m), 3.78-3.60 (2H, m), 3.24 (1H, d, J = 15.2 Hz), 3.16 (1H, d, J = 15.2 Hz), 2.10 (1H, m), 2.00-1.85 (2H, m), 1.80-1.45 (5H, m), 0.88 (3H, t, J = 7.2 Hz), 0.78 (3H, t, J = 7.2 Hz).<br>MS (ESI) m/z 490 (M + H)+ |
| 23 | 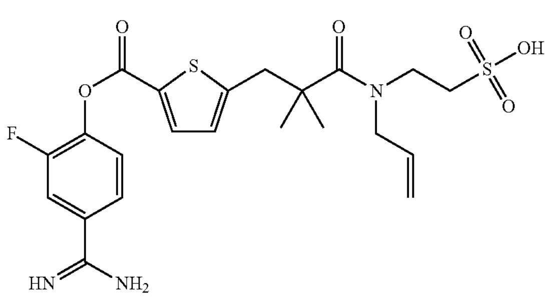 [SMILES: C=CCN(CCS(=O)(=O)O)C(=O)C(C)(C)Cc1ccc(C(=O)Oc2ccc(C(=N)N)cc2F)s1] | 1H-NMR (400 MHz, DMSO-d6) δ 9.41 (2H, br s), 9.02 (2H, br s), 7.95-7.88 (2H, m), 7.81-7.70 (2H, m), 7.10 (1H, d, J = 3.6 Hz), 5.76 (1H, m), 5.20-5.05 (2H, m), 4.15-3.85 (2H, m), 3.70-3.45 (2H, m), 3.21 (2H, s), 2.67 (2H, m), 1.26 (6H, s).<br>MS (ESI) m/z 512 (M + H)+ |

| Compound No. | Structure | Analysis data |
|---|---|---|
| 24 | 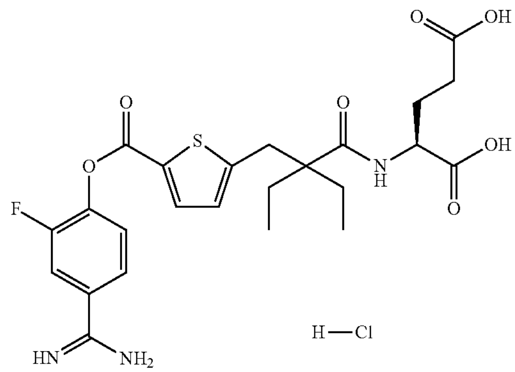 [SMILES: CCC(CC)(Cc1ccc(C(=O)Oc2ccc(C(=N)N)cc2F)s1)C(=O)N[C@@H](CCC(=O)O)C(=O)O ; Cl] | 1H-NMR (400 MHz, DMSO-d6) δ 9.46 (2H, br s), 9.25 (2H, br s), 7.97-7.92 (2H, m), 7.85 (1H, d, J = 7.2 Hz), 7.76-7.74 (2H, m), 7.08 (1H, d, J = 3.6 Hz), 4.25 (1H, m), 3.15 (2H, s), 2.26 (2H, t, J = 8.0 Hz), 2.06-1.95 (1H, m), 1.92-1.80 (1H, m), 1.60-1.46 (4H, m), 0.86-0.79 (6H, m).<br>MS (ESI) m/z 528 (M + H)+ |
| 25 | 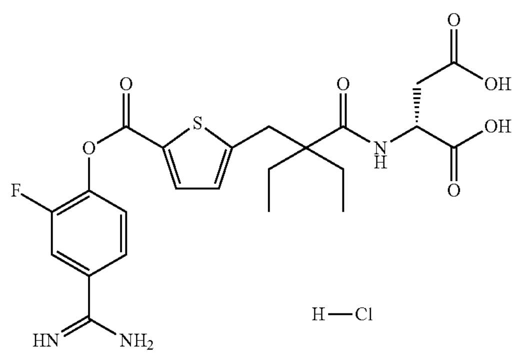 [SMILES: CCC(CC)(Cc1ccc(C(=O)Oc2ccc(C(=N)N)cc2F)s1)C(=O)N[C@H](CC(=O)O)C(=O)O ; Cl] | 1H-NMR (400 MHz, DMSO-d6) δ 9.45 (2H, br s), 9.16 (2H, br s), 7.97-7.92 (3H, m), 7.78-7.72 (2H, m), 7.09 (1H, d, J = 3.6 Hz), 4.57 (1H, m), 3.13 (2H, s), 2.76 (1H, dd, J = 16.4, 5.2 Hz), 2.58 (1H, dd, J = 16.4, 6.4 Hz), 1.56-1.44 (4H, m), 0.86-0.78 (6H, m).<br>MS (ESI) m/z 508 (M + H)+ |
| 26 | 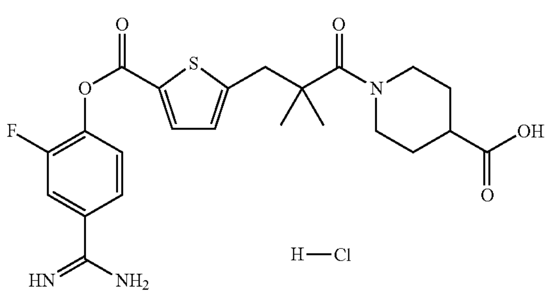 [SMILES: CC(C)(Cc1ccc(C(=O)Oc2ccc(C(=N)N)cc2F)s1)C(=O)N1CCC(C(=O)O)CC1 ; Cl] | 1H NMR (400 MHz, DMSO-d6) δ 9.45 (2H, br s), 9.18 (2H, br s), 7.99-7.88 (2H, m), 7.80-7.71 (2H, m), 7.09 (1H, d, J = 3.8 Hz), 4.20 (2H, d, J = 13.7 Hz), 3.22 (2H, s), 3.06-2.91 (2H, m), 2.61-2.51 (1H, m), 1.93-1.77 (2H, m), 1.50-1.35 (2H, m), 1.24 (6H, s)<br>MS (ESI) m/z 476 (M + H)+ |
| 27 | 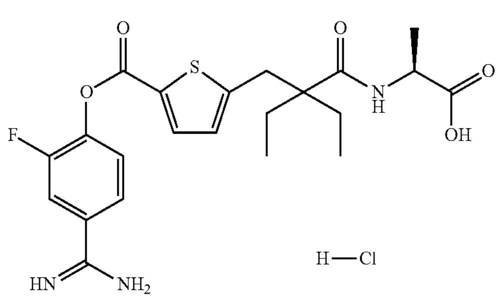 [SMILES: CCC(CC)(Cc1ccc(C(=O)Oc2ccc(C(=N)N)cc2F)s1)C(=O)N[C@@H](C)C(=O)O ; Cl] | MS (ESI) m/z 464 (M + H)+ |

TABLE 1-continued

| Compound No. | Structure | Analysis data |
|---|---|---|
| 28 | (structure) | MS (ESI) m/z 478 (M + H)+ |
| 29 | (structure) | MS (ESI) m/z 492 (M + H)+ |
| 30 | (structure) | 1H NMR (400 MHz, DMSO-d6) δ 12.05 (1H, s), 9.69-9.03 (4H, m), 7.94 (2H, t, J = 7.6 Hz), 7.80-7.71 (3H, m), 7.04 (1H, d, J = 3.9 Hz), 3.16-3.08 (4H, m), 2.20 (2H, t, J = 7.4 Hz), 1.66 (2H, p, J = 7.2 Hz), 1.60-1.40 (4H, m), 0.80 (6H, t, J = 7.4 Hz)<br>MS (ESI) m/z 478 (M + H)+ |
| 31 | (structure) | 1H NMR (400 MHz, DMSO-d6) δ 9.71 (1H, s), 9.39 (2H, br s), 9.06 (2H, br s), 7.99-7.84 (4H, m), 7.84-7.76 (2H, m), 7.76-7.67 (2H, m), 7.07 (1H, d, J = 3.8 Hz), 3.34 (2H, s), 1.30 (6H, s)<br>MS (ESI) m/z 484 (M + H)+ |

TABLE 1-continued
| Compound No. | Structure | Analysis data |
|---|---|---|
| 32 | 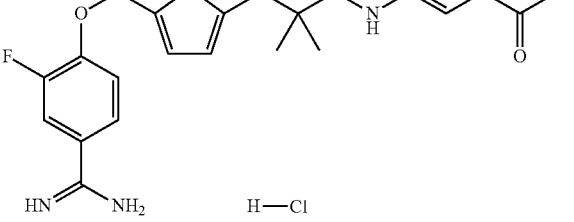 | 1H NMR (400 MHz, DMSO-d6) δ 9.64 (1H, s), 9.40 (2H, br s), 9.07 (2H, br s), 8.25 (1H, s), 7.99-7.87 (3H, m), 7.79-7.69 (2H, m), 7.65 (1H, d, J = 7.9 Hz), 7.44 (1H, dd, J = 7.9 Hz), 7.08 (1H, d, J = 3.5 Hz), 3.34 (2H, s), 1.29 (6H, s)<br>MS (ESI) m/z 484 (M + H)+ |
| 33 | 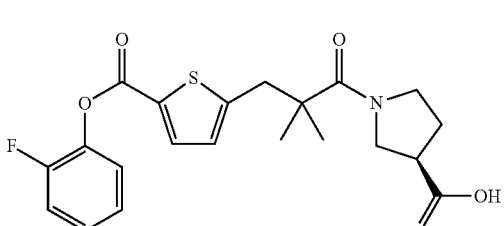 | 1H NMR (400 MHz, DMSO-d6) δ 12.54 (1H, s), 9.47 (2H, s), 9.21 (2H, s), 7.95 (1H, d, J = 11.5 Hz), 7.92 (1H, d, J = 3.8 Hz), 7.81-7.69 (2H, m), 7.08 (1H, d, J = 3.8 Hz), 3.89-3.33 (4H, m), 3.24-2.91 (3H, m), 2.22-1.87 (2H, m), 1.22 (6H, s)<br>MS (ESI) m/z 462 (M + H)+ |
| 34 | 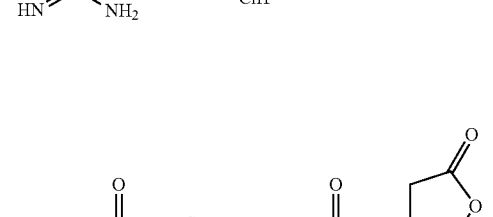 | 1H NMR (400 MHz, DMSO-d6) δ 9.46 (2H, s), 9.18 (2H, s), 8.20 (1H, d, J = 6.0 Hz), 8.00-7.91 (2H, m), 7.78-7.71 (2H, m), 7.06 (1H, d, J = 3.9 Hz), 4.58-4.43 (2H, m), 4.07 (1H, dd, J = 9.1, 3.0 Hz), 3.15 (2H, s), 2.87 (1H, dd, J = 17.7, 8.4 Hz), 2.45 (1H, dd, J = 17.7, 3.6 Hz), 1.64-1.42 (4H, m), 0.86-0.76 (6H, m)<br>MS (ESI) m/z 476 (M + H)+ |
| 35 | 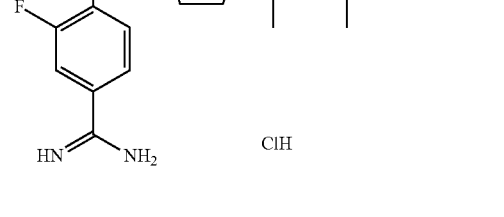 | MS (ESI) m/z 504 (M + H)+ |

TABLE 1-continued

| Compound No. | Structure | Analysis data |
| --- | --- | --- |
| 36 | 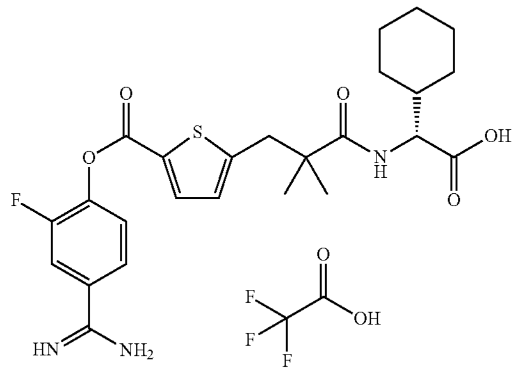 [SMILES: CC(C)(Cc1ccc(C(=O)Oc2ccc(C(=N)N)cc2F)s1)C(=O)N[C@@H](C(=O)O)C1CCCCC1 ; O=C(O)C(F)(F)F] | MS (ESI) m/z 504 (M + H)+ |
| 37 | 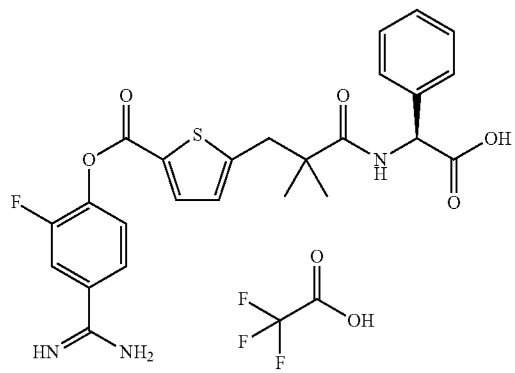 [SMILES: CC(C)(Cc1ccc(C(=O)Oc2ccc(C(=N)N)cc2F)s1)C(=O)N[C@H](C(=O)O)c1ccccc1 ; O=C(O)C(F)(F)F] | MS (ESI) m/z 498 (M + H)+ |
| 38 | 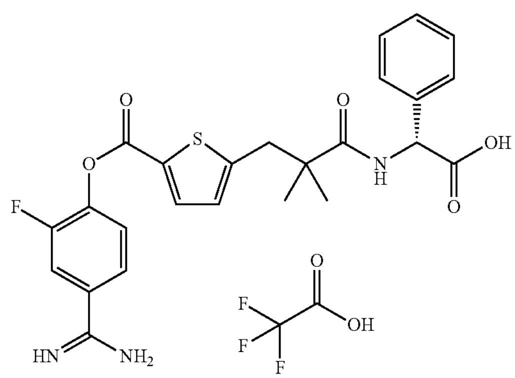 [SMILES: CC(C)(Cc1ccc(C(=O)Oc2ccc(C(=N)N)cc2F)s1)C(=O)N[C@@H](C(=O)O)c1ccccc1 ; O=C(O)C(F)(F)F] | MS (ESI) m/z 498 (M + H)+ |
| 39 | 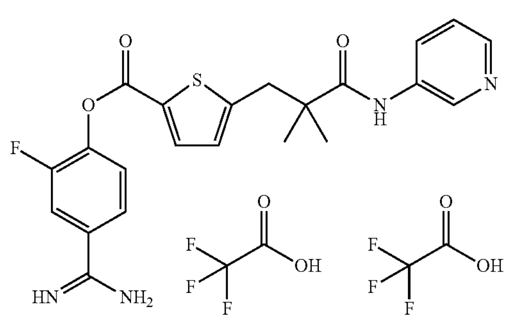 [SMILES: CC(C)(Cc1ccc(C(=O)Oc2ccc(C(=N)N)cc2F)s1)C(=O)Nc1cccnc1 ; O=C(O)C(F)(F)F ; O=C(O)C(F)(F)F] | MS (ESI) m/z 441 (M + H)+ |

TABLE 1-continued
| Compound No. | Structure | Analysis data |
|---|---|---|
| 40 | 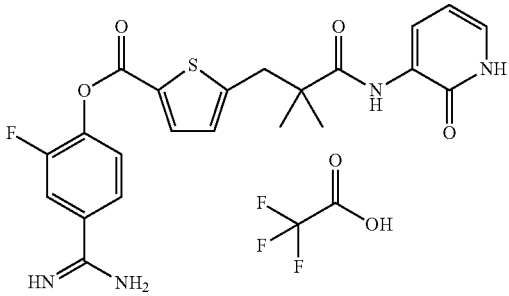 | MS (ESI) m/z 457 (M + H)+ |
| 41 | 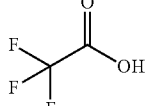 | 1H NMR (400 MHz, DMSO-d6) δ 12.17 (1H, br s), 9.67-9.09 (4H, m), 8.00-7.89 (2H, m), 7.81-7.70 (2H, m), 7.08 (1H, d, J = 3.8 Hz), 4.33-4.21 (1H, m), 3.68-3.50 (2H, m), 3.27-3.09 (2H, m), 2.83-2.71 (1H, m), 2.26-2.12 (1H, m), 2.00-1.76 (3H, m), 1.67-1.54 (1H, m), 1.22 (6H, d, J = 7.2 Hz)<br>MS (ESI) m/z 476 (M + H)+ |
| 42 | 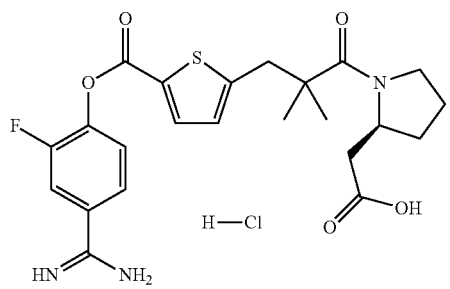 | 1H NMR (400 MHz, DMSO-d6) δ 12.17 (1H, br s), 9.67-9.09 (4H, m), 8.00-7.89 (2H, m), 7.81-7.70 (2H, m), 7.08 (1H, d, J = 3.8 Hz), 4.33-4.21 (1H, m), 3.68-3.50 (2H, m), 3.27-3.09 (2H, m), 2.83-2.71 (1H, m), 2.26-2.12 (1H, m), 2.00-1.76 (3H, m), 1.67-1.54 (1H, m), 1.22 (6H, d, J = 7.2 Hz)<br>MS (ESI) m/z 521 (M + H)+ |
| 43 | 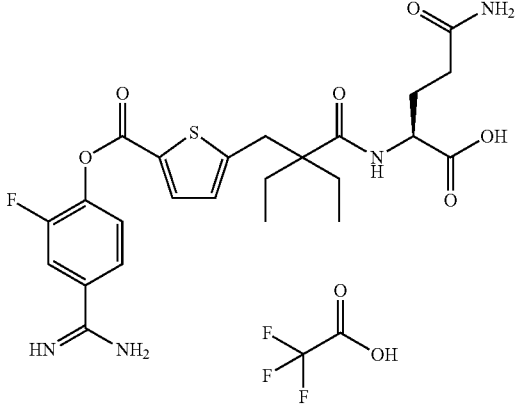 [SMILES: CCC(CC)(Cc1ccc(C(=O)Oc2ccc(C(=N)N)cc2F)s1)C(=O)N[C@@H](CCC(N)=O)C(=O)O ; O=C(O)C(F)(F)F] | 1H NMR (400 MHz, DMSO-d6) δ 12.36 (2H, br s), 9.46 (2H, s), 9.23 (2H, s), 7.98-7.91 (2H, m), 7.85 (1H, d, J = 7.5 Hz), 7.79-7.72 (2H, m), 7.08 (1H, d, J = 3.9 Hz), 4.29-4.20 (1H, m), 3.15 (2H, s), 2.27 (2H, t, J = 7.6 Hz), 2.09-1.80 (2H, m), 1.60-1.47 (4H, m), 0.89-0.78 (6H, m)<br>MS (ESI) m/z 522 (M + H)+ |

TABLE 1-continued

| Compound No. | Structure | Analysis data |
|---|---|---|
| 44 | 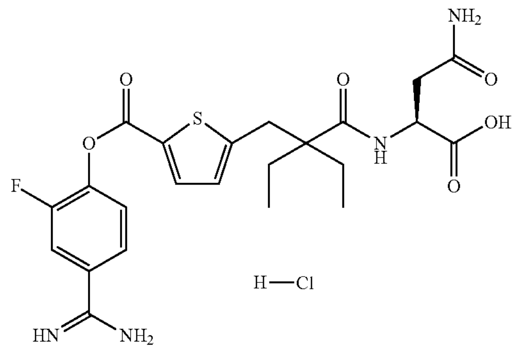 [SMILES: CCC(CC)(Cc1ccc(C(=O)Oc2ccc(C(=N)N)cc2F)s1)C(=O)N[C@@H](CC(N)=O)C(=O)O ; Cl] | 1H NMR (400 MHz, DMSO-d6) δ 12.54 (1H, s), 9.47 (2H, s), 9.21 (2H, s), 7.98-7.89 (3H, m), 7.80-7.73 (2H, m), 7.38 (1H, s), 7.09 (1H, d, J = 3.9 Hz), 6.92 (1H, s), 4.59 (1H, dd, J = 13.2, 7.4 Hz), 3.13 (2H, s), 2.64-2.52 (2H, m), 1.57-1.44 (4H, m), 0.89-0.75 (6H, m)<br>MS (ESI) m/z 507 (M + H)+ |
| 45 | 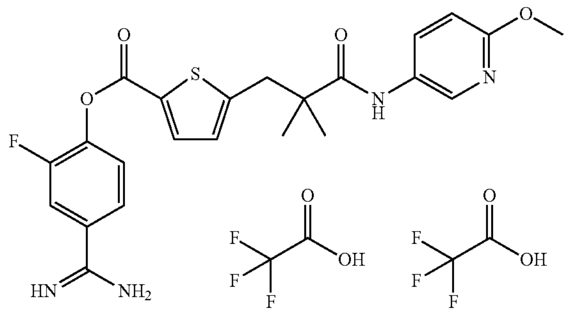 [SMILES: COc1ccc(NC(=O)C(C)(C)Cc2ccc(C(=O)Oc3ccc(C(=N)N)cc3F)s2)cn1 ; O=C(O)C(F)(F)F ; O=C(O)C(F)(F)F] | MS (ESI) m/z 471 (M + H)+ |
| 46 | 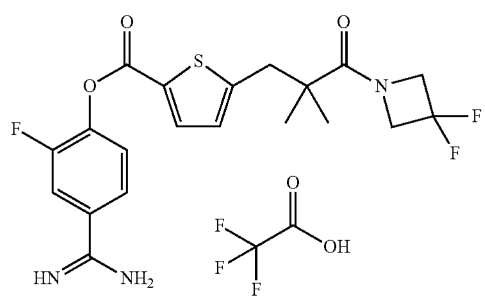 [SMILES: CC(C)(Cc1ccc(C(=O)Oc2ccc(C(=N)N)cc2F)s1)C(=O)N1CC(F)(F)C1 ; O=C(O)C(F)(F)F] | MS (ESI) m/z 440 (M + H)+ |
| 47 | 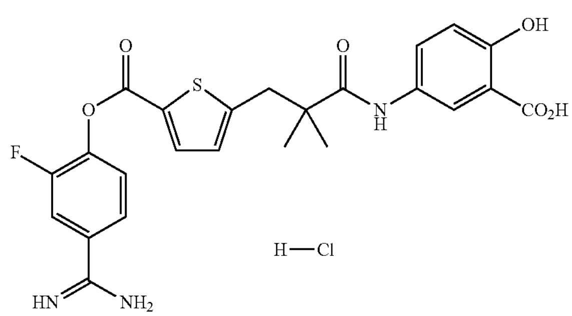 [SMILES: CC(C)(Cc1ccc(C(=O)Oc2ccc(C(=N)N)cc2F)s1)C(=O)Nc1ccc(O)c(C(=O)O)c1 ; Cl] | MS (ESI) m/z 500 (M + H)+ |
| 48 | 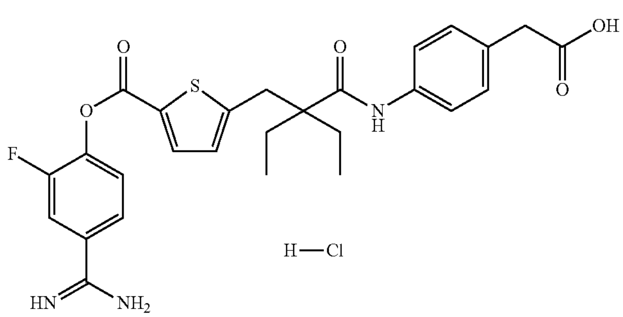 [SMILES: CCC(CC)(Cc1ccc(C(=O)Oc2ccc(C(=N)N)cc2F)s1)C(=O)Nc1ccc(CC(=O)O)cc1 ; Cl] | 1H NMR (400 MHz, DMSO-d6) δ 12.35 (1H, s), 9.50-9.17 (4H, m), 8.03-7.96 (2H, m), 7.83-7.77 (2H, m), 7.60 (2H, d, J = 8.0 Hz), 7.25 (2H, d, J = 8.0 Hz), 7.14 (1H, d, J = 8.0), 3.57 (2H, s), 3.34 (2H, s), 1.79-1.65 (4H, m), 0.92 (6H, t, J = 8.0 Hz).<br>MS (ESI) m/z 526 (M + H)+ |

TABLE 1-continued

| Compound No. | Structure | Analysis data |
|---|---|---|
| 49 | 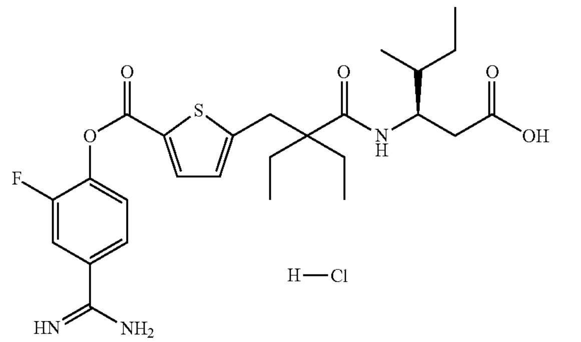 [SMILES: CCC(C)[C@@H](CC(=O)O)NC(=O)C(CC)(CC)Cc1ccc(C(=O)Oc2ccc(C(=N)N)cc2F)s1 ; Cl] | 1H NMR (400 MHz, DMSO-d6) δ 12.09 (1H, s), 9.44 (2H, s), 9.17 (2H, s), 7.98-7.91 (2H, m), 7.78-7.72 (2H, m), 7.37 (1H, d, J = 8.2 Hz), 7.06 (1H, d, J = 3.8 Hz), 4.19-4.09 (1H, m), 3.17-3.06 (2H, m), 2.43-2.30 (2H, m), 1.63-1.44 (4H, m), 1.40-1.27 (1H, m), 1.11-0.98 (1H, m), 0.89-0.73 (10H, m)<br>MS (ESI) m/z 520 (M + H)+ |
| 50 | 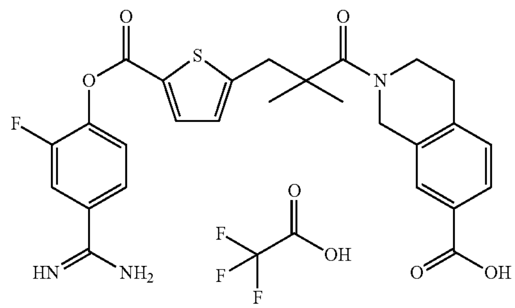 [SMILES: CC(C)(Cc1ccc(C(=O)Oc2ccc(C(=N)N)cc2F)s1)C(=O)N1CCc2ccc(C(=O)O)cc2C1 ; O=C(O)C(F)(F)F] | 1H NMR (400 MHz, DMSO-d6) δ 12.86 (1H, br s), 9.41 (2H, s), 9.14 (2H, s), 7.96-7.85 (3H, m), 7.77-7.70 (3H, m), 7.29 (1H, d, J = 8.0 Hz), 7.07 (1H, d, J = 3.8 Hz), 4.82 (2H, s), 3.89-3.80 (2H, m), 2.93-2.85 (2H, m), 1.30 (6H, s), 1.04 (2H, d, J = 6.1 Hz)<br>MS (ESI) m/z 524 (M + H)+ |
| 51 | 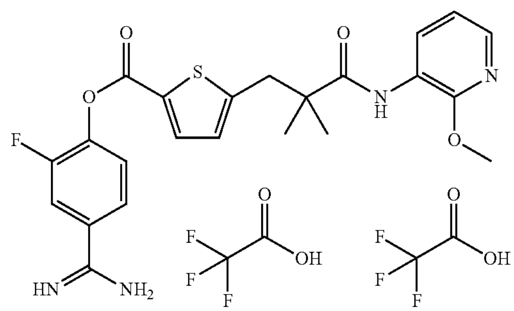 | MS (ESI) m/z 471 (M + H)+ |
| 52 | 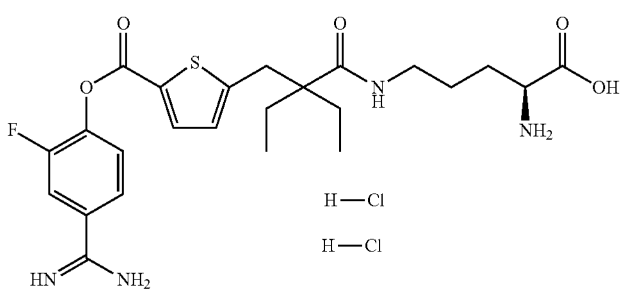 | 1H NMR (400 MHz, DMSO-d6) δ 9.45 (2H, br s), 9.30 (2H, br s), 8.00-7.91 (2H, m), 7.91-7.82 (1H, m), 7.82-7.69 (2H, m), 7.04 (1H, d, J = 3.9 Hz), 3.83-3.64 (1H, m), 3.19-3.04 (4H, m), 1.86-1.64 (2H, m), 1.64-1.37 (4H, m), 0.80 (6H, t, J = 7.4 Hz)<br>MS (ESI) m/z 507 (M + H)+ |
| 53 | 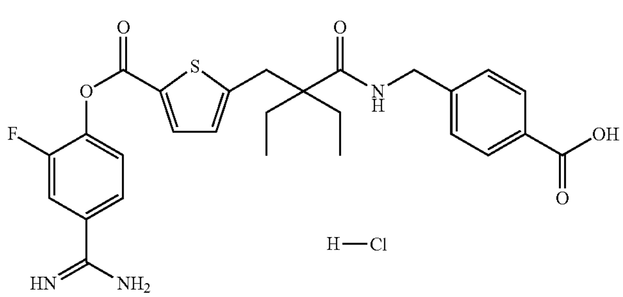 [SMILES: CCC(CC)(Cc1ccc(C(=O)Oc2ccc(C(=N)N)cc2F)s1)C(=O)NCc1ccc(C(=O)O)cc1 ; Cl] | MS (ESI) m/z 526 (M + H)+ |

TABLE 1-continued
| Compound No. | Structure | Analysis data |
|---|---|---|
| 54 | 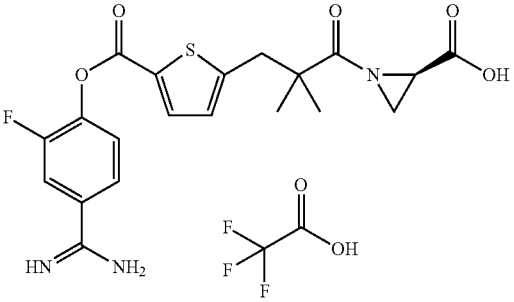 [SMILES: CC(C)(Cc1ccc(C(=O)Oc2ccc(C(=N)N)cc2F)s1)C(=O)N1C[C@@H]1C(=O)O ; O=C(O)C(F)(F)F] | MS (ESI) m/z 434 (M + H)+ |
| 55 | 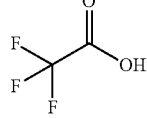 | MS (ESI) m/z 471 (M + H)+ |
| 56 | 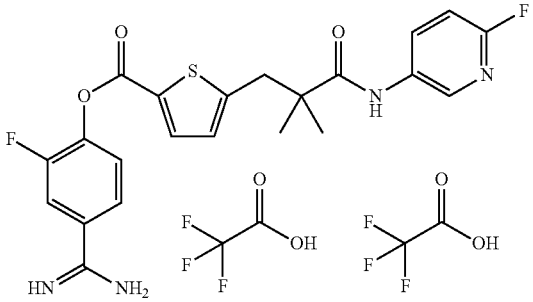 | 1H NMR (400 MHz, DMSO-d6) δ 9.31 (4H, br s), 8.09 (1H, s), 7.97-7.89 (2H, m), 7.79-7.70 (2H, m), 7.08 (1H, d, J = 3.9 Hz), 3.14 (2H, s), 2.30-2.14 (2H, m), 1.88 (4H, dd, J = 14.5, 6.8 Hz), 1.15 (6H, s)<br>MS (ESI) m/z 462 (M + H)+ |
| 57 | 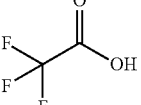 | MS (ESI) m/z 448 (M + H)+ |
| 58 | 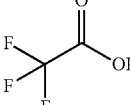 | MS (ESI) m/z 594 (M + H)+ |

TABLE 1-continued
| Compound No. | Structure | Analysis data |
|---|---|---|
| 59 | 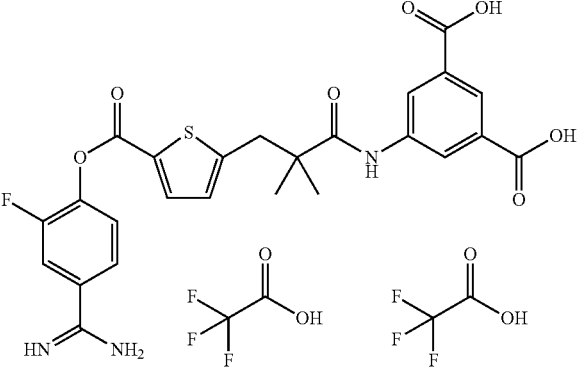 [SMILES: CC(C)(Cc1ccc(C(=O)Oc2ccc(C(=N)N)cc2F)s1)C(=O)Nc1cc(C(=O)O)cc(C(=O)O)c1 ; O=C(O)C(F)(F)F ; O=C(O)C(F)(F)F] | MS (ESI) m/z 528 (M + H)+ |
| 60 | 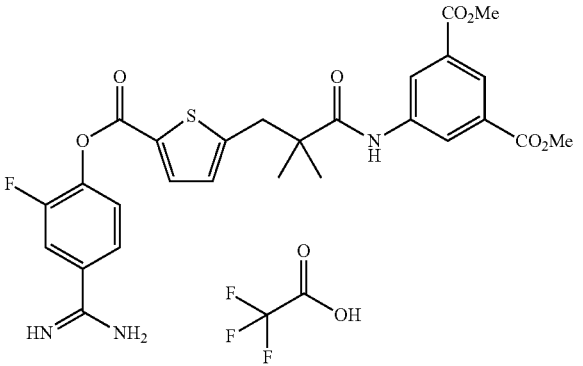 [SMILES: COC(=O)c1cc(NC(=O)C(C)(C)Cc2ccc(C(=O)Oc3ccc(C(=N)N)cc3F)s2)cc(C(=O)OC)c1 ; O=C(O)C(F)(F)F] | MS (ESI) m/z 542 (M + H)+ |
| 61 | 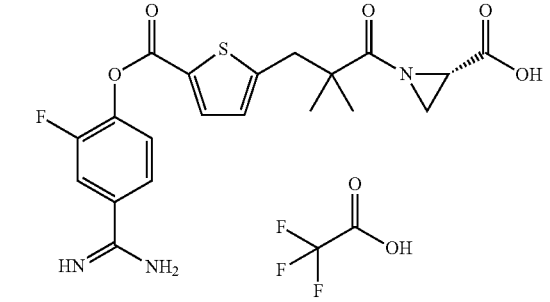 [SMILES: CC(C)(Cc1ccc(C(=O)Oc2ccc(C(=N)N)cc2F)s1)C(=O)N1C[C@H]1C(=O)O ; O=C(O)C(F)(F)F] | MS (ESI) m/z 434 (M + H)+ |
| 62 | 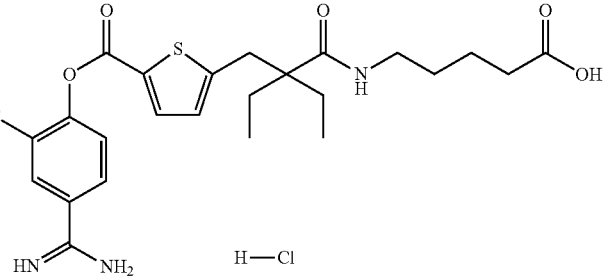 | 1H NMR (400 MHz, DMSO-d6) δ 11.98 (1H, br s), 9.44 (2H, s), 9.18 (2H, s), 7.95-7.92 (2H, m), 7.78-7.69 (m, 3H), 7.04 (1H, d, J = 3.9 Hz), 3.12-3.08 (4H, m), 2.20 (2H, t, J = 6.6 Hz), 1.59-1.40 (8H, m), 0.79 (6H, t, J = 7.4 Hz). MS (ESI) m/z 492 (M + H)+ |

TABLE 1-continued

| Compound No. | Structure | Analysis data |
|---|---|---|
| 63 | 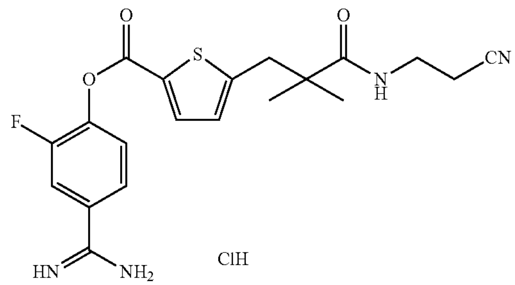 [SMILES: CC(C)(Cc1ccc(C(=O)Oc2ccc(C(=N)N)cc2F)s1)C(=O)NCCC#N ; Cl] | MS (ESI) m/z 417 (M + H)+ |
| 64 | 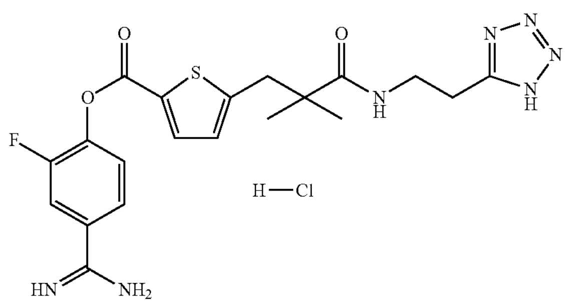 [SMILES: CC(C)(Cc1ccc(C(=O)Oc2ccc(C(=N)N)cc2F)s1)C(=O)NCCc1nnn[nH]1 ; Cl] | 1H NMR (400 MHz, DMSO-d6) δ 9.47 (2H, s), 9.21 (2H, s), 7.98-7.86 (3H, m), 7.79-7.73 (2H, m), 6.99 (1H, d, J = 3.8 Hz), 3.46 (2H, dd, J = 12.8, 7.1 Hz), 3.09 (2H, s), 3.05 (2H, t, J = 7.1 Hz), 1.10 (6H, s)<br>MS (ESI) m/z 460 (M + H)+ |
| 65 | 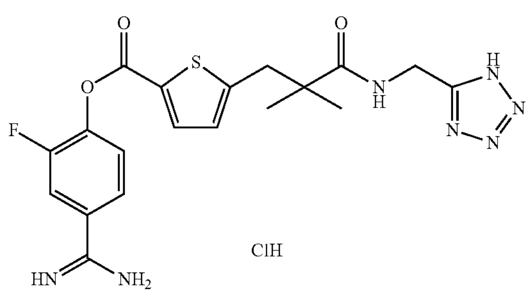 [SMILES: CC(C)(Cc1ccc(C(=O)Oc2ccc(C(=N)N)cc2F)s1)C(=O)NCc1nnn[nH]1 ; Cl] | 1H NMR (400 MHz, DMSO-d6) δ 9.45 (2H, s), 9.22 (2H, s), 8.50 (1H, t, J = 5.5 Hz), 7.98-7.92 (1H, m), 7.89 (1H, d, J = 3.8 Hz), 7.79-7.73 (2H, m), 6.99 (1H, d, J = 3.8 Hz), 4.54 (2H, d, J = 5.6 Hz), 3.13 (2H, s), 1.17 (6H, s)<br>MS (ESI) m/z 446 (M + H)+ |
| 66 | 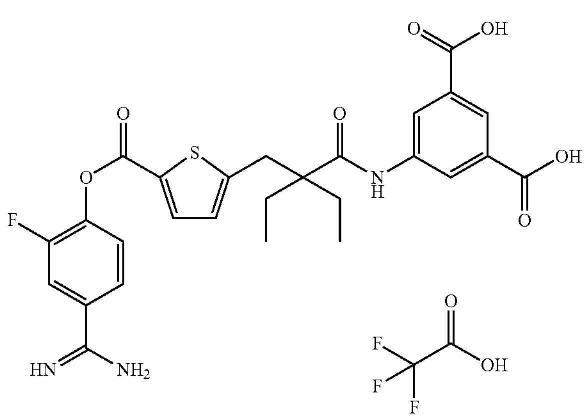 [SMILES: CCC(CC)(Cc1ccc(C(=O)Oc2ccc(C(=N)N)cc2F)s1)C(=O)Nc1cc(C(=O)O)cc(C(=O)O)c1 ; O=C(O)C(F)(F)F] | 1H NMR (400 MHz, DMSO-d6) δ 9.87 (1H, br s), 9.40 (2H, br s), 9.29 (2H, s), 8.54 (2H, d, J = 2.0 Hz), 8.19 (1H, t, J = 2.0 Hz), 7.96 (1H, d, J = 4.0 Hz), 7.94-7.92 (1H, m), 7.91-7.89 (1H, m), 7.75-7.72 (2H, m), 7.09 (1H, d, J = 4.0 Hz), 1.83-1.51 (4H, m), 0.87 (6H, t, J = 7.0 Hz)<br>MS (ESI) m/z 556 (M + H)+ |

TABLE 1-continued

| Compound No. | Structure | Analysis data |
|---|---|---|
| 67 | 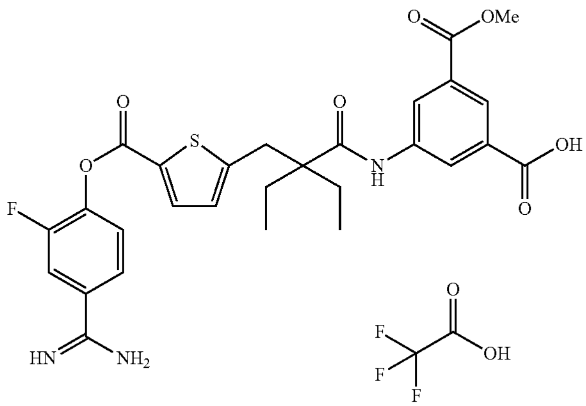 | MS (ESI) m/z 570 (M + H)+ |
| 68 | 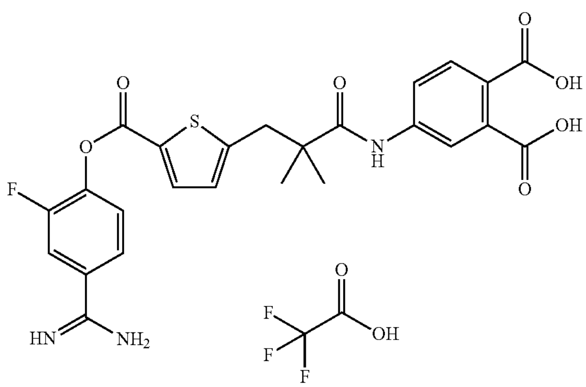 [SMILES: CC(C)(Cc1ccc(C(=O)Oc2ccc(C(=N)N)cc2F)s1)C(=O)Nc1ccc(C(=O)O)c(C(=O)O)c1 ; O=C(O)C(F)(F)F] | MS (ESI) m/z 528 (M + H)+ |
| 69 | 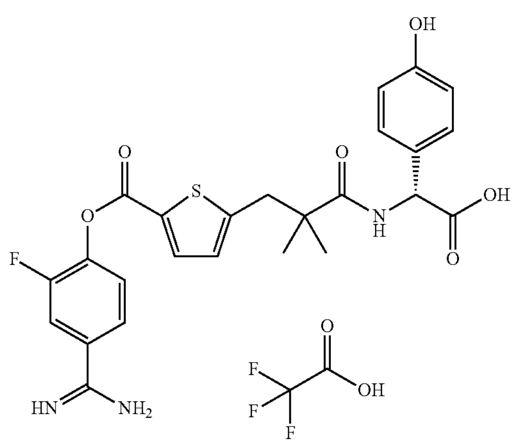 [SMILES: CC(C)(Cc1ccc(C(=O)Oc2ccc(C(=N)N)cc2F)s1)C(=O)N[C@@H](C(=O)O)c1ccc(O)cc1 ; O=C(O)C(F)(F)F] | 1H NMR (400 MHz, DMSO-d6) δ 9.47-9.30 (4H, br), 7.95-7.78 (2H, m), 7.71-7.63 (2H, m), 7.10 (2H, d, J = 9.0 Hz), 6.93 (1H, d, J = 4.0 Hz), 6.64 (2H, d, J = 9.0 Hz), 5.11 (1H, s), 3.09 (3H, d, J = 2.0 Hz), 1.11 (6H, d, J = 6.0 Hz)<br>MS (ESI) m/z 514 (M + H)+ |
| 70 | 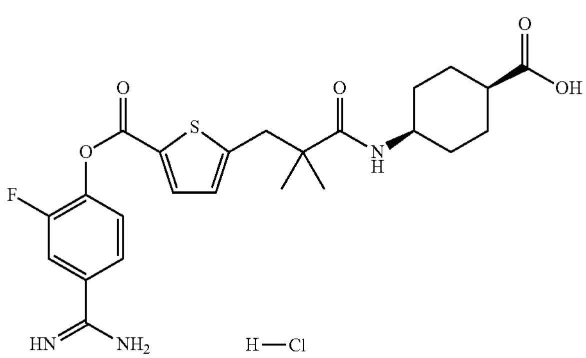 [SMILES: CC(C)(Cc1ccc(C(=O)Oc2ccc(C(=N)N)cc2F)s1)C(=O)N[C@H]1CC[C@@H](C(=O)O)CC1 ; Cl] | MS (ESI) m/z 490 (M + H)+ |

TABLE 1-continued

| Compound No. | Structure | Analysis data |
|---|---|---|
| 71 | 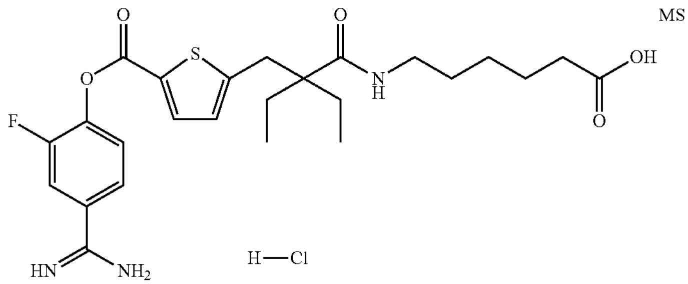 | MS (ESI) m/z 506 (M + H)+ |
| 72 | 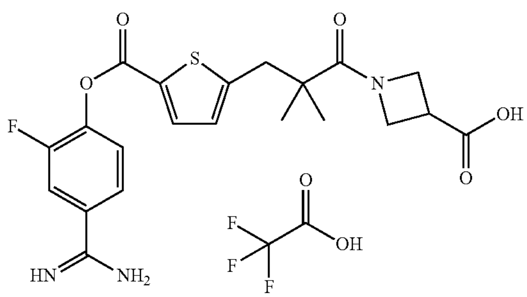 [SMILES: CC(C)(Cc1ccc(C(=O)Oc2ccc(C(=N)N)cc2F)s1)C(=O)N1CC(C(=O)O)C1 ; O=C(O)C(F)(F)F] | 1H NMR (400 MHz, DMSO-d6) δ 9.41 (2H, s), 9.17 (2H, s), 7.98-7.89 (2H, m), 7.81-7.70 (2H, m), 7.08 (1H, d, J = 4.0 Hz), 4.64-4.18 (2H, m), 4.11-3.79 (2H, m), 3.10 (2H, s), 1.15 (6H, s)<br>MS (ESI) m/z 448 (M + H)+ |
| 73 | 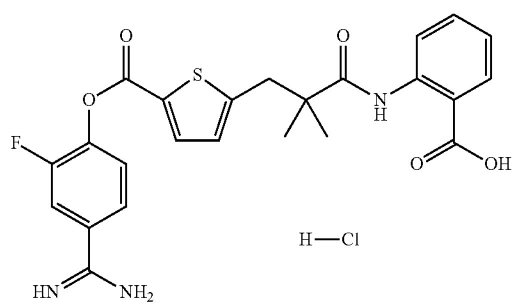 [SMILES: CC(C)(Cc1ccc(C(=O)Oc2ccc(C(=N)N)cc2F)s1)C(=O)Nc1ccccc1C(=O)O ; Cl] | MS (ESI) m/z 484 (M + H)+ |
| 74 | 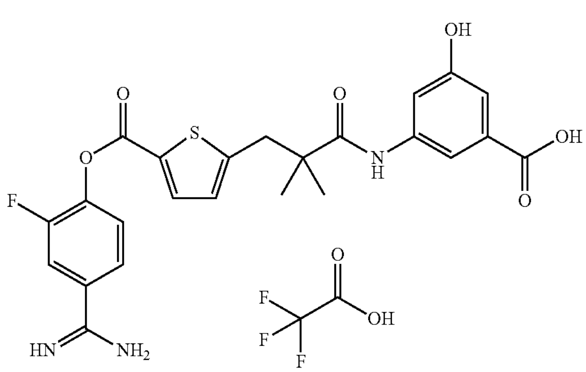 [SMILES: CC(C)(Cc1ccc(C(=O)Oc2ccc(C(=N)N)cc2F)s1)C(=O)Nc1cc(O)cc(C(=O)O)c1 ; O=C(O)C(F)(F)F] | MS (ESI) m/z 500 (M + H)+ |

TABLE 1-continued
| Compound No. | Structure | Analysis data |
|---|---|---|
| 75 | 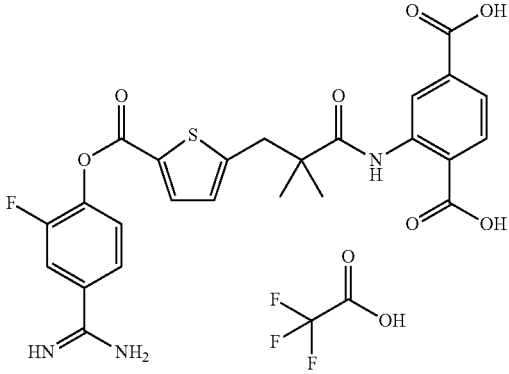 [SMILES: CC(C)(Cc1ccc(C(=O)Oc2ccc(C(=N)N)cc2F)s1)C(=O)Nc1cc(C(=O)O)ccc1C(=O)O ; O=C(O)C(F)(F)F] | MS (ESI) m/z 528 (M + H)+ |
| 76 | 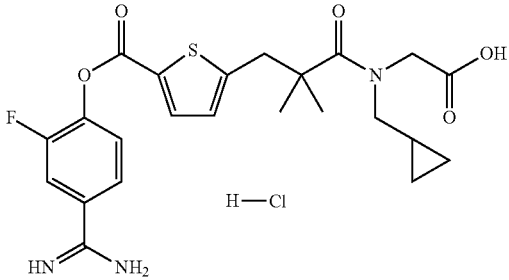 [SMILES: CC(C)(Cc1ccc(C(=O)Oc2ccc(C(=N)N)cc2F)s1)C(=O)N(CC(=O)O)CC1CC1 ; Cl] | MS (ESI) m/z 476 (M + H)+ |
| 77 | 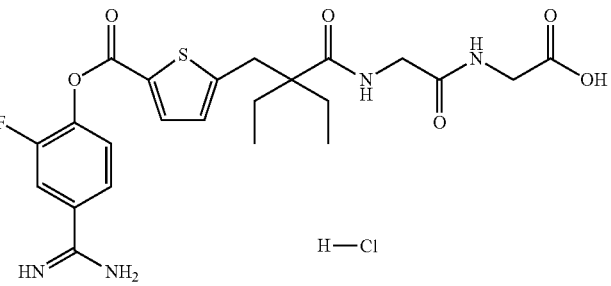 | MS (ESI) m/z 507 (M + H)+ |
| 78 | 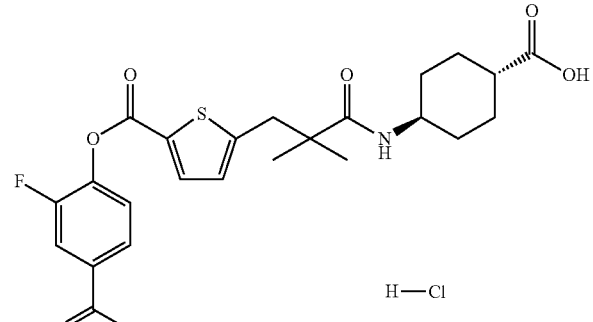 | MS (ESI) m/z 490 (M + H)+ |

TABLE 1-continued

| Compound No. | Structure | Analysis data |
| --- | --- | --- |
| 79 | 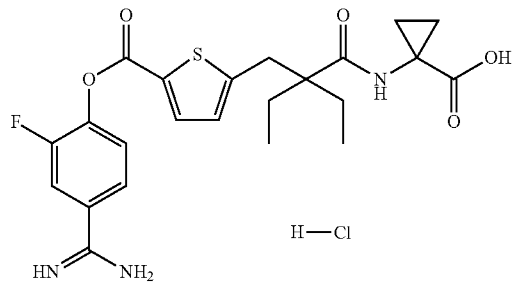 [SMILES: CCC(CC)(Cc1ccc(C(=O)Oc2ccc(C(=N)N)cc2F)s1)C(=O)NC1(C(=O)O)CC1 ; Cl] | MS (ESI) m/z 476 (M + H)+ |
| 80 | 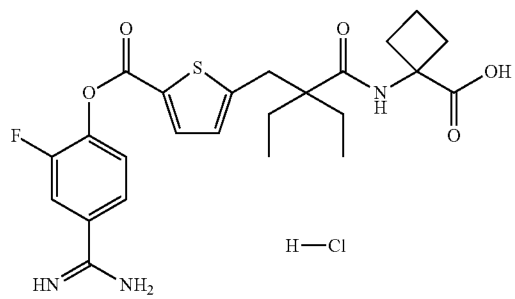 [SMILES: CCC(CC)(Cc1ccc(C(=O)Oc2ccc(C(=N)N)cc2F)s1)C(=O)NC1(C(=O)O)CCC1 ; Cl] | MS (ESI) m/z 490 (M + H)+ |
| 81 | 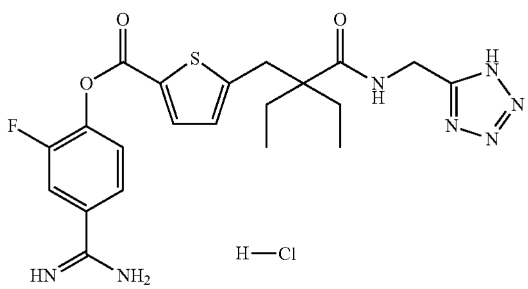 [SMILES: CCC(CC)(Cc1ccc(C(=O)Oc2ccc(C(=N)N)cc2F)s1)C(=O)NCc1nnn[nH]1 ; Cl] | 1H NMR (400 MHz, DMSO-d6) δ 9.47 (1H, s), 9.21 (1H, s), 8.57 (1H, s), 7.95 (1H, d, J = 11.6 Hz), 7.89 (1H, d, J = 3.8 Hz), 7.80-7.72 (1H, m), 7.00 (1H, d, J = 3.8 Hz), 7.00 (1H, d, J = 3.8 Hz), 4.55 (1H, d, J = 5.5 Hz), 3.14 (1H, s), 1.62-1.42 (1H, m), 0.78 (1H, t, J = 7.4 Hz) MS (ESI) m/z 474 (M + H)+ |
| 82 | 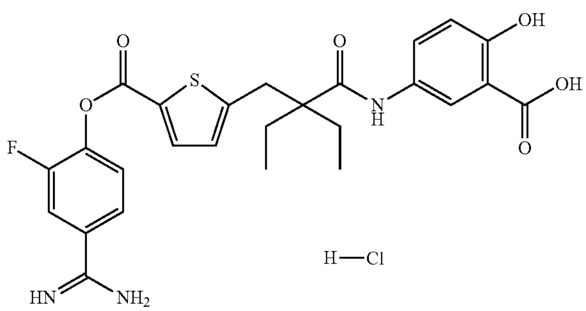 [SMILES: CCC(CC)(Cc1ccc(C(=O)Oc2ccc(C(=N)N)cc2F)s1)C(=O)Nc1ccc(O)c(C(=O)O)c1 ; Cl] | MS (ESI) m/z 528 (M + H)+ |
| 83 | 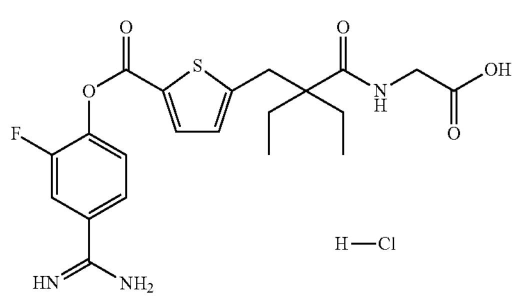 [SMILES: CCC(CC)(Cc1ccc(C(=O)Oc2ccc(C(=N)N)cc2F)s1)C(=O)NCC(=O)O ; Cl] | MS (ESI) m/z 450 (M + H)+ |

TABLE 1-continued

| Compound No. | Structure | Analysis data |
|---|---|---|
| 84 | 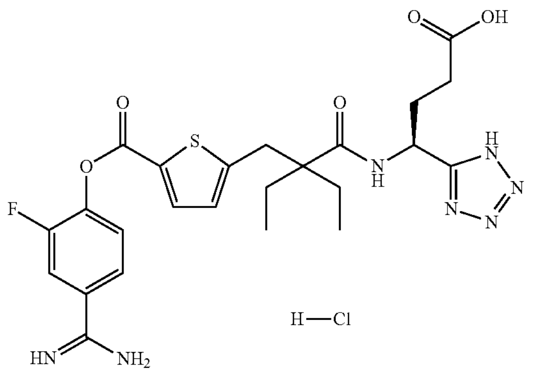 [SMILES: CCC(CC)(Cc1ccc(C(=O)Oc2ccc(C(=N)N)cc2F)s1)C(=O)N[C@@H](CCC(=O)O)c1nnn[nH]1 ; Cl] | 1H NMR (400 MHz, DMSO-d6) δ 9.46 (2H, s), 9.18 (2H, s), 8.27 (1H, d, J = 7.6 Hz), 7.97-7.92 (1H, m), 7.87 (1H, d, J = 3.8 Hz), 7.79-7.73 (2H, m), 6.98 (1H, d, J = 3.8 Hz), 5.29 (1H, dd, J = 14.4, 8.1 Hz), 3.20-3.09 (2H, m), 2.36-2.06 (4H, m), 1.61-1.48 (4H, m), 0.77 (6H, dt, J = 20.1, 7.4 Hz)<br>MS (ESI) m/z 546 (M + H)+ |
| 85 | 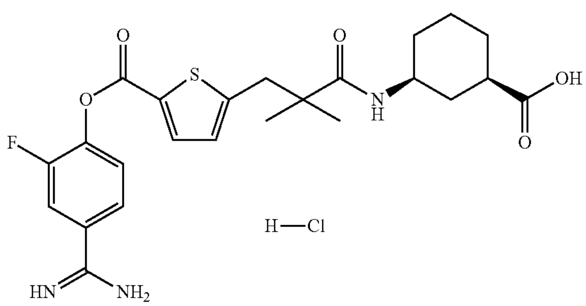 [SMILES: CC(C)(Cc1ccc(C(=O)Oc2ccc(C(=N)N)cc2F)s1)C(=O)N[C@H]1CCC[C@@H](C(=O)O)C1 ; Cl] | MS (ESI) m/z 490 (M + H)+ |
| 86 | 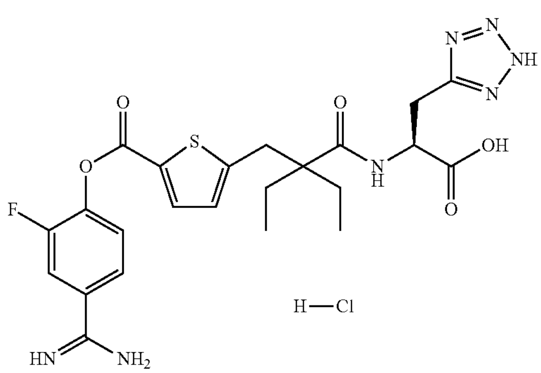 [SMILES: CCC(CC)(Cc1ccc(C(=O)Oc2ccc(C(=N)N)cc2F)s1)C(=O)N[C@@H](Cc1nn[nH]n1)C(=O)O ; Cl] | 1H NMR (400 MHz, DMSO-d6) δ 9.41 (2H, s), 9.16 (2H, s), 8.11 (1H, d, J = 8.1 Hz), 7.96-7.85 (2H, m), 7.81-7.70 (2H, m), 6.98 (1H, d, J = 3.9 Hz), 4.88-4.78 (1H, m), 3.46-3.26 (2H, m), 3.08 (2H, s), 1.55-1.33 (4H, m), 0.75 (3H, t, J = 7.4 Hz), 0.65 (3H, t, J = 7.4 Hz)<br>MS (ESI) m/z 532 (M + H)+ |
| 87 | 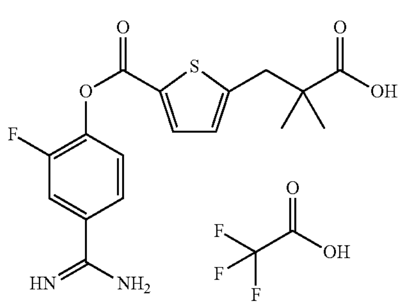 [SMILES: CC(C)(Cc1ccc(C(=O)Oc2ccc(C(=N)N)cc2F)s1)C(=O)O ; O=C(O)C(F)(F)F] | 1H-NMR (400 MHz, DMSO-d6) δ 9.41 (2H, br s), 9.10 (2H, br s), 7.96 (1H, d, J = 4.0 Hz), 7.93 (1H, d, J = 8.1 Hz), 7.80-7.70 (2H, m), 7.09 (1H, d, J = 4.0 Hz), 3.14 (2H, s), 1.16 (6H, s).<br>MS (ESI) m/z 365 (M + H)+ |

TABLE 1-continued

| Compound No. | Structure | Analysis data |
|---|---|---|
| 88 | 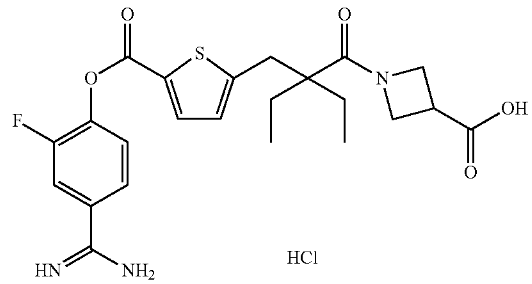 [SMILES: CCC(CC)(Cc1ccc(C(=O)Oc2ccc(C(=N)N)cc2F)s1)C(=O)N1CC(C(=O)O)C1 ; Cl] | 1H NMR (400 MHz, DMSO-d6) δ 9.43 (2H, s), 9.21 (2H, s), 8.01-7.89 (2H, m), 7.83-7.70 (2H, m), 7.09 (1H, d, J = 3.8 Hz), 4.62-4.41 (1H, m), 4.41-4.21 (2H, m), 4.21-3.98 (2H, m), 3.98-3.80 (1H, m), 3.46-3.35 (1H, m), 3.12 (2H, s), 1.62-1.39 (4H, m), 0.83 (6H, t, J = 7.4 Hz). MS (ESI) m/z 476 (M + H)+ |
| 89 | 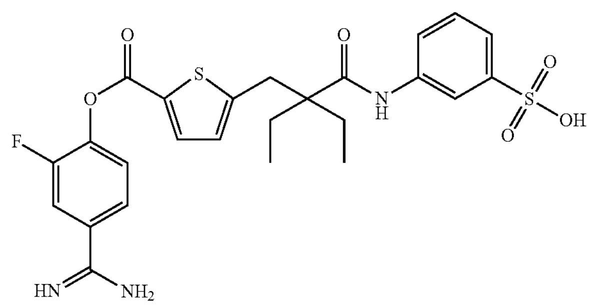 [SMILES: CCC(CC)(Cc1ccc(C(=O)Oc2ccc(C(=N)N)cc2F)s1)C(=O)Nc1cccc(S(=O)(=O)O)c1] | 1H-NMR (400 MHz, DMSO-d6) δ 9.55 (1H, s), 9.41 (2H, s), 9.03 (2H, s), 7.97-7.82 (3H, m), 7.82-7.65 (3H, m), 7.34-7.20 (2H, m), 7.08 (1H, d, J = 3.9 Hz), 3.30 (2H, s), 1.79-1.56 (4H, m), 0.85 (6H, t, J = 7.3 Hz). MS (ESI) m/z 548 (M + H)+ |
| 90 | 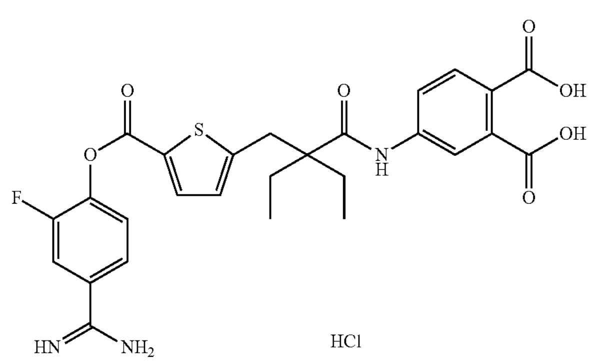 [SMILES: CCC(CC)(Cc1ccc(C(=O)Oc2ccc(C(=N)N)cc2F)s1)C(=O)Nc1ccc(C(=O)O)c(C(=O)O)c1 ; Cl] | 1H-NMR (400 MHz, DMSO-d6) δ 9.80 (1H, s), 9.41 (2H, s), 9.07 (2H, s), 8.58 (1H, d, J = 4.8 Hz), 8.15 (1H, s), 7.98-7.88 (3H, m), 7.82-7.66 (2H, m), 7.08 (1H, d, J = 3.9 Hz), 3.3-3.25 (2H, m), 1.86-1.57 (4H, m), 0.85 (6H, t, J = 7.3 Hz). MS (ESI) m/z 556 (M + H)+ |
| 91 | 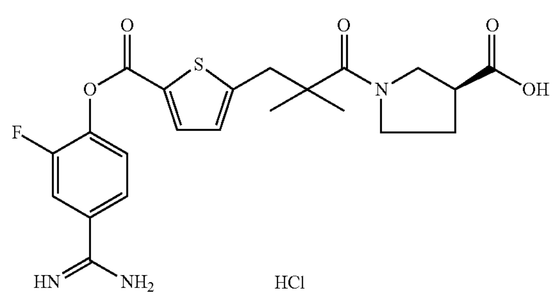 [SMILES: CC(C)(Cc1ccc(C(=O)Oc2ccc(C(=N)N)cc2F)s1)C(=O)N1CC[C@H](C(=O)O)C1 ; Cl] | 1H-NMR (400 MHz, DMSO-d6) δ 12.52 (1H, s), 9.44 (2H, s), 9.16 (2H, s), 7.99-7.89 (2H, m), 7.80-7.71 (2H, m), 7.08 (1H, d, J = 3.8 Hz), 3.81-3.53 (4H, m), 3.19 (2H, m), 3.10-2.90 (1H, m), 2.25-1.85 (2H, m), 1.22 (6H, s). MS (ESI) m/z 462 (M + H)+ |

TABLE 1-continued

| Compound No. | Structure | Analysis data |
|---|---|---|
| 92 | 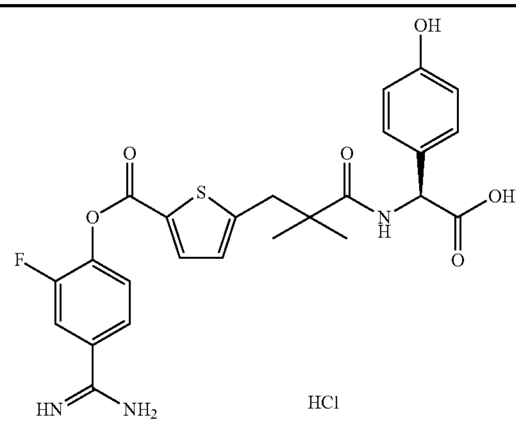 | 1H-NMR (400 MHz, DMSO-d6) δ 9.46 (1H, s), 9.41 (2H, s), 9.10 (2H, s), 8.06 (1H, d, J = 7.2 Hz), 7.96-7.90 (1H, m), 7.89 (1H, d, J = 3.8 Hz), 7.81-7.69 (2H, m), 7.20 (2H, d, J = 8.6 Hz), 7.01 (1H, d, J = 3.8 Hz), 6.73 (2H, d, J = 8.6 Hz), 5.26 (1H, d, J = 7.1 Hz), 3.17 (2H, s), 1.17 (6H, s). MS (ESI) m/z 514 (M + H)+ |
| 93 | 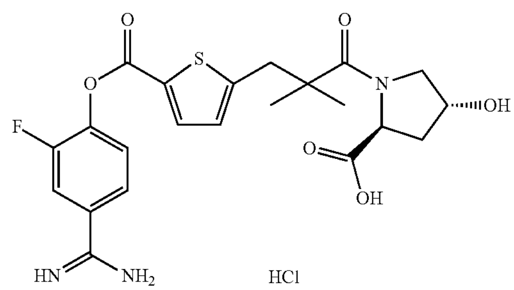 [SMILES: CC(C)(Cc1ccc(C(=O)Oc2ccc(C(=N)N)cc2F)s1)C(=O)N1C[C@H](O)C[C@H]1C(=O)O ; Cl] | 1H-NMR (400 MHz, DMSO-d6) δ 9.44 (2H, s), 9.14 (2H, s), 7.97-7.87 (2H, m), 7.80-7.70 (2H, m), 7.13 (1H, d, J = 3.8 Hz), 5.18 (1H, m), 4.40-4.27 (2H, m), 3.77-3.63 (2H, m), 3.25 (1H, d, J = 14.1 Hz), 3.10 (1H, d, J = 14.2 Hz), 2.11-2.00 (1H, m), 1.87-1.75 (1H, m), 1.22 (6H, s). MS (ESI) m/z 478 (M + H)+ |
| 94 | 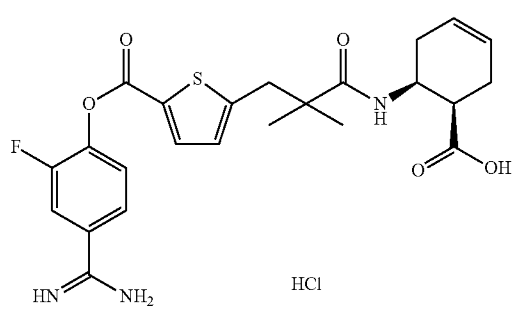 [SMILES: CC(C)(Cc1ccc(C(=O)Oc2ccc(C(=N)N)cc2F)s1)C(=O)N[C@H]1CC=CC[C@H]1C(=O)O ; Cl] | 1H-NMR (400 MHz, DMSO-d6) δ 9.44 (2H, s), 9.14 (2H, s), 7.98-7.90 (2H, m), 7.80-7.70 (2H, m), 7.13-7.01 (2H, m), 5.68-5.61 (1H, m), 5.61-5.54 (1H, m), 4.25-4.13 (1H, m), 3.21-3.06 (2H, m), 2.82-2.73 (1H, m), 2.48-2.38 (1H, m), 2.32-2.12 (3H, m), 1.14 (6H, d, J = 5.2 Hz). MS (ESI) m/z 488 (M + H)+ |

Experimental Example 1

Measurement of Trypsin Inhibitory Activity

Using a 96 well plate (#3915, Costar), a test compound (25 µL) was mixed with 20 µM fluorescence enzyme substrate (Boc-Phe-Ser-Arg-AMC, 50 µL) mixed with 200 mM Tris-HCl buffer (pH 8.0), and human trypsin (Sigma, 25 µL) was added. Using a fluorescence plate reader fmax (Molecular Devices, Inc.), the reaction rate was measured from the time-course changes at excitation wavelength 355 nm and fluorescence wavelength 460 nm. The Ki value was calculated from the concentration of the test compound, reciprocal of reaction rate, and Km value of the enzyme substrate, and by using Dixon plot. The results are shown in Table 2.

Experimental Example 2

Measurement of Enteropeptidase Inhibitory Activity

Using a 96 well plate (#3915, Costar), a test compound (25 µL), 400 mM Tris-HCl buffer (pH 8.0, 25 µL) and 0.5 mg/mL, fluorescence enzyme substrate (Gly-Asp-Asp-Asp-Asp-Lys-β-Naphtylamide, 25 µL) were mixed, and recombinant human enteropeptidase (R&D Systems, Inc., 25 µL) was added. Using a fluorescence plate reader fmax (Molecular Devices, Inc.), the reaction rate was measured from the time-course changes at excitation wavelength 320 nm and fluorescence wavelength 405 nm. The Ki value was calculated from the concentration of the test compound, reciprocal of reaction rate, and Km value of the enzyme substrate, and by using Dixon plot. The results are shown in Table 2.

TABLE 2

| Compound No. | Enteropeptidase inhibitory activity Ki (nM) | Trypsin inhibitory activity Ki (nM) |
|---|---|---|
| 1 | 0.14 | 0.61 |
| 2 | 0.73 | 4.10 |
| 3 | 0.29 | 0.42 |
| 4 | 0.46 | 0.75 |
| 5 | 0.24 | 0.50 |

TABLE 2-continued

| Compound No. | Enteropeptidase inhibitory activity Ki (nM) | Trypsin inhibitory activity Ki (nM) |
|---|---|---|
| 6 | 0.69 | 0.95 |
| 7 | 0.41 | 1.33 |
| 8 | 0.87 | 1.69 |
| 9 | 0.79 | 2.02 |
| 10 | 0.49 | 1.50 |
| 11 | 0.41 | 1.87 |
| 12 | 0.94 | 1.78 |
| 13 | 1.56 | 5.18 |
| 14 | 0.99 | 2.50 |
| 15 | 0.84 | 1.74 |
| 16 | 1.10 | 8.30 |
| 17 | 1.69 | 6.38 |
| 18 | 1.24 | 2.49 |
| 19 | 0.33 | 0.82 |
| 20 | 2.61 | 7.91 |
| 21 | 0.88 | 1.76 |
| 22 | 1.00 | 3.57 |
| 23 | 1.81 | 3.17 |
| 24 | 0.27 | 2.01 |
| 25 | 0.26 | 1.04 |
| 26 | 1.33 | 3.10 |
| 27 | 0.73 | 1.67 |
| 28 | 0.65 | 1.93 |
| 29 | 1.18 | 3.84 |
| 30 | 0.94 | 2.73 |
| 31 | 1.08 | 2.89 |
| 32 | 1.43 | 0.70 |
| 33 | 1.02 | 2.00 |
| 34 | 2.56 | 2.73 |
| 35 | 2.56 | 3.04 |
| 36 | 4.70 | 3.07 |
| 37 | 0.96 | 1.51 |
| 38 | 0.97 | 1.45 |
| 39 | 7.56 | 3.60 |
| 40 | 6.66 | 4.54 |
| 41 | 1.58 | 3.88 |
| 42 | 1.69 | 3.88 |
| 43 | 0.42 | 1.96 |
| 44 | 0.67 | 1.69 |
| 45 | 4.13 | 3.36 |
| 46 | 5.27 | 3.89 |
| 47 | 0.53 | 0.92 |
| 48 | 2.41 | 3.35 |
| 49 | 3.26 | 1.97 |
| 50 | 3.46 | 3.49 |
| 51 | 3.75 | 1.87 |
| 52 | 5.53 | 5.78 |
| 53 | 2.69 | 9.27 |
| 54 | 1.76 | 1.53 |
| 55 | 2.51 | 3.30 |
| 56 | 0.51 | 1.49 |
| 57 | 0.67 | 1.01 |
| 58 | 0.71 | 1.59 |
| 59 | 0.31 | 0.49 |
| 60 | 1.22 | 1.02 |
| 61 | 1.13 | 0.96 |
| 62 | 0.98 | 5.17 |
| 63 | 2.90 | 3.65 |
| 64 | 0.53 | 1.60 |
| 65 | 0.53 | 0.75 |
| 66 | 0.71 | 1.58 |
| 67 | 3.73 | 4.40 |
| 68 | 0.24 | 0.21 |
| 69 | 0.72 | 1.14 |
| 70 | 1.11 | 1.70 |
| 71 | 4.97 | 8.01 |
| 72 | 0.63 | 1.85 |
| 73 | 2.41 | 3.65 |
| 74 | 0.58 | 0.18 |
| 75 | 0.39 | 3.72 |
| 76 | 0.67 | 2.01 |
| 77 | 0.69 | 1.42 |
| 78 | 1.53 | 2.57 |
| 79 | 1.12 | 2.19 |
| 80 | 1.33 | 4.67 |
| 81 | 1.20 | 3.54 |
| 82 | 3.52 | 5.32 |
| 83 | 0.72 | 1.42 |
| 84 | 0.43 | 3.27 |
| 85 | 0.81 | 0.69 |
| 86 | 0.24 | 3.40 |
| 87 | 0.39 | 1.30 |
| 88 | 1.00 | 2.87 |
| 89 | 0.84 | 1.17 |
| 90 | 0.55 | 1.70 |
| 91 | 0.90 | 1.33 |
| 92 | 0.67 | 0.96 |
| 93 | 0.30 | 0.90 |
| 94 | 1.30 | 1.98 |

Thus, the compound of the present invention was confirmed to show superior enteropeptidase inhibitory activity and superior trypsin inhibitory activity. Therefore, it has been shown that the compound of the present invention having an inhibitory activity on enteropeptidase and trypsin decreases digestive capacity for protein, lipid, and carbohydrates, and is effective as a therapeutic or prophylactic drug for obesity and hyperlipidemia.

Experimental Example 3

Evaluation of Anti-Diabetic Action

Anti-diabetic action of the compound or pharmaceutical salt thereof of the present invention can be confirmed by, for example, the following procedure:
KK-$A^y$/JCL mice (male, 5-7 week-old, CLEA Japan, Inc.) known to spontaneously develop obese type 2 diabetes are purchased and, after one week of preliminary rearing period, randomly assigned to the groups (6 per group) with the body weight and non-fasting blood glucose levels as indices. The animals are individually housed in a polycarbonate cage and allowed to drink water freely from a watering bottle. During the test period, they are allowed to freely ingest a mixture of a test compound, which may be in salt form thereof (5.6 mg/100 g or 16.8 mg/100 g, for example) and powder feed CRF-1 (Oriental Yeast Co., Ltd.). CRF-1 alone is given to the control group. After one week of dosing period, an aspirate of the blood (6 µL) is collected from the tail vein, and the blood glucose level is determined by ACCU-CHEK Aviva (Roche Diagnostics K.K.).

Experimental Example 4

Evaluation of Hypoglycemic Action

Figure 2:
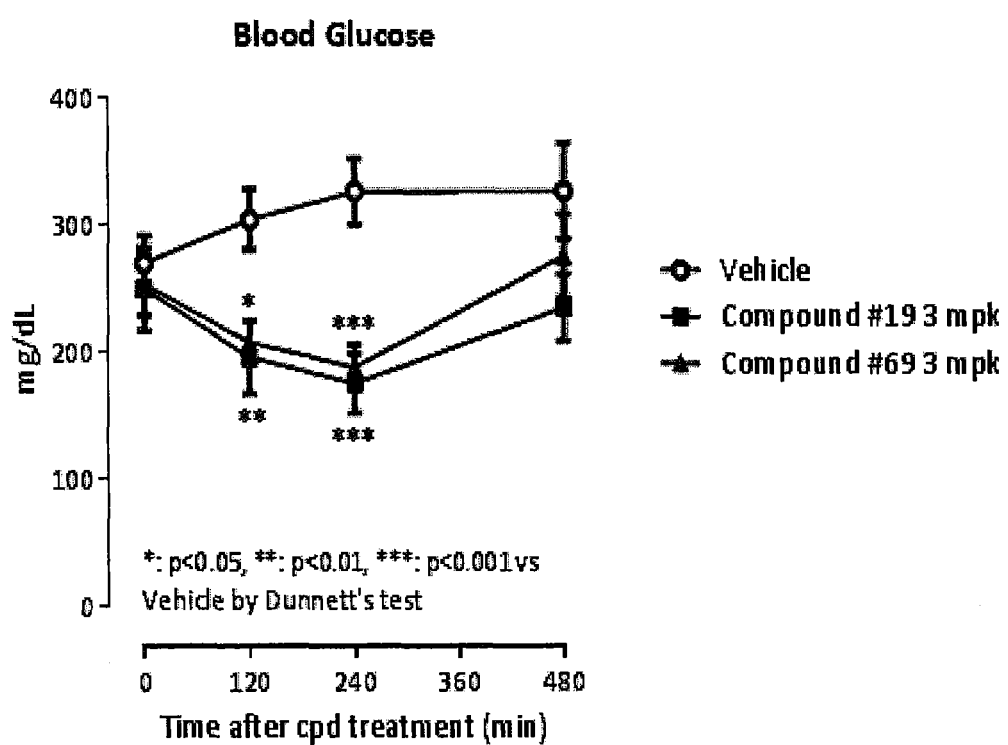
FIG. 2 shows blood glucose levels at 0, 2, 4, and 8 hours after dosing compounds of No. 19 and 69, and the vehicle at the dose of 3 mg/kg in KK-A$^y$/JCL mice.

Hypoglycemic action of some compounds was confirmed by, for example, the following procedure:
Zucker Fatty rats (male, 11-19 week-old, Charles River Japan, Inc.) known to spontaneously develop hyperglycemia were randomly assigned to the groups (6 per group). The animals were individually housed in a polycarbonate cage and allowed to drink water freely from a watering bottle. The animals in the compound groups were gavaged with compound No. 10, 87, 19, or 69 at the dose of 3 mg/kg. These compounds were used as HCl salt form thereof, converted by the method according to Example 3, step 6 from TFA salt form thereof upon the necessity. The animals in the control group were only treated with the vehicle (0.5% methylcellulose). Animals were allowed free access to the feed (CRF-1, Oriental Yeast Co., Ltd.) during the experiment. An aspirate of the blood (6 μL) was collected from the tail vein on the time point of immediately before dosing (time 0) as well as 2, 4, and 8 hours after dosing. The blood glucose levels were determined with ACCU-CHEK Aviva (Roche Diagnostics K.K.). Serial changes of blood glucose levels in the animals were shown in FIGS. 1 and 2. The blood glucose levels in the compound group were significantly decreased comparing with those in the vehicle group 2 or 4 hours after dosing.

Thus, the test compounds were confirmed to show a significant hypoglycemic action. The compound of the present invention having an enteropeptidase inhibitory activity and a trypsin inhibitory activity is shown to have a blood glucose elevation suppressing action or hypoglycemic action. In addition, it can also be shown that the compound of the present invention shows an insulin sensitizing activity and is also useful as a prophylactic or therapeutic agent for obesity, diabetic complications, or metabolic syndrome, since it shows a blood glucose elevation suppressing action or hypoglycemic action.

INDUSTRIAL APPLICABILITY

The trypsin and enteropeptidase inhibitory compound of the present invention can be used as an active ingredient of a therapeutic or prophylactic drug of diabetes or diabetic complications.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:
1. A method for treating hyperglycemia or diabetes, comprising administering an effective amount of a compound represented by formula (I):

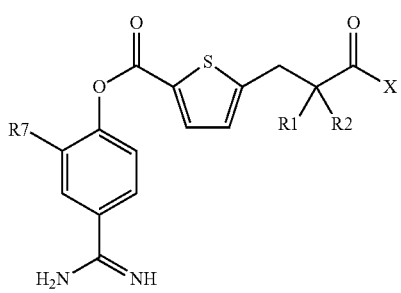

wherein:
$R^1$ and $R^2$ are the same or different and each is independently a $C_{1-4}$ alkyl group or a $C_{2-4}$ alkenyl group, or $R^1$ and $R^2$ together with the carbon atom to which they are bonded form a $C_{3-8}$ cycloalkane ring;
X is —$OR^3$, —$NR^4R^5$ or a group represented by formula (II):

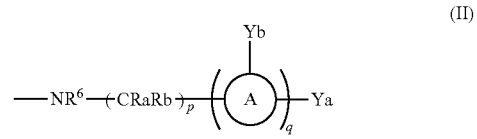

wherein:
$R^3$ is a hydrogen atom or a $C_{1-4}$ alkyl group;
$R^4$, $R^5$ and $R^6$ are the same or different and each is independently a hydrogen atom, a $C_{1-8}$ alkyl group, a carboxyl $C_{1-8}$ alkyl group or a $C_{3-8}$ alkenyl group, or $R^4$ and $R^5$ together with the nitrogen atom to which they are bonded form a $C_{3-9}$ heterocycle, wherein said $C_{1-8}$ alkyl group, said $C_{3-8}$ alkenyl group and said $C_{3-9}$ heterocycle may be substituted with one or more substituents;
Ra and Rb are the same or different and each is independently a hydrogen atom, a $C_{1-8}$ alkyl group, a carboxyl $C_{1-8}$ alkyl group, a carboxyl group, an aryl group, a $C_{3-6}$ heterocyclic group containing 1 to 4 heteroatoms selected from the group consisting of O, N and S, or a $C_{3-8}$ cycloalkyl group, or Ra and Rb together with the atom(s) to which they are bonded form a $C_{3-8}$ cycloalkane ring or a $C_{3-9}$ heterocycle containing 1-4 heteroatoms selected from the group consisting of O, N and S, wherein said $C_{1-8}$ alkyl group, said aryl group, said $C_{3-8}$ cycloalkyl group, said $C_{3-8}$ cycloalkane ring and said $C_{3-9}$ heterocycle may be substituted with one or more substituents;
Ring A is an arene, a $C_{3-6}$ heterocycle containing 1-4 heteroatoms selected from the group consisting of O, N and S, or a $C_{3-8}$ cycloalkane ring;
Ya is a hydrogen atom, a halogen atom, a carboxyl group, a hydroxyl group, a carbonyl group, a carboxyl $C_{1-3}$ alkyl group or a sulfo group;
Yb is a hydrogen atom, a halogen atom, a carboxyl group, a hydroxyl group, a carbonyl group, a carboxyl $C_{1-3}$ alkyl group, a nitro group, a cyano group or a $C_{1-3}$ alkoxyl group;
p is 0, 1, 2, 3 or 4;
q is 0 or 1; and
$R^7$ is a hydrogen atom, a halogen atom or a nitro group;
with the proviso that when $R^1$ and $R^2$ are both methyl groups, then neither of $R^4$ nor $R^5$ is an ethyl group substituted with two carboxyl groups, and when $R^1$ and $R^2$ are both methyl groups, then the group represented by formula (II) is not a group represented by formula:

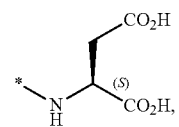

or a pharmaceutically acceptable salt thereof,
to a subject in need thereof.
2. The method according to claim 1, wherein X is —$NR^4R^5$ or a group represented by formula (II), wherein $R^4$, $R^5$ and $R^6$ are each independently a hydrogen atom or a $C_{1-8}$ alkyl group.
3. The method according to claim 1, wherein X is —$NR^4R^5$, wherein $R^4$ and $R^5$ together with the nitrogen atom to which they are bonded form a $C_{3-9}$ heterocycle substituted by a hydrogen atom, a halogen atom, a carboxyl group, a carboxyl $C_{1-3}$ alkyl group or a hydroxyl group.

4. The method according to claim 1, wherein X is a group represented by formula (II), wherein p=1 or 2, and q=0.

5. The method according to claim 1, wherein X is a group represented by formula (II), wherein p=0 and q=1.

6. The method according to claim 1, wherein X is a group represented by formula (II), wherein p=1, q=1, and Ra and Rb are the same or different and each is independently a hydrogen atom or a $C_{1-8}$ alkyl group, or Ra and Rb together with the atom(s) to which they are bonded form a $C_{3-8}$ cycloalkane ring, wherein said $C_{1-8}$ alkyl group and said $C_{3-8}$ cycloalkane ring may substituted with a group selected from the group consisting of a hydrogen atom, a carboxyl group, a carbamoyl group, a hydroxyl group, a phenyl group and a $C_{3-8}$ cycloalkyl group.

7. The method according to claim 1, wherein $R^1$ and $R^2$ are the same or different and each is independently a methyl group, an ethyl group or a propyl group, or $R^1$ and $R^2$ together with the carbon atom to which they are bonded form a cyclobutane ring or a cyclopentane ring.

8. The method according to claim 1, wherein X is a group represented by formula (II), wherein q=1, and Ring A is a benzene ring, a pyridine ring, or a $C_{1-6}$ heterocycle containing 1-4 oxygen atoms.

9. The method according to claim 1, wherein X is a group represented by formula (II), wherein q=1, Ya is a halogen atom, a carboxyl group, a carboxyl $C_{1-3}$ alkyl group, a hydroxyl group, a sulfo group or a carbonyl group, and Yb is a hydrogen atom, a halogen atom, a carboxyl group or a hydroxyl group.

10. The method according to claim 1, wherein X is —$NR^4R^5$, wherein when $R^4$ or $R^5$ has substituent(s), said substituent is selected from the group consisting of a halogen atom, a carboxyl group, a hydroxyl group, a carboxyl $C_{1-3}$ alkyl group, a $C_{3-8}$ alkenyl group, a carbamoyl group, a phenyl group, an amino group, a sulfo group, a cyano group, a $C_{3-8}$ cycloalkyl group, and a $C_{1-8}$ heterocyclic group containing 1 to 4 heteroatoms selected from the group consisting of O, N and S.

11. The method according to claim 1, wherein X is a group represented by formula (II), wherein, when Ra or Rb has substituent(s), said substituent is selected from the group consisting of a carboxyl group, a hydroxyl group, a phenyl group, an amino group, a methylthio group, a thiol group, a carbamoyl group, a guanidino group, a $C_{3-8}$ cycloalkyl group, and a $C_{1-8}$ heterocyclic group containing 1-4 heteroatoms selected from the group consisting of O, N and S.

12. The method according to claim 1, wherein, said compound represented by formula (I) is a compound represented by any of the following formulae:

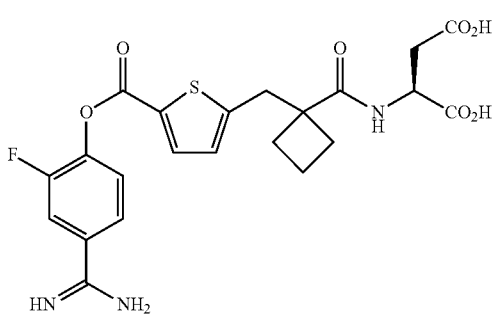

-continued

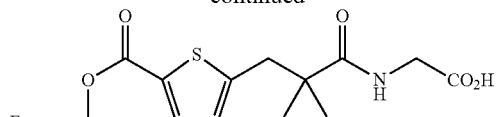

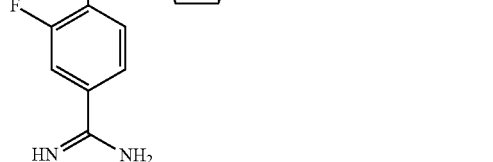

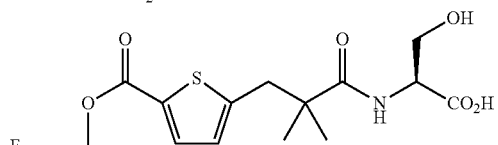

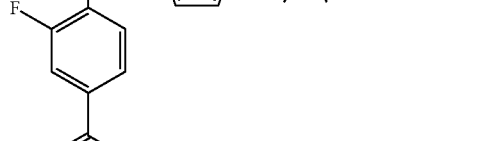

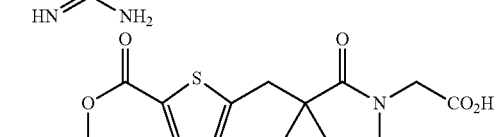

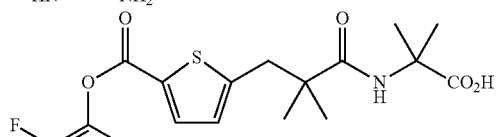

119
-continued
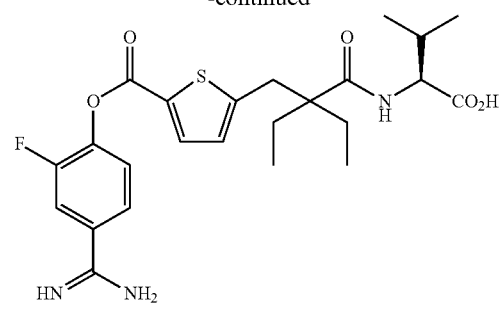
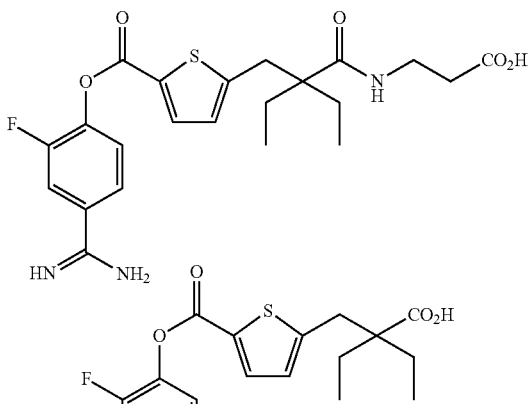
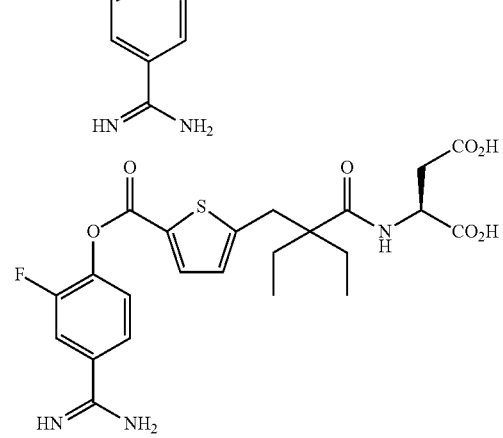
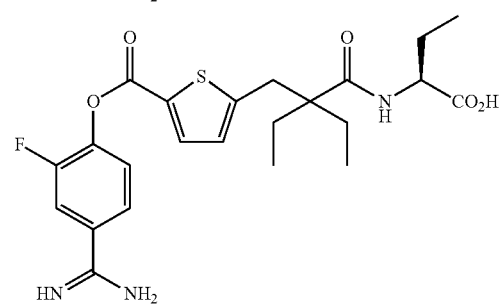
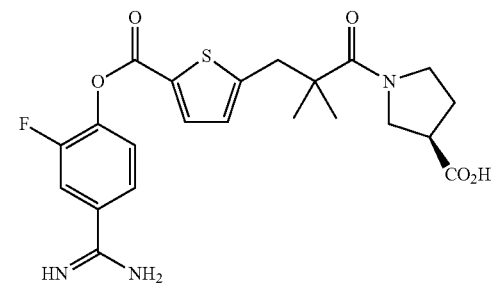
120
-continued
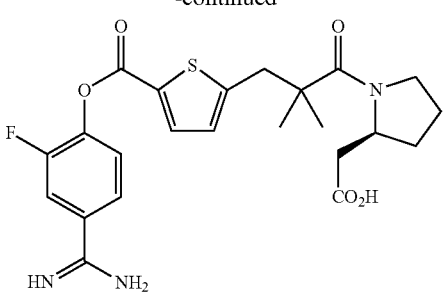
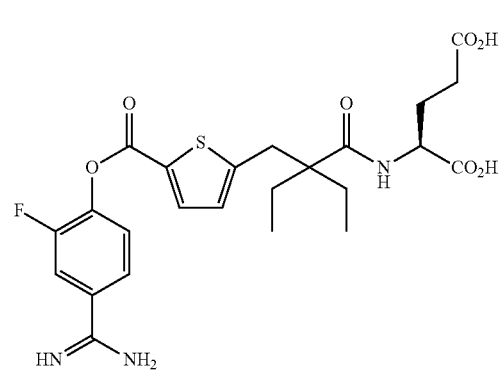
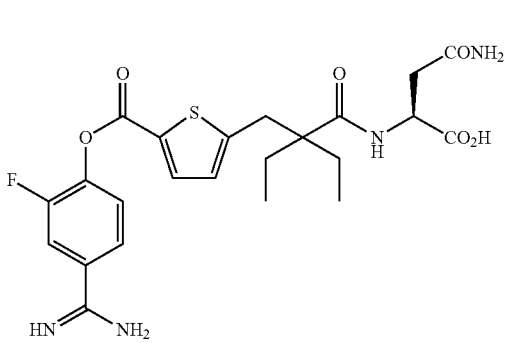
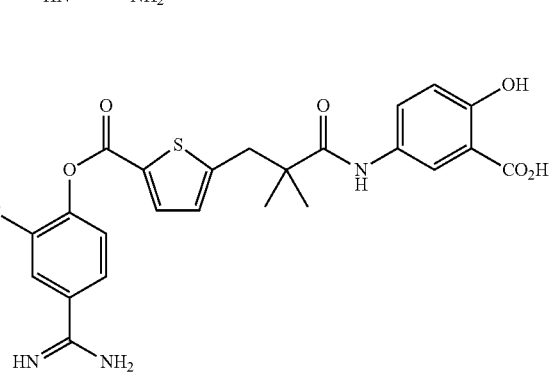
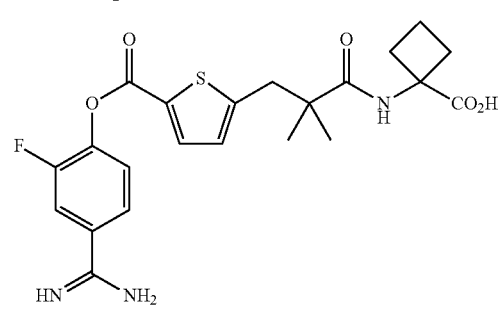

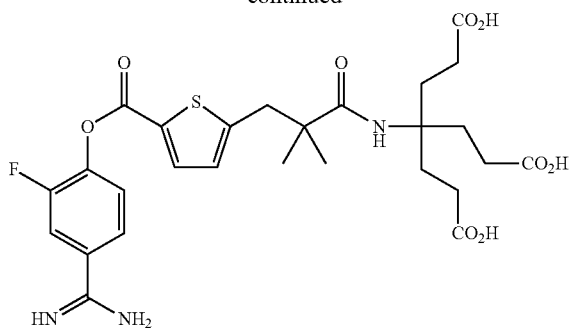
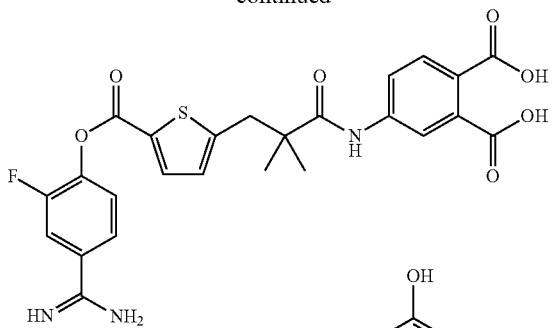
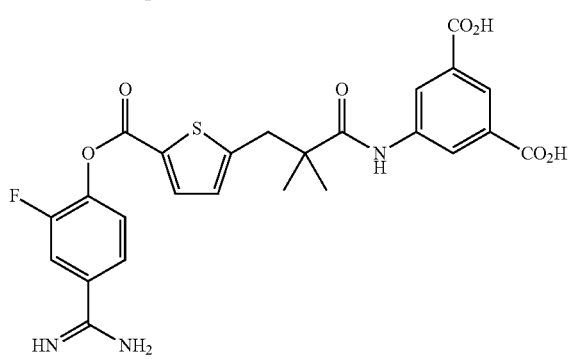
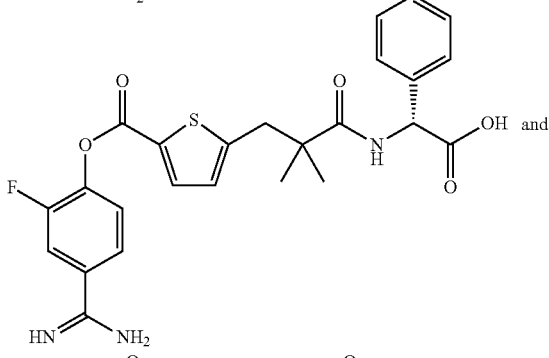
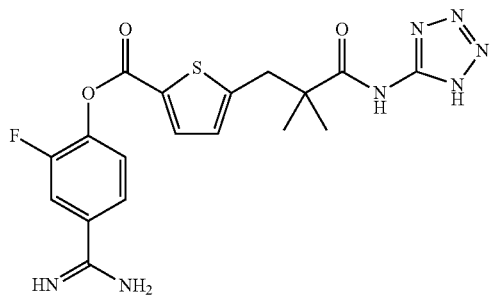
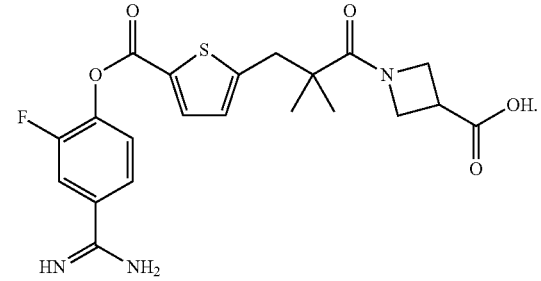
13. The method according to claim 1, wherein said compound represented by formula (I) is a compound represented by any of the following formulae:
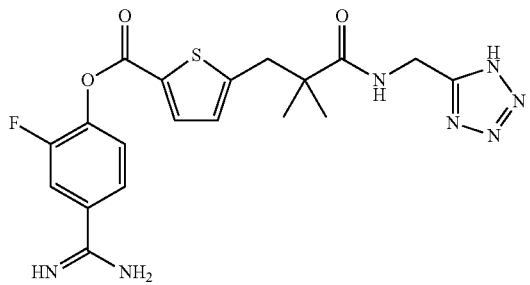
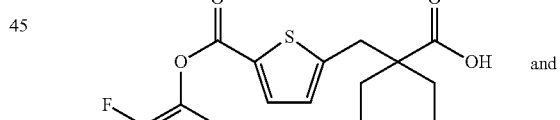
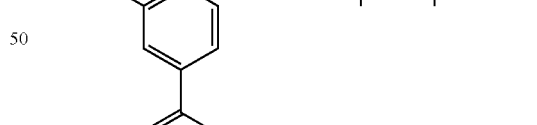
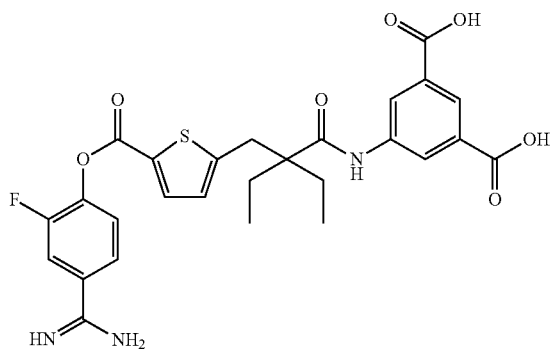
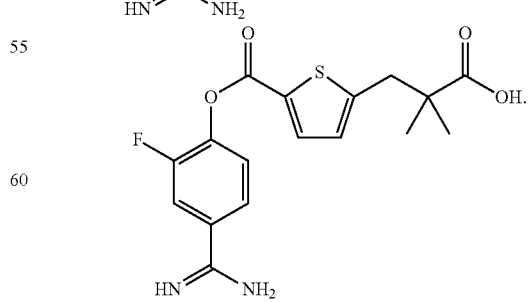
* * * * *